US007919603B2

(12) United States Patent
Nudler et al.

(10) Patent No.: US 7,919,603 B2
(45) Date of Patent: Apr. 5, 2011

(54) HEAT SHOCK RNA

(75) Inventors: Evgeny A. Nudler, New York, NY (US); Ilya Shamovsky, New Providence, NJ (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 11/612,156

(22) Filed: Dec. 18, 2006

(65) Prior Publication Data
US 2007/0238682 A1 Oct. 11, 2007

Related U.S. Application Data

(60) Provisional application No. 60/752,136, filed on Dec. 19, 2005.

(51) Int. Cl.
| C07H 21/04 | (2006.01) |
| C12N 5/00 | (2006.01) |
| C12N 15/00 | (2006.01) |
| C12N 15/74 | (2006.01) |
| C12Q 1/68 | (2006.01) |

(52) U.S. Cl. ........... 536/23.1; 435/6; 435/325; 435/455; 435/471

(58) Field of Classification Search .............. 536/23.1; 435/375
See application file for complete search history.

(56) References Cited

U.S. PATENT DOCUMENTS

2005/0245475 A1* 11/2005 Khvorova et al. .............. 514/44

OTHER PUBLICATIONS

Shamovsky et al., Novel regulatory factors of HSF-1 activation: facts and perspectives regarding their involvement in the age-associated attenuation of the heat shock response, Available online Sep. 21, 2004, Mechanisms of Ageing and Development, vol. 125, pp. 767-775.*
Oshima et al., Cloning, sequencing, and expression of cDNA for human b-glucuronidase, Feb. 1987, PNAS, vol. 84, pp. 685-689.*
Curt D. Sigmund, Viewpoint: Are studies in genetically altered mice out of control? 2000, Atherosclerosis, Thrombosis, Vascular Biology, vol. 20, pp. 1425-1429.*
Rabindran et al., Molecular cloning and expression of a human heat shock factor, HSF1, 1991, PNAS, vol. 88, pp. 6906-6910.*
Brands et al., The primary structure of the alpha subunit of human elongation factor 1 structural aspects of guanine-nucleotide-binding sites, 1986, European Jouranl of Biochemistry, vol. 155, pp. 167-171.*
Allen, et al. "The SINE-Encoded Mouse B2 RNA Represses mRNA Transcription in Response to Heat Shock." Nature Structural & Molecular Biology, vol. 11, No. 9, Sep. 2004, pp. 816-821.
Calderwood, et al. "Targeting HSP70-Induced Thermotolerance for Design of Thermal Sensitizers." International Journal of Hyperthermia, vol. 18, No. 6, 2002, pp. 597-608.
Espinoza, et al. "B2 RNA Binds Directly to RNA Polymerase II to Repress Transcript Synthesis." Nature Structural & Molecular Biology, vol. 11, No. 9, Sep. 2004, pp. 822-829.
Guo, et al. "Evidence for a Mechanism of Repression of Heat Shock Factor 1 Transcriptional Activity by a Multichaperone Complex." The Journal of Biological Chemistry, vol. 276, No. 49, Dec. 7, 2001, pp. 45791-45799.
Hargitai, et al. "Bimoclomol, a Heat Shock Protein Co-Inducer, Acts by the Prolonged Activation of Heat Shock Factor-1." Biochemical and Biophysical Research Communications 307 (2003), pp. 689-695.
Jolly, et al. "Role of the Heat Shock Response and Molecular Chaperones in Oncogenesis and Cell Death." Journal of the National Cancer Institute, vol. 92, No. 19, Oct. 45, 2000, pp. 1564-1572.
Kugel, et al. "Beating the Heat: A Translation Factor and an RNA Mobilize the Heat Shock Transcription Factor HSF-1." Molecular Cell 22, Apr. 21, 2006, pp. 153-154.
Morimoto "Regulation of the Heat Shock Transcriptional Response: Cross Talk Between a Family of Heat Shock Factors, Molecular Chaperones, and Negative Regulators." Genes & Development 12, 1998, pp. 3788-3796.
Nguyen, et al. "7SK Small Nuclear RNA Binds to and Inhibits the Activity of CDK9/Cyclin T Complexes." Nature, vol. 414, Nov. 15, 2001, pp. 322-325.
Nudler, et al. "Methods of Walking with the RNA Polymerase." Methods in Enzymology, vol. 371, 2003, pp. 160-169.
Shamovsky, et al. "RNA-Mediated Response to Heat Shock in Mammalian Cells." Nature, vol. 440, Mar. 23, 2006, pp. 556-560.
Voellmy "On Mechanisms That Control Heat Shock Transcription Factor Activity in Metazoan Cells." Cell Stress & Chaperones, 2004, vol. 9, No. 2, pp. 122-133.
Westerheide, et al. "Heat Shock Response Modulators as Therapeutic Tools for Diseses of Protein Conformation." The Journal of Biological Chemistry, vol. 280, No. 39, Sep. 30, 2005, pp. 33097-33100.
Yang, et al. "The 7SK Small Nuclear RNA Inhibits the CDK9/Cyclin T1 Kinase to Control Transcription." Nature, vol. 414, Nov. 15, 2001, pp. 317-322.
Zou, et al. "Heat Shock Transcription Factor 1 Protects Cardiomyocytes From Ischemia/Reperfusion Injury." Circulation, Dec. 16, 2003, pp. 3024-3030.
Ciocca, et al. "Response of Human Breast Cancer Cells to Heat Shock and Chemotherapeutic Drugs", Cancer Research, Jul. 1, 1992, vol. 52, pp. 3648-3654.
Ianaro, et al. "Anti-Inflammatory Activity of 15-Deoxy-$\Delta^{12,14}$-PGJ$_2$ and 2-Cyclopenten-1-one: Role of the Heat Shock Response", Molecular Pharmacology, 2003, vol. 64, No. 1, pp. 85-93.

(Continued)

Primary Examiner — Dana Shin
(74) Attorney, Agent, or Firm — Fish & Richardson P.C.

(57) ABSTRACT

The present invention provides a novel RNA, designated herein as the "HSR1" (Heat Shock RNA), and its use together with translation elongation factor eEF1A in activation of heat shock transcription factor HSF. The invention further provides the use of HSR1 for generation of novel therapeutics for the treatment of cancer, inflammation, ischemia, neurodegeneration, age-related diseases, HIV infection, deafness, and related disorders.

7 Claims, 7 Drawing Sheets

OTHER PUBLICATIONS

Powers, et al., "Inhibitors of the Heat Shock Response: Biology and Pharmacology", FEBS Letters, 2007, vol. 581, pp. 3758-3769.

Kim et al., Heat-shock proteins: new keys to the development of cytoprotective therapies, Expert Opin. Ther. Targets, 2006, 10:759-769.

Prasanth and Spector, Eukaryotic regulatory RNAs: an answer to the 'genome complexity' conundrum, Genes Dev., 2007, 21:11-42.

Shamovsky and Nudler, Isolation and Characterization of the Heat Shock RNA 1, Methods in Molecular Biology, A. Serganov (ed.), Humana Press, 2009, vol. 540, Chapter 19, pp. 265-279.

* cited by examiner

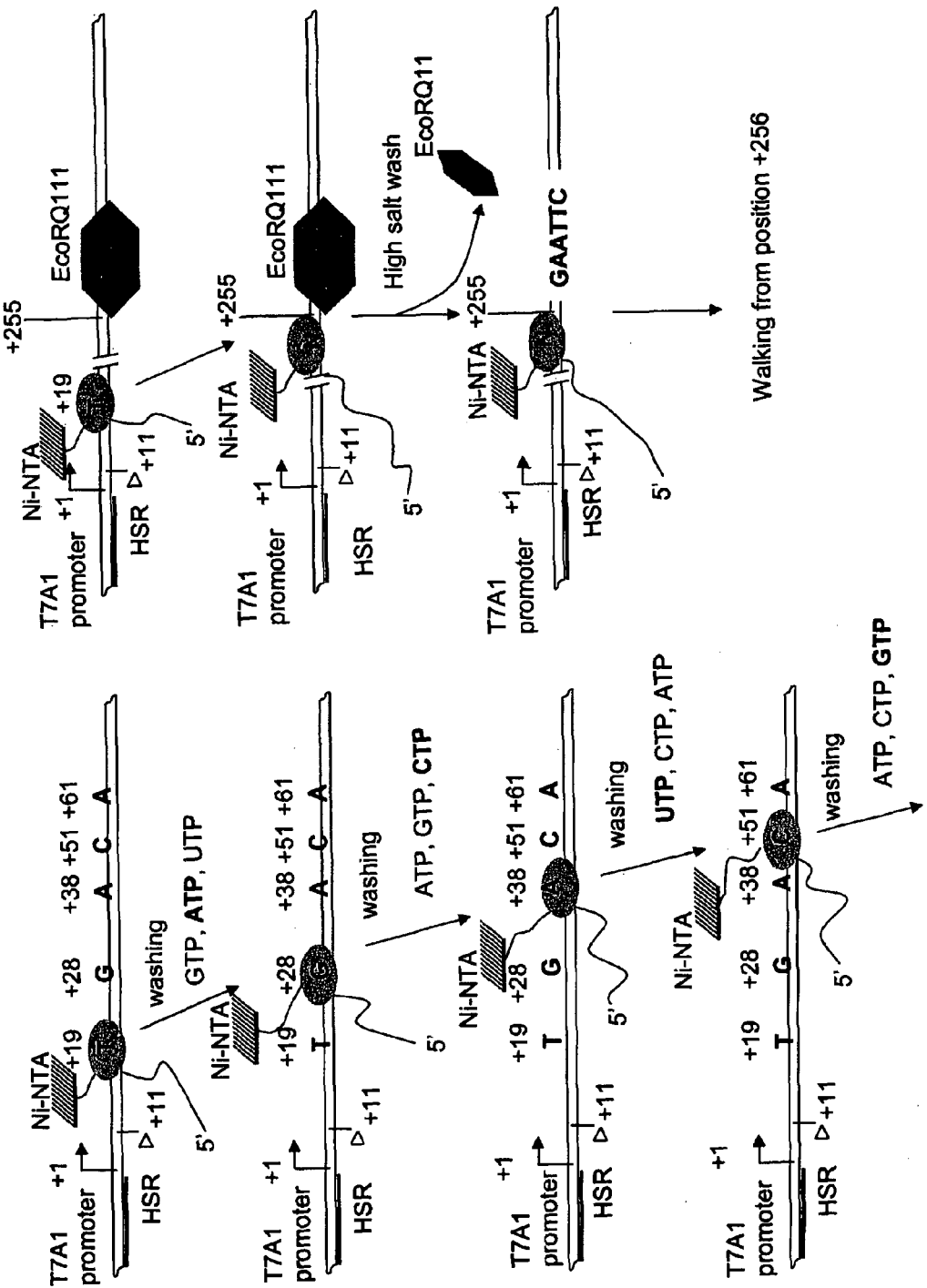

SEQUENCE LISTING

<160> NUMBER OF SEQ ID NOS: 30

<210> SEQ ID NO 1
<211> LENGTH: 604
<212> TYPE: DNA
<213> ORGANISM: hamster

-continued

<400> SEQUENCE: 1

```
ccgtccaatt gaggtccgaa ccggtttaca caaaaatttg acacgcccct gtggggaggc      60
acgatgctgc cttaactctc cgggtgattt catcttcagc gccgaggcgg atgcacctcg     120
ttaaagtgct cgaagcggcg gccatctgca gcactccttc ggcctgggcc gtgtcatagt     180
gtgttgcatc gaccggttga atccgccgcc ataagcagac gttggagtgg tgtgaggact     240
acaatcattc tttaggagat ggcattcctc cttaaaccgc ctcactaagt gacgctaatg     300
atgcctacat tgccccggag actgggctgt gtaggtgcgt tcgcctccag cttttcatcgt    360
ccgggttcat gatctaactc gttgtacaga tgaagccacg tttccacctc catgaccagc     420
ttgctgcgct gacctatcta ggtcgctggc ttgctatctg cattgcaatt gccatgctgg     480
ttggcagtgc atccgccatc tttttgcact cgatggagtg ggccacccaa acgcgggacg     540
ccacaccatt ggctgatatg gggactccca ttcgcaggct tcgatgtcga ctggagtcaa     600
gggc                                                                 604
```

<210> SEQ ID NO 2
<211> LENGTH: 562
<212> TYPE: DNA
<213> ORGANISM: Homo sapiens

<400> SEQUENCE: 2

```
aaaattcgga acgcccctgt ggggaggcac gatgctgcct taactctccg ggtgatttca      60
tcttcagcgc cgagtgcgga tgcacctcgt tgaagtgctc gaaggcggcg gccatctgca     120
gcactccttc ggcctgggcc gtgtcatagt gtgttgcatc gaccggttga atccgccgcc     180
ataagcagac gttggagtgg tgtgaggact acaatcattc tttaggagat ggcattcctc     240
cttaaaccgc ctcactaagt gacgctaatg atgcctacat tgccccggag actgggctgt     300
gtaggtgcgt tcgcctccag cttttcatcgt ccgggttcat gatctaactc gttgtacaga    360
tgaagccacg tttccacctc catgaccagc ttgctgcgct gacctatcta ggtcgctggc     420
ttgctatctg cattgcaatt gccatgctgg ttggcagtgc atccgccatc tttttgcact     480
cgatggagtg ggccacccaa acgcgggacg ccaatcattg gctgatatgg ggactcccat     540
tcgcaggctt cgatgtcgac ac                                             562
```

<210> SEQ ID NO 3
<211> LENGTH: 604
<212> TYPE: DNA
<213> ORGANISM: hamster

<400> SEQUENCE: 3

```
gcccttgact ccagtcgaca tcgaagcctg cgaatgggag tccccatatc agccaatggt      60
gtggcgtccc gcgtttgggt ggcccactcc atcgagtgca aaagatggc ggatgcactg      120
ccaaccagca tggcaattgc aatgcagata gcaagccagc gacctagata ggtcagcgca     180
gcaagctggt catggaggtg aaacgtggc ttcatctgta caacgagtta gatcatgaac      240
ccggacgatg aaagctggag cgaacgcac ctacacagcc cagtctccgg ggcaatgtag      300
gcatcattag cgtcacttag tgaggcggtt taaggaggaa tgccatctcc taaagaatga     360
ttgtagtcct cacaccactc caacgtctgc ttatggcggc ggattcaacc ggtcgatgca     420
acacactatg acacggccca ggccgaagga gtgctgcaga tggccgccgc ttcgagcact     480
ttaacgaggt gcatccgcct cggcgctgaa gatgaaatca cccggagagt taaggcagca     540
tcgtgcctcc ccacaggggc gtgtcaaatt tttgtgtaaa ccggttcgga cctcaattgg     600
```

-continued acgg                                                                604

<210> SEQ ID NO 4
<211> LENGTH: 239
<212> TYPE: DNA
<213> ORGANISM: artificial
<220> FEATURE:
<223> OTHER INFORMATION: Northern probe which hybridizes to the region
      167-405 of cloned hamster or human HSR1

<400> SEQUENCE: 4
ggccgtgtca tagtgtgttg catcgaccgg ttgaatccgc cgccataagc agacgttgga    60
gtggtgtgag gactacaatc attctttagg agatggcatt cctccttaaa ccgcctcact   120
aagtgacgct aatgatgcct acattgcccc ggagactggg ctgtgtaggt gcgttcgcct   180
ccagctttca tcgtccgggt tcatgatcta actcgttgta cagatgaagc cacgtttcc    239

<210> SEQ ID NO 5
<211> LENGTH: 22
<212> TYPE: DNA
<213> ORGANISM: artificial
<220> FEATURE:
<223> OTHER INFORMATION: HSR1-specific PCR primer used for RT-PCR
      (hsrF2(156->177))

<400> SEQUENCE: 5
cgaacgcacc tacacagccc ag                                            22

<210> SEQ ID NO 6
<211> LENGTH: 22
<212> TYPE: DNA
<213> ORGANISM: artificial
<220> FEATURE:
<223> OTHER INFORMATION: HSR1-specific PCR primer used for RT-PCR
      (hsrF8(87->108))

<400> SEQUENCE: 6
tggcggatgc actgccaacc ag                                            22

<210> SEQ ID NO 7
<211> LENGTH: 19
<212> TYPE: DNA
<213> ORGANISM: hamster

<400> SEQUENCE: 7
cggcctgggc cgtgtcata                                                19

<210> SEQ ID NO 8
<211> LENGTH: 19
<212> TYPE: DNA
<213> ORGANISM: hamster

<400> SEQUENCE: 8
cggcctgggc ggtgtcata                                                19

<210> SEQ ID NO 9
<211> LENGTH: 44
<212> TYPE: DNA
<213> ORGANISM: artificial
<220> FEATURE:
<223> OTHER INFORMATION: 1HSR1 antisense oligonucleotide complementary
      to hamster HSR1 [SEQ ID NO: 1] nt 1-44

<400> SEQUENCE: 9
gtgtcaaatt tttgtgtaaa ccggttcgga cctcaattgg acgg                    44

<210> SEQ ID NO 10
<211> LENGTH: 45
<212> TYPE: DNA
<213> ORGANISM: artificial
<220> FEATURE:
<223> OTHER INFORMATION: 2HSR1 antisense oligonucleotide complementary
      to hamster HSR1 [SEQ ID NO: 1] nt 40-84

<400> SEQUENCE: 10
cccggagagt taaggcagca tcgtgcctcc ccacaggggc gtgtc                45

<210> SEQ ID NO 11
<211> LENGTH: 45
<212> TYPE: DNA
<213> ORGANISM: artificial
<220> FEATURE:
<223> OTHER INFORMATION: 5HSR1 antisense oligonucleotide complementary
      to hamster HSR1 [SEQ ID NO: 1] nt 157-201

<400> SEQUENCE: 11
ttcaaccggt cgatgcaaca cactatgaca cggcccaggc cgaag                45

<210> SEQ ID NO 12
<211> LENGTH: 45
<212> TYPE: DNA
<213> ORGANISM: artificial
<220> FEATURE:
<223> OTHER INFORMATION: 6HSR1 antisense oligonucleotide complementary
      to hamster HSR1 [SEQ ID NO: 1] nt 196-240

<400> SEQUENCE: 12
agtcctcaca ccactccaac gtctgcttat ggcggcggat tcaac                45

<210> SEQ ID NO 13
<211> LENGTH: 45
<212> TYPE: DNA
<213> ORGANISM: artificial
<220> FEATURE:
<223> OTHER INFORMATION: anti-6HSR1 oligonucleotide

<400> SEQUENCE: 13
gttgaatccg ccgccataag cagacgttgg agtggtgtga ggact                45

<210> SEQ ID NO 14
<211> LENGTH: 24
<212> TYPE: DNA
<213> ORGANISM: artificial
<220> FEATURE:
<223> OTHER INFORMATION: HSE oligonucleotide (EMSA oligo)

<400> SEQUENCE: 14
gcctcgaatg ttcgcgaagt ttcg                                       24

<210> SEQ ID NO 15
<211> LENGTH: 36
<212> TYPE: DNA
<213> ORGANISM: artificial
<220> FEATURE:
<223> OTHER INFORMATION: Anchored oligo(dT)-Adapter containing SalI site
<220> FEATURE:
<221> NAME/KEY: misc_feature
<222> LOCATION: (1)..(1)
<223> OTHER INFORMATION: v is a, c or g

<400> SEQUENCE: 15
vttttttttt tttttttga ctccagtcga catcga                           36

<210> SEQ ID NO 16
<211> LENGTH: 64
<212> TYPE: DNA
<213> ORGANISM: artificial
<220> FEATURE:
<223> OTHER INFORMATION: cassette containing the H1 promoter followed by
a short hairpin-encoding fragment (HSR1-224)

<400> SEQUENCE: 16
gatccccgga gtggtgtgag gactacttca agagagtagt cctcacacca ctccttttg    60 gaaa                                                                 64

<210> SEQ ID NO 17
<211> LENGTH: 22
<212> TYPE: DNA
<213> ORGANISM: artificial
<220> FEATURE:
<223> OTHER INFORMATION: HSR1-specific PCR primer used for RT-PCR
(hsrR2(351<-372))

<400> SEQUENCE: 17
tgctcgaagc ggcggccatc tg                                             22

<210> SEQ ID NO 18
<211> LENGTH: 22
<212> TYPE: DNA
<213> ORGANISM: artificial
<220> FEATURE:
<223> OTHER INFORMATION: HSR1-specific PCR primer used for RT-PCR
(hsrR15(471<-492))

<400> SEQUENCE: 18
tcttcagcgc cgaggcggat gc                                             22

<210> SEQ ID NO 19
<211> LENGTH: 20
<212> TYPE: DNA
<213> ORGANISM: artificial
<220> FEATURE:
<223> OTHER INFORMATION: HSR1-specific PCR primer used for RT-PCR
(HSR-T3as)

<400> SEQUENCE: 19
gcccttgact ccagtcgaca                                                20

<210> SEQ ID NO 20
<211> LENGTH: 19
<212> TYPE: DNA
<213> ORGANISM: hamster

<400> SEQUENCE: 20
ggagtggtgt gaggactac                                                 19

<210> SEQ ID NO 21
<211> LENGTH: 19
<212> TYPE: DNA
<213> ORGANISM: hamster

<400> SEQUENCE: 21
ggactggtgt gaggactac                                                 19

<210> SEQ ID NO 22
<211> LENGTH: 19
<212> TYPE: DNA
<213> ORGANISM: artificial
<220> FEATURE:

<223> OTHER INFORMATION: siHSR1-160 antisense

<400> SEQUENCE: 22
tatgacacgg cccaggccg                                                    19

<210> SEQ ID NO 23
<211> LENGTH: 19
<212> TYPE: DNA
<213> ORGANISM: artificial
<220> FEATURE:
<223> OTHER INFORMATION: mutant siHSR1-160 (mut160 (C11->G)) antisense

<400> SEQUENCE: 23
tatgacaccg cccaggccg                                                    19

<210> SEQ ID NO 24
<211> LENGTH: 19
<212> TYPE: DNA
<213> ORGANISM: artificial
<220> FEATURE:
<223> OTHER INFORMATION: siHSR1-224 antisense

<400> SEQUENCE: 24
gtagtcctca caccactcc                                                    19

<210> SEQ ID NO 25
<211> LENGTH: 19
<212> TYPE: DNA
<213> ORGANISM: artificial
<220> FEATURE:
<223> OTHER INFORMATION: mutant siHSR1-224 (mut224 (G4->C)) antisense

<400> SEQUENCE: 25
gtagtcctca caccagtcc                                                    19

<210> SEQ ID NO 26
<211> LENGTH: 9
<212> TYPE: DNA
<213> ORGANISM: artificial
<220> FEATURE:
<223> OTHER INFORMATION: siRNA bubble sequence

<400> SEQUENCE: 26 ttcaagaga                                                                9

<210> SEQ ID NO 27
<211> LENGTH: 47
<212> TYPE: DNA
<213> ORGANISM: hamster

<400> SEQUENCE: 27
cggcctgggc cgtgtcatat tcaagagata tgacacggcc caggccg                     47

<210> SEQ ID NO 28
<211> LENGTH: 47
<212> TYPE: DNA
<213> ORGANISM: hamster

<400> SEQUENCE: 28
ggagtggtgt gaggactact tcaagagagt agtcctcaca ccactcc                     47

<210> SEQ ID NO 29
<211> LENGTH: 47
<212> TYPE: DNA
<213> ORGANISM: hamster

-continued

```
<400> SEQUENCE: 29
cggcctgggc ggtgtcatat tcaagagata tgacaccgcc caggccg                    47

<210> SEQ ID NO 30
<211> LENGTH: 47
<212> TYPE: DNA
<213> ORGANISM: hamster

<400> SEQUENCE: 30
ggactggtgt gaggactact tcaagagagt agtcctcaca ccagtcc                    47
```

HEAT SHOCK RNA

CROSS-REFERENCE TO RELATED APPLICATIONS

This application claims priority under 35 U.S.C. §119, to U.S. Provisional Application Ser. No. 60/752,136 filed Dec. 19, 2005, the disclosure of which is hereby incorporated by reference in its entirety.

STATEMENT REGARDING FEDERALLY SPONSORED RESEARCH OR DEVELOPMENT

The research leading to the present invention was supported, in part, by the Edward Mallinckrodt Jr. Foundation and grant from NIH GM69800. Accordingly, the U.S. government has certain rights in the invention.

FIELD OF THE INVENTION

The present invention provides a novel RNA, designated herein as the "HSR1" (Heat Shock RNA), and its use together with translation elongation factor eEF1A in activation of heat shock transcription factor HSF. The invention further provides the use of HSR1 for generation of novel therapeutics for the treatment of cancer, inflammation, ischemia, neurodegeneration, age-related diseases, HIV infection, deafness, and related disorders.

BACKGROUND OF THE INVENTION

All organisms respond to extreme environmental conditions by either inducing de novo or dramatically increasing the expression of a number of genes that protect the cell from the deleterious effect of intracellular protein denaturation. These genes encode for a family of proteins called HSPs (heat shock proteins) and other molecular chaperones and cytoprotective proteins. Expression of HSPs and other chaperones is induced upon exposure to a variety of stressors including elevated temperature, oxidative stress, alcohol, hyper- and hypoosmotic stress, transition metals, viral infection, amino acid analogs, etc. (Morimoto, et al., In The Biology of Heat Shock Proteins and Molecular Chaperones, 1994 (New York: Cold Spring Harbor Press), pp. 417-455). HSPs are involved in basic cellular processes under both stress and normal conditions such as correct folding of nascent polypeptides, binding to exposed hydrophobic regions of denatured or abnormal proteins to prevent their aggregation and promote degradation, and translocation of proteins into membrane-bound organelles in the cell. Expression of some HSPs is essential during embryogenesis (Luft, et al., Chaperones. 1999; 4:162-170). In addition, certain HSPs are required to stabilize otherwise unstable proteins or complexes of proteins. The signal-transducing proteins such as steroid hormone receptors (Pratt, Annu. Rev. Pharmacol. Toxicol. 1997; 37:297-326) and protein kinases (Donze, et al., Mol. Cell Biol. 1999; 19:8422-8432; Louvion, et al., Mol. Biol. Cell 1998; 9:3071-3083; Zhu, et al., Development 1997; 124:3007-3014) have been the most extensively investigated such proteins.

HSP family proteins are classified into several groups based on their molecular weight and sequence homology. In mammals, major HSP classes are HSP70, HSP40, HSP90, and HSP27. HSP70 subfamily includes molecular chaperones that participate in folding of nascent polypeptide chains (Mayer, et al., Adv. Protein Chem. 2001; 59:1-44), unfolding and refolding of proteins during their transport across membranes (Jensen, et al., Curr. Biol. 1999; 9:R779-R782; Pilon, et al., Cell 1999; 97:679-682; Ryan, et al., Adv. Protein Chem. 2001:59:223-242), binding to partially denatured, abnormal, or targeted for proteasome degradation proteins (Zylicz, et al., IUBMB. Life 2001; 51:283-287). Bacterial counterpart for HSP70 is DnaK protein. HSP70 subfamily includes both constitutive and stress-inducible proteins that are closely related and often referred to as Hsc70 and HSP72 respectively. HSP40 is a co-chaperon for HSP70 class proteins, which modulates ATPase activity and substrate binding properties of the latter. Its bacterial analog is DnaJ (Ohtsuka, et al., Int. J. Hyperthermia 2000; 16:231-245). HSP90 is ubiquitously expressed and may constitute up to 1-2% of total cellular protein. Mammalian cells express at least two HSP90 isoforms, HSP90α and HSP90β, which are encoded by two separate genes (Pearl, et al., Adv. Protein Chem. 2001; 59:157-186). Under stress conditions HSP90 binds to exposed hydrophobic regions of denatured proteins, while in the absence of stress it participates in fundamental cellular processes such as hormone signaling and cell cycle control (Pearl, et al., Curr. Opin. Struct. Biol. 2000; 10:46-51). Many regulatory proteins, including steroid hormone receptor, cell cycle kinases, and p53 have been identified as HSP90 substrates (Young, et al., J. Cell Biol. 2001; 154:267-273; Pratt, Annu. Rev. Pharmacol. Toxicol. 1997; 37:297-326). HSP25/27 belongs to a family of small heat shock proteins, which includes primate HSP27, rodent HSP25, αA-crystallins and αB-crystallins. HSP25/27 is expressed constitutively and expression increases after exposure to heat, transition metal salts, drugs, and oxidants. It forms oligomers consisting of 8-40 monomers that serve as binding sites for unfolding peptides until they can be refolded by HSP70/HSP40 system (Van Montfort, et al., Adv. Protein Chem. 2001; 59:105-156; Welsh, et al., Ann. N.Y. Acad. Sci. 1998; 851:28-35).

The induction of HSP gene expression occurs primarily at transcriptional level and is mediated by a family of transcription factors named HSF (Heat Shock Factor). Whereas vertebrates and plants have at least four members of the HSF family, only one HSF is expressed in yeast, *Drosophila*, and *C. elegans* (Wu, Ann. Rev. Cell Dev. Biol. 1995; 11:441-469). In human cells, three HSFs (HSF1, HSF2, and HSF4) have been characterized (Morimoto, et al., Genes Dev. 1998; 12:3788-3796). HSF1 is ubiquitously expressed and plays the principle role in the stress-induced expression of HSPs. It is an apparent functional analog of *Drosophila* HSF.

Under normal conditions, HSF1 exists in the cell as an inactive monomer. Following exposure to elevated temperature, HSF1 trimerizes and apparently relocates to the nucleus where it binds to specific sites in HSP promoters upstream of the transcription initiation site (Wu, Ann. Rev. Cell Dev. Biol. 1995; 11:441-469; Westwood, et al., Mol. Cell Biol. 1993; 13:3481-3486; Westwood, et al., Nature 1991; 353:822-827). The HSF binding site contains arrays of inverted repeats of the element NGAAN designated HSE (Heat Shock Element). The same evolutionarily conserved HSE sequence is recognized by all members of the HSF protein family and is universal to all eukaryotic species (Kim et al., Protein Sci. 1994; 3:1040-1051). The heat shock promoter is primed for rapid activation in response to heat shock. Many factors of the basal transcription machinery are bound to the promoter prior to heat shock including GAGA factor, TFIID, transcriptionally arrested RNA polymerase II located 21-35 nucleotides downstream of the transcription start site, and presumably some other transcription factors (Shopland, et al., Genes Dev. 1995; 9:2756-2769). The partitioning of HSF molecules between the nucleus and cytoplasm is a subject to some controversy since, in the case of *Xenopus laevis*, HSF1 was shown to be a nuclear protein before heat shock (Mercier, et al., J. Biol.

Chem. 1997; 272:14147-14151), while in most studies employing mammalian cells, HSF1 was found in both the cytoplasm and nucleus under normal conditions (Sarge, et al., Mol. Cell Biol. 1993b; 13:1392-1407). Interestingly, heat shock treatment of HeLa cells results in rapid and reversible localization of HSF1 in specific nuclear granules, which constitute a novel type of nuclear protein compartmentalization (Cotto, et al., Journal of Cell Science 1997b; 110:2925-2934). The granules appear within 30 sec of heat shock treatment and rapidly disappear upon shift to normal temperature. However, the functional significance of this phenomenon is still unknown.

The overall structure of HSF1 is conserved among species as distant as *Drosophila* and human. The DNA-binding domain is just over 100 amino acids long and is situated close to the N-terminus of the molecule. This domain is about 70% homologous between human HSF1 and *Drosophila* HSF and shows 55% homology between human HSF1 and yeast HSF. The leucine zipper domain, which is C-terminal with respect to the DNA-binding domain, is even more conserved showing 79% homology between human and *Drosophila*. In vertebrates, this domain comprises three hydrophobic heptad repeats with an additional heptad repeat located in the C-terminus of HSF1. It has been implicated in the maintenance of the inactive monomeric state of HSF1 under non-stressful conditions (Wu, et al., In The Biology of Heat Shock Proteins and Molecular Chaperones, 1994 (New York: Cold Spring Harbor Press), pp. 395-416).

A number of models have been proposed to explain how HSF activation is regulated, most of them focusing on repression of the inactive monomer under normal conditions as the most probable mode of regulation. Several lines of evidence suggest the existence of a titratable cellular factor that acts to repress HSF under normal conditions by keeping it in a monomeric form. Indeed, overexpression of both HSF1 and HSF2 in 3T3 mouse fibroblasts resulted in constitutive activation of their DNA-binding activity and transcription of HSP genes (Sarge, et al., Mol. Cell Biol. 1993a; 13:1392-1407). The observed effect could reflect either general cellular stress caused by the drastic increase in HSF concentration or titration of the negative regulator of HSF, which is present in limiting amounts. Furthermore, expression of human HSF1 in *Drosophila* cells results in a decrease of the activation threshold temperature by 9 degrees, to the temperature characteristic for the heat shock conditions in *Drosophila* (32° C.) instead of 41° C.—a characteristic threshold for mammalian cells. At the same time, *Drosophila* HSF expressed in human cells remained constitutively active even when the temperature was lowered to 25° C.—the normal growth temperature for *Drosophila* (Clos, et al., Nature 1993; 364:252-255). Similarly, *Arabidopsis* HSF remained active in *Drosophila* and human cells even under control conditions (Hubel, et al., Mol. Gen. Genet. 1995; 248:136-141). Taken together, these results strongly suggest that the intracellular environment rather than structure of the HSF molecule determines its behavior in response to heat stress. These data are consistent with the possibility that HSF activation is mediated by a specific stimulating factor(s).

The process of HSF1 activation can be divided into at least two steps: 1) trimerization and acquisition of DNA binding activity; 2) acquisition of transactivation competence, which is correlated with hyperphosphorylation of the factor. Treatment with salicylate and other non-steroid anti-inflammatory drugs induces HSF trimerization and DNA binding but fails to stimulate transcription of HSP genes (Jurivich, et al., J. Biol. Chem. 1995a; 270:24489-24495). However, majority of HSF regulation occurs at the level of its trimerization.

The model of HSF regulation, where HSF activity is a subject to the negative feedback mechanism involving inducible HSP72 and other chaperones, has been a paradigm for a decade. According to this model, HSF monomer is present in the complex with HSP72 and other chaperones (most notably HSP90) under normal conditions. Trimerization of HSF molecules is thought to occur spontaneously as soon as negative regulation by HSPs has been relieved. Indeed, in a number of studies HSF has been shown to possess intrinsic responsiveness to heat (Zuo, et al., Mol. Cell Biol. 1995; 15:4319-4330; Farkas, et al., Molecular and Cellular Biology 1998a; 18:906-918). However, the HSF concentrations used in these studies far exceeded those found in the cell, which questions the physiological relevance of the data. Furthermore, although all these studies imply that HSF trimerization occurs spontaneously once the negative regulation is relieved, the existence of a positive regulation of HSF activity can not be ruled out. For example, the rapid, specific and reversible formation of HSF granules in nuclei during heat shock (Cotto, et al., Journal of Cell Science 1997a; 110:2925-2934; Jolly, et al., Journal of Cell Science 1997; 110:2935-2941) testifies against spontaneous mechanism given the relatively low number of HSF molecules in the cell, their even distribution throughout cytoplasm under normal conditions, and molecular crowding effect due to very high total protein concentration in the cell as compared to in vitro experimental systems.

HSPs, and HSP70 family in particular, is considered a part of a protective mechanism against certain pathological conditions, including ischemic damage, infection, and inflammation (Pockley, Circulation 2002; 105:1012-1017). In the case of inflammation, a protective role of HSPs has been shown in a variety of experimental models (Jattela et al., EMBO J. 1992; 11:3507-3512; Morris et al., Int. Biochem. Cell Biol. 1995; 27:109-122; Ianaro et al., FEBS Lett. 2001; 499:239-244; Van Molle et al., Immunity 2002; 16:685-695). For example, Ianaro et al. (Mol. Pharmacol. 2003; 64:85-93) have recently demonstrated that HSF1-induced (see below) HSP72 expression in the inflamed tissues and activation of the heat shock response is closely associated with the remission of the inflammatory reaction. It follows, that HSP genes may function as anti-inflammatory or "therapeutic" genes, and their selective in vivo transactivation may lead to remission of the inflammatory reaction (Ianaro et al., FEBS Lett. 2001; 499:239-244 and Ianaro et al., FEBS Lett. 2001; 508:61-66).

A potential therapeutic value of causing increased expression of HSPs in individuals suffering from cerebral or cardiac ischemia and neurodegenerative diseases has been also suggested (Klettner, Drug News Perspect. 2004; 17:299-306; Hargitai et al., Biochem. Biophys. Res. Commun. 2003; 307: 689-695; Yenari et al., Ann. Neurol. 1998; 44:584-591; Suzuki et al., J. Mol. Cell Cardiol. 1998; 6:1129-1136; Warrik et al., Nat. Genet. 1999; 23:425-428). For example, Zou et al. (Circulation 2003; 108:3024-3030) have recently shown that cardiomyocyte cell death induced by hydrogen peroxide was prevented by overexpression of HSF1 in COS7 cells. Thermal preconditioning at 42° C. for 60 minutes activated HSF1, which played a critical role in survival of cardiomyocytes from oxidative stress. Ischemia/reperfusion injury has been reported to induce apoptosis in cardiomyocytes (Fliss and Gattinger, Circulation 1996; 79:949-956). Zou et al. (Circulation 2003; 108:3024-3030) have also demonstrated that, in the heart of transgenic mice overexpressing a constitutively active form of HSF1 (and having elevated levels of HSPs 27, 70 and 90 in the heart), ischemia followed by reperfusion-induced ST-segment elevation in ECG was recovered faster, infarct size was smaller, and cardiomyocyte death was less than in wild-type mice. These results suggest that elevated activity of HSF1 (and levels of HSPs) exert protective effect on the electrical activity of myocardium against ischemia/reperfusion injury (see also Plumier et al., J. Clin. Invest. 1995; 95:1854-1860; Marber et al., ibid., pp. 1446-1456; Radford et al., Proc. Natl. Acad. Sci. USA, 1996; 93:2339-2342).

HSPs and HSF1 have been also implicated in protection against a variety of neurodegenerative disorders that involve aberrant protein folding and protein damage. Neuronal cells are particularly vulnerable in this sense as HSF activity and HSP expression are relatively weak in such cells and motor neurons appear to require input of HSP secreted from adjacent glial cells to maintain adequate molecular chaperone levels (Batulan et al., J. Neuosci. 2003; 23:5789-5798; Guzhova et al., Brain Res. 2001; 914:66-73).

Polyglutamine (polyQ) expansion is a major cause of inherited neurodegenerative diseases called polyglutamine diseases. Several polyQ diseases have been identified, including Huntington's disease (HD), spinobulbar muscular atrophy, dentatorubral pallidoluysian atrophy, Kennedy disease, and five forms of spinocerebellar ataxia. Aggregates or inclusion bodies of polyQ proteins (e.g., huntingtin) within the nucleus, or in the cytoplasm of neuronal cells in some Huntington's disease patients, are a prominent pathological hallmark of most polyQ diseases (Davies et al., Cell 1997; 90:537-548; DiFiglia et al., Science 1997; 277:1990-1993). Formation of polyQ protein inclusions correlates with an increased susceptibility to cell death (Warrik et al., Cell 1998; 94:939-49). The early stages of aggregates are highly toxic to cells (Bucciantini et al., Nature 2002; 416:507-11). Suppression of aggregates should be beneficial to cells and could delay the progression of polyQ diseases (Sanchez et al., Nature 2003; 421:373-9). HSPs have been implicated in many of these neurodegenerative diseases based on the association of chaperones with intracellular aggregates. For example, live cell imaging experiments show that Hsp70 associates transiently with huntingtin aggregates, with association-dissociation properties identical to chaperone interactions with unfolded polypeptides (Kim et al., Nat. Cell Biol. 2002; 4:826-31). This suggests that these chaperone interactions may reflect the efforts of Hsp70 to direct the unfolding and dissociation of substrates from the aggregate. Moreover, overexpression of the Hsp70 chaperone network suppresses aggregate formation and/or cellular toxicity. A critical protective role for small HSPs (HSP27) has been also recently demonstrated in Huntington's disease (Wyttenbach et al., Human Mol. Gen. 2002; 11:1137-51). Collectively, these observations have led to the hypothesis that the elevated levels of heat shock proteins reduce or dampen aggregate formation and cellular degeneration (Warrick et al., Nat. Genet. 1999; 23:425-8; Krobitsch and Lindquist, Proc. Natl. Acad. Sci. USA 2000; 97:1589-94). Importantly, HSF1 overexpression suppressed polyQ-inclusion formation even better than any combination of HSPs in culture cells and in Huntington's disease model mice extending their life span (Fujimoto et al., J. Biol. Chem. 2005; 280:34908-16).

Multiple HSPs are also overexpressed in brains from Alzheimer's (AD) and Parkinson's disease (PD) patients and found to be associated with senile plaques and Lewy bodies, respectively. These HSPs may be involved in neuroprotection by various mechanisms ranging from microglia activation and clearance of amyloid-β peptides to suppression of apoptosis (Kitamura and Nomura, Pharmacol Ther. 2003; 97:35-33).

Ageing is also associated with the decrease in activity of HSF (Tonkis and Calderlwood, Int. J. Hyperthermia 2005; 21:433-444). Indeed, neurodegenerative diseases often occur later in life when heat shock genes seem to be induced poorly (Soti and Csermely, Exp. Gerontol. 2003; 38:1037-40; Shamovsky and Gershon, Mech. Ageing Dev. 2004; 125:767-75). Moreover, it has been recently shown that induction of heat shock either by temperature or HSF overexpression could extend life span in model organisms. For example, the heat shock response has recently been implicated in the regulation of longevity in *Caenorhabditis elegans* in a pathway that overlaps with the insulin signaling pathway (Hsu et al., Science 2003; 300:1142-5; Morley and Morimoto, Mol. Biol. Cell 2004; 15:657-64). Reduction of HSF1 levels cause a decreased life span in *C. elegans*, similar to life span effects observed in mutants of Daf-16, a FOXO transcription factor in the insulin signaling pathway. Daf-16 and HSF1 share a subset of downstream target genes, including small HSPs. RNA interference experiments showed that a decrease in small HSPs and other HSPs leads to a decrease in longevity (Hsu et al., Science 2003; 300:1142-5; Morley and Morimoto, Mol. Biol. Cell 2004; 15:657-64). Similarly, Walker et al. (Aging Cell 2003; 2:131) have demonstrated that overexpression of HSP16 can extend *C. elegans'* life span. Therefore, in addition to the prevention of diseases of aging, increased levels of HSPs may lead to increases in life span (Westerheide and Morimoto, J. Biol. Chem. 2005; 280: 33097-100).

Heat shock is a known transcriptional activator of human immunodeficiency virus type 1 (HIV) long terminal repeat (LTR). However, HIV LTR suppression can occur under hyperthermic conditions. Specifically, suppression of the HIV LTR was observed in a conditional expression system for gene therapy applications that utilizes the heat-inducible promoter of the human heat shock protein 70B gene to enhance the HIV LTR-driven therapeutic gene expression after hyperthermia (temperature higher than 37° C.) (Gemer et al., Int. J. Hyperthermia 2000; 16:171-181). Similarly, the inhibition of HIV transcription has been reported after whole-body hyperthermia at 42° C. in persons with AIDS (Steinhart et al., J. AIDS Hum. Retrovirol. 1996; 11:271-281). Recently demonstrated ability of a mutant transcriptionally active HSF1 (lacking C-terminal residues 203-315) to suppress HIV promoter activity further suggests that HSF1 could serve as a tool for the treatment of AIDS (Ignatenko and Gemer, Exp. Cell Res. 2003; 288:1-8; see also Brenner and Wainberg, Expert Opin. Biol. Ther. 2001; 1:67-77).

Due to interaction of HSPs with numerous regulatory proteins (e.g., NF-κB, p53, v-Src, Raf1, Akt, steroid hormone receptors) and pathways (e.g., inhibition of c-Jun NH2-terminal kinase (JNK) activation, prevention of cytochrome c release, regulation of the apoptosome, prevention of lysosomal membrane permeabilization, prevention of caspase activation) involved in the control of cell growth, the increased production of HSPs has potent anti-apoptotic effect (Bold, et al., Surgical Oncology-Oxford 1997; 6:133-142; Jaattela, et al., Exp. Cell Res. 1999; 248:30-43; Nylandsted, et al., Ann. N.Y. Acad. Sci. 2000; 926:122-125; Pratt and Toft, Exp. Biol. Med. (Maywood) 2003; 228:111-33; Mosser and Morimoto, Oncogene 2004; 23:2907-18). Anti-apoptotic and cytoprotective activities of HSPs directly implicate them in oncogenesis (Jolly and Morimoto, J. Natl. Cancer Inst. 2000; 92:1564-72; Westerheide and Morimoto, J. Biol. Chem. 2005; 280: 33097-100). Many cancer cells display deregulated expression of HSPs, whose elevated levels contribute to the resistance of cancerous cells to chemo- and radiotherapy. Different subfamilies of HSPs including HSP70, HSP90, and HSP27 were found to be expressed at abnormal levels in various human tumors (Cardoso, et al., Ann. Oncol. 2001; 12:615-620; Kiang, et al., Mol. Cell Biochem. 2000; 204:

169-178). In some cases, HSPs are expressed at cell surface in tumors, most probably serving as antigen presenting molecules in this case (Conroy, et al., Eur. J. Cancer 1998; 34:942-943). Both HSP70 and HSP90 were demonstrated to mediate cytoplasmic sequestration of p53 in cancer cells (Elledge, et al., Cancer Res. 1994; 54:3752-3757). Inactivation of wild-type p53 function has been observed in variety of cancer cells and is in fact one of the most common hallmarks in human cancer (Malkin, et al., J. Neurooncol. 2001; 51:231-243). Other studies have demonstrated that HSP70 has a potent general antiapoptotic effect protecting cells from heat shock, tumor necrosis factor, serum starvation, oxidative stress, chemotherapeutic agents (e.g., gemcitabine, torootecan, actinomycin-D, campothecin, and etoposide), and radiation (Jaattela, et al., EMBO J. 1992; 11:3507-3512; Jaattela, et al., J. Exp. Med. 1993; 177:231-236; Simon, et al., J. Clin. Invest 1995; 95:926-933; Karlseder, et al., Biochem. Biophys. Res. Commun. 1996; 220:153-159; Samali and Cotter, Exp. Cell Res. 1996; 223:163-170; Sliutz et al., Br. J. Cancer 1996; 74:172-177). At the same time, HSP70 is abundantly expressed in human malignant tumors of various origins, not only enhancing spontaneous growth of tumors, but also rendering them resistant to host defense mechanisms and therapeutic treatment (Ciocca, et al., Cancer Res. 1992; 52:3648-3654). Therefore, finding a way to suppress HSP overproduction in cancerous cells will be invaluable for increasing the efficacy of the existing anti-cancer therapeutic approaches.

HSF1-mediated induction of HSPs has been also implicated in protection of sensory hair cells against acoustic overexposure, hyperthermia and ototoxic drugs. It has been shown that mice lacking HSF1 have reduced recovery from noise-induced hearing loss (Altschuler et al., Audiol Neotol. 2003; 7:152-156). Similarly, Sugahara et al. (Hear Res. 2003; 182: 88-96) have demonstrated that the loss of sensory hair cells was more significant in HSF1-null mice compared with that of wild-type mice when mice were subjected to acoustic overexposure. They have also shown that the loss of both the sensory hair cells and the auditory function induced by acoustic overexposure was inhibited by pretreatment of the inner ear with local heat shock.

Based on the information provided above, HSF1 appears to be an attractive therapeutic target for regulating HSP synthesis to combat cancer, inflammation, ischemia, neurodegeneration, age-related diseases, HIV infection, deafness, and related disorders (Mestril et al., J. Clin. Invest. 1994; 93:759-67; Morimoto, et al., Genes Dev. 1998; 12:3788-3796; Jolly and Morimoto, J. Natl. Cancer Inst. 2000; 92:1564-72; Ianaro et al., FEBS Lett. 2001; 499:239-44; Calderwood and Asea, Int. J. Hyperthermia 2002; 18:597-608; Zou et al., Circulation 2003; 108:3024-30; Westerheide and Morimoto, J. Biol. Chem. 2005; 280:33097-100).

SUMMARY OF THE INVENTION

As follows from the Background Section, there is a clear need in the art to develop novel therapeutically effective regulators of HSF. The present invention satisfies this and other needs by disclosing for the first time two HSF-associated factors, translation elongation factor eEF1A and a novel Heat Shock RNA (HSR1), that mediate HSF activation upon heat shock under physiological conditions. As disclosed herein, eEF1A and HSR1 form a ternary complex with HSF1 in vitro and in vivo. The present invention further provides novel therapeutics that affect activity of the ternary complex or any of its individual components and in this way can be used to treat cancer, inflammation, ischemia, neurodegeneration, age-related diseases, HIV infection, deafness, and related disorders.

Specifically, the first object of the present invention is to provide an isolated ribonucleotide molecule comprising a eukaryotic Heat Shock RNA (HSR1) or a fragment thereof. In one embodiment, the present invention provides an isolated ribonucleotide molecule comprising hamster HSR1 having SEQ ID NO: 1. In another embodiment, the present invention provides an isolated ribonucleotide molecule comprising human HSR1 having SEQ ID NO: 2. In a separate embodiment, the invention also provides an isolated polynucleotide molecule (e.g., a gene or vector) encoding a eukaryotic HSR1 or a fragment thereof. The invention also provides an isolated single-stranded polynucleotide molecule comprising a nucleotide sequence that is the complement of a nucleotide sequence of one strand of any of the aforementioned nucleotide sequences. In a specific embodiment, the present invention provides aHSR1 ribonucleotide molecule comprising a nucleotide sequence (SEQ ID NO: 3) that is the complement of hamster Heat Shock RNA (HSR1) having SEQ ID NO: 1.

The present invention further provides an isolated polynucleotide molecule comprising a nucleotide sequence that is homologous to the nucleotide sequence of the HSR1 or the HSR1-encoding polynucleotide molecule of the invention or fragments thereof. In a specific embodiment, such polynucleotide molecule has at least 50% sequence identity, preferably at least 75% sequence identity, more preferably at least 90% sequence identity, and most preferably at least 95% sequence identity to the nucleotide sequence of the HSR1 or the HSR1-encoding polynucleotide molecule of the invention. Particularly useful HSR1 orthologs of the present invention are human, hamster, mouse, *Xenopus, Drosophila, Arabidopsis*, and yeast orthologs. In addition to the sequence homology, the preferred HSR1 orthologs of the present invention possess at least one of the same functional properties of the hamster HSR1 or human HSR1. Such properties include without limitation the ability to interact with eEF1A, the ability to interact with HSF, the ability to form a ternary complex with eEF1A and HSF, the ability to activate HSF DNA binding, the ability to undergo a conformational change in response to stress, etc.

The present invention further provides isolated polynucleotide and oligonucleotide molecules that hybridize to the HSR1 or the HSR1-encoding polynucleotide molecules of the invention under standard or high stringency hybridization conditions. The invention also provides several specific non-limiting examples of such polynucleotide and oligonucleotide molecules, including without limitation oligonucleotide molecules having SEQ ID NOS: 4-6, 9-12, and 17-19.

The HSR1-related nucleic acid molecules of the invention or the nucleic acid molecules comprising sequences that hybridize to them under standard hybridization conditions (including their homologs/orthologs, complementary sequences and various oligonucleotide probes and primers derived from them) can be used to modulate (e.g., inhibit or augment) a function of HSR1 or HSF/HSR1/eEF1A ternary complex (e.g., by modulating (i) interaction between HSR1 and eEF1A, (ii) interaction between HSR1 and HSF, (iii) formation of a ternary complex HSF/HSR1/eEF1A, (iv) activation of HSF DNA binding, (v) the ability of HSR1 to undergo a conformational change in response to stress, etc.). The HSR1-related nucleic acid molecules of the invention or the nucleic acid molecules comprising sequences that hybridize to them under standard hybridization conditions (including their homologs/orthologs, complementary sequences and various oligonucleotide probes and primers derived from them) can be also used to modulate (e.g., inhibit or activate)

expression of HSR1 genes (e.g., by inhibiting transcription, processing, transport, or by promoting degradation of corresponding RNAs). In a specific embodiment, the present invention provides HSR1-specific antisense oligonucleotides, RNA interference (RNAi) molecules, ribozymes, and triple helix forming oligonucleotides (TFOs) which can be effectively used to mediate any of these functions. The invention also provides specific non-limiting examples of HSR1-specific antisense oligonucleotides including without limitation molecules having nucleotide sequences selected from the group consisting of SEQ ID NO: 3 (aHSR1), SEQ ID NO: 9 ($1^{HSR1}$), SEQ ID NO: 10 ($2^{HSR1}$), SEQ ID NO: 11 ($5^{HSR1}$), and SEQ ID NO: 12 ($6^{HSR1}$). The invention also provides specific non-limiting examples of HSR1-specific RNAi molecules including without limitation siRNA molecules comprising SEQ ID NO: 7 (siHSR1-160) or SEQ ID NO: 20 (siHSR1-224).

In a related embodiment, the present invention provides recombinant vectors and host cells (both eukaryotic and prokaryotic) which have been genetically modified to express or overexpress various nucleotide molecules of the present invention. The present invention also provides a eukaryotic cell that has been genetically modified so that its normal expression of an HSR1-encoding gene has been reduced or eliminated. In another embodiment, the invention provides a eukaryotic cell that has been genetically modified so that its normal expression of an HSR1-encoding gene has been increased. In a preferred embodiment, such cells are mammalian cells. The invention also provides genetically modified animals (e.g., mammals) that comprise such cells.

In conjunction with the HSR1-specific antisense oligonucleotides, RNAi molecules, ribozymes, and TFOs, the present invention also provides a method for modulating (e.g., inhibiting or increasing) a stress response in a cell comprising administering said molecules to the cell. As specified herein, the modulation of the stress response in a cell can be detectable by various methods, including without limitation (i) detecting changes in the level of HSF1-mediated transcription and (ii) detecting changes in the level of a Heat Shock Protein (HSP). In a related embodiment, the invention provides a method of modulating (e.g., inhibiting or increasing) a stress tolerance in a cell comprising administering to the cell an antisense oligonucleotide or an RNAi molecule or a ribozyme or a TFO of the invention.

Another object of the present invention is to use the HSR1-specific antisense oligonucleotides, RNAi molecules, ribozymes, and TFOs of the invention as a basis for developing therapeutics to treat various diseases (e.g., cancer, inflammation, ischemia, reperfusion injury, neurodegenerative disorders, age-related diseases, HIV infection, deafness, and related disorders).

Accordingly, the present invention provides novel anti-cancer agents based on the HSR1-specific antisense oligonucleotides, RNAi molecules, ribozymes, and TFOs as well as methods for using such agents to treat cancer. The novel anti-cancer agents of the present invention can be used in conjunction with existing treatments to improve their effect by increasing the sensitivity of the cells to pro-apoptotic stimuli such as thermo-, chemo-, and radiotherapeutic treatments.

Thus, in one embodiment, the present invention provides a method for increasing sensitivity of a cancer cell to a treatment comprising administering to the cell an antisense oligonucleotide or an RNAi molecule or a ribozyme or a TFO that can specifically inhibit a function of an HSR1 or that can specifically inhibit expression of a gene encoding an HSR1. In a specific embodiment, the treatment can be selected from the group consisting of (without limitation) radiation treatment, chemical treatment, thermal treatment, and any combination thereof. In another embodiment, the invention provides a method for treating a cancer in a mammal comprising administering to the mammal an antisense oligonucleotide or an RNAi molecule or a ribozyme or a TFO that can specifically inhibit a function of an HSR1 of the invention or that can specifically inhibit expression of a gene encoding an HSR1 of the invention. In yet another embodiment, the invention provides a method for improving efficiency of an anti-cancer treatment in a mammal comprising administering to the mammal an antisense oligonucleotide or an RNAi molecule or a ribozyme or a TFO that can specifically inhibit a function of an HSR1 of the invention or that can specifically inhibit expression of a gene encoding an HSR1 of the invention. In a specific embodiment, the mammal is human. In another specific embodiment, the mammal is further subjected to a treatment selected (without limitation) from the group consisting of radiation therapy, chemotherapy, thermotherapy, and any combination thereof. The relative timing of antisense/RNAi/ribozyme/TFO administration and anti-cancer treatment would depend on the delivery mechanism for antisense/RNAi/ribozyme/TFO and on the type of the specific anti-cancer treatment used. Generally, cells may become more sensitive to an anti-cancer treatment as soon as one hour after antisense/RNAi/ribozyme/TFO administration.

The invention also provides a method for inhibiting/treating a disease in a mammal comprising administering to the mammal an antisense oligonucleotide or an RNAi molecule or a ribozyme or a TFO that can specifically augment a function of an HSR1 of the invention or that can specifically activate expression of a gene encoding an HSR1 of the invention. The diseases that can be inhibited/treated using such method include without limitation an inflammatory reaction, ischemia, reperfusion injury, HIV transcription, aging, age-related diseases, neurodegeneration (e.g., Alzheimer's disease, Parkinson's disease, amyotrophic lateral sclerosis (ALS), Huntington's disease, spinobulbar muscular atrophy, dentatorubral pallidoluysian atrophy, spinocerebellar ataxias, Kennedy disease, etc.), and deafness. In a specific embodiment, the mammal is human.

In another object, the present invention provides a method for identifying a candidate compound useful for modulating a function of an HSR1 of the invention and/or HSF/HSR1/eEF1A ternary complex, said method comprising:
(a) contacting a first cell with a test compound for a time period sufficient to allow the cell to respond to said contact with the test compound;
(b) determining in the cell prepared in step (a) the function of the HSR1 and/or HSF/HSR1/eEF1A ternary complex; and
(c) comparing the function of the HSR1 determined in step (b) to the function of the HSR1 and/or HSF/HSR1/eEF1A ternary complex in a second (control) cell that has not been contacted with the test compound;
wherein a detectable change in the HSR1 and/or HSF/HSR1/eEF1A ternary complex in the first cell in response to contact with the test compound compared to the function of the HSR1 and/or HSF/HSR1/eEF1A ternary complex in the second cell that has not been contacted with the test compound, indicates that the test compound modulates the function of the HSR1 and/or HSF/HSR1/eEF1A ternary complex and is a candidate compound.

As disclosed herein, a function of HSR1 and/or HSF/HSR1/eEF1A ternary complex assayed according to this method can be any function, e.g., stress/temperature-induced conformational change of HSR1, interaction of HSR1 with HSF, interaction of HSR1 with eEF1A, formation of HSF/

HSR1/eEF1A ternary complex, activation of HSF-mediated DNA binding, activation of HSP expression, thermotolerance, etc. The test compound can be without limitation a small inorganic molecule, a small organic molecule, a polypeptide, a nucleic acid molecule, or a chimera or derivative thereof. In one embodiment of this screening method, both test and control cells can be subjected to stress (e.g., heat shock). In this embodiment, the test compound can be added after cells had been subjected to stress, or after a preconditioning stress but before the lethal stress, or before cells had been subjected to stress.

In a separate embodiment, the present invention provides a method for identifying a candidate compound capable of binding to the HSR1 of the invention and/or HSF/HSR1/eEF1A ternary complex, said method comprising:
(a) contacting the HSR1 and/or HSF/HSR1/eEF1A ternary complex with a test compound under conditions that permit binding of the test compound to the HSR1 and/or HSF/HSR1/eEF1A ternary complex; and
(b) detecting binding of the test compound to the HSR1 and/or HSF/HSR1/eEF1A ternary complex.

The test compound can be without limitation a small inorganic molecule, a small organic molecule, a polypeptide, a nucleic acid molecule, or a chimera or derivative thereof. The binding of the test compound to the HSR1 and/or HSF1/HSR1/eEF1A ternary complex can be detected, e.g., by detecting HSF DNA binding in crude extracts, HSP expression, or cell thermotolerance. In a specific embodiment, the conditions that permit binding of the test compound to the HSR1 and/or to the HSF1/HSR1/eEF1A ternary complex are stress conditions (e.g., heat shock conditions).

The above-identified screening methods of the invention can be used to identify a candidate compound that can be used to treat a condition that can be treated by modulating a function of a eukaryotic HSR1 and/or HSF/HSR1/eEF1A ternary complex. Such conditions include without limitation cancer, inflammation, ischemia, reperfusion injury, neurodegeneration, age-related diseases, HIV infection, deafness, and related disorders.

Control lanes 1 and 2 show HSF1 EMSA in an extract from HS cells before and after incubation for 1 h at 37° C., respectively.

Figure 4:
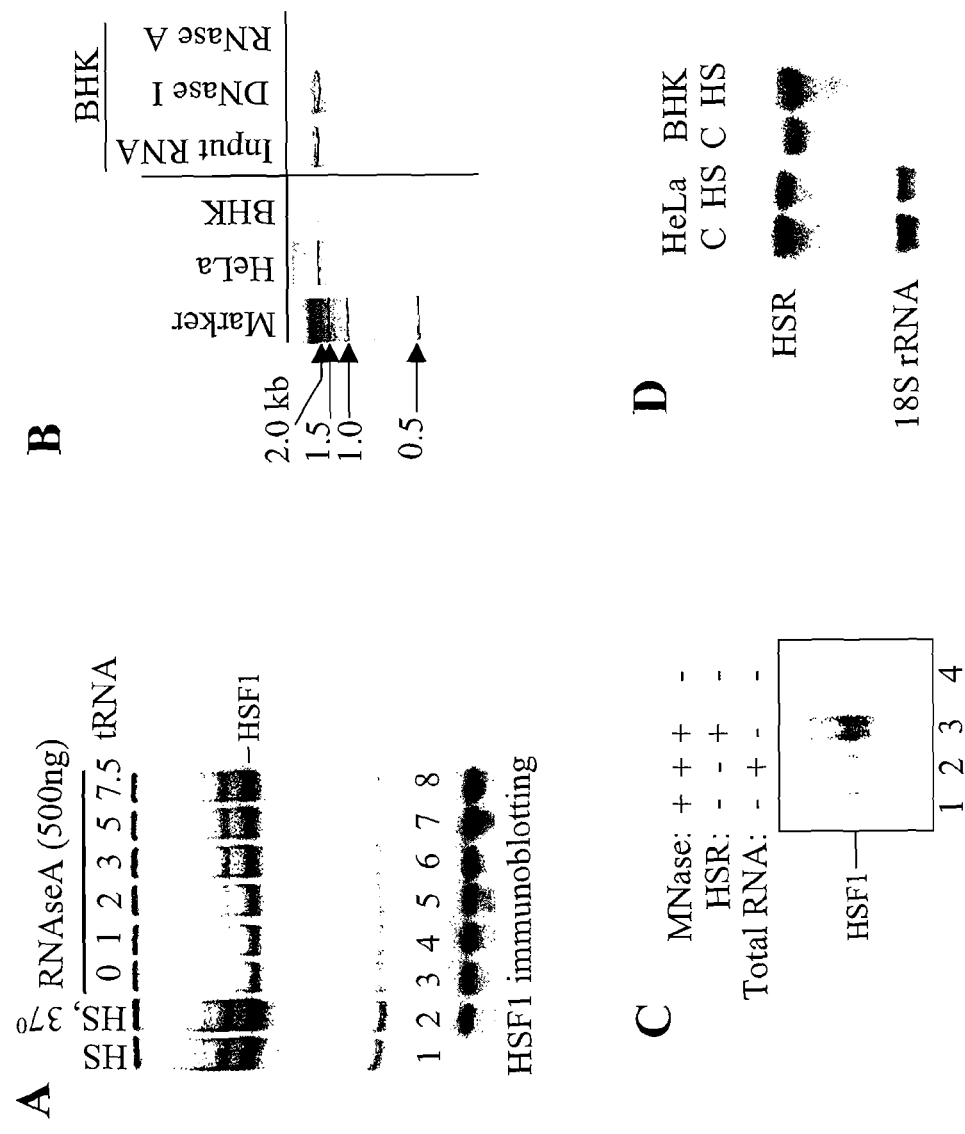
FIG. 4A represents electrophoretic gel mobility shift assays (EMSA) of in vitro induction of HSF1 DNA binding in a whole cell lysate (10 µg total protein) from heat shocked (HS, 1 h at 43° C.) BHK cells treated with RNase A (500 ng; for 1 h at 37° C.) in the presence of various concentrations of tRNA (ng). The amount of HSF1 in each lane was monitored by immunoblotting with anti-HSF1 antibodies (lower panel). The assay shows dependence of the HSF1 activation on RNA.

FIG. 4B represents denaturing 4% PAGE analysis of RNA (HSR1) isolated from the pooled HSF1-interacting (eEF1A containing) fractions from the lysate of heat shocked HeLa or BHK cells. Where indicated HSR1 samples were treated for 30 min at 25° C. with DNase I (10 U) or RNase A (100 ng) before loading onto the gel (right lanes). The gel was silver stained. The analysis shows that HSF1-interacting RNA (HSR1) migrating at about 2.5 kb on denaturing PAGE is sensitive to RNase A but not to DNase I.

FIG. 4C represents electrophoretic gel mobility shift assays (EMSA) of in vitro induction of HSF1 DNA binding by the whole cell lysate (20 µg) of heat shocked BHK cells which was first incubated with micrococcal nuclease (MNase), then, after reaction was stopped by addition of EGTA (lane 1), it was incubated with RNA (either HSR1 (lane 2) or total RNA (lane 3)) for 1 hour at room temperature. Lane 4: lysate of unstressed cells. The analysis demonstrates that HSR1 restored the DNA binding activity of HSF1 after it has been eliminated using micrococcal nuclease.

FIG. 4D represents Northern blot analysis of HSR1 expression in BHK and HeLa cells. Total RNA (10 µg) from either heat shocked (HS) or unstressed (C) BHK or HeLa cells was subjected to electrophoresis in a denaturing agarose gel, transferred to a membrane, and probed with [$^{32}$P]-labeled RNA probe corresponding to region 167-405 of HSR1. An 18S RNA probe was used for normalization purposes.

Figure 5:
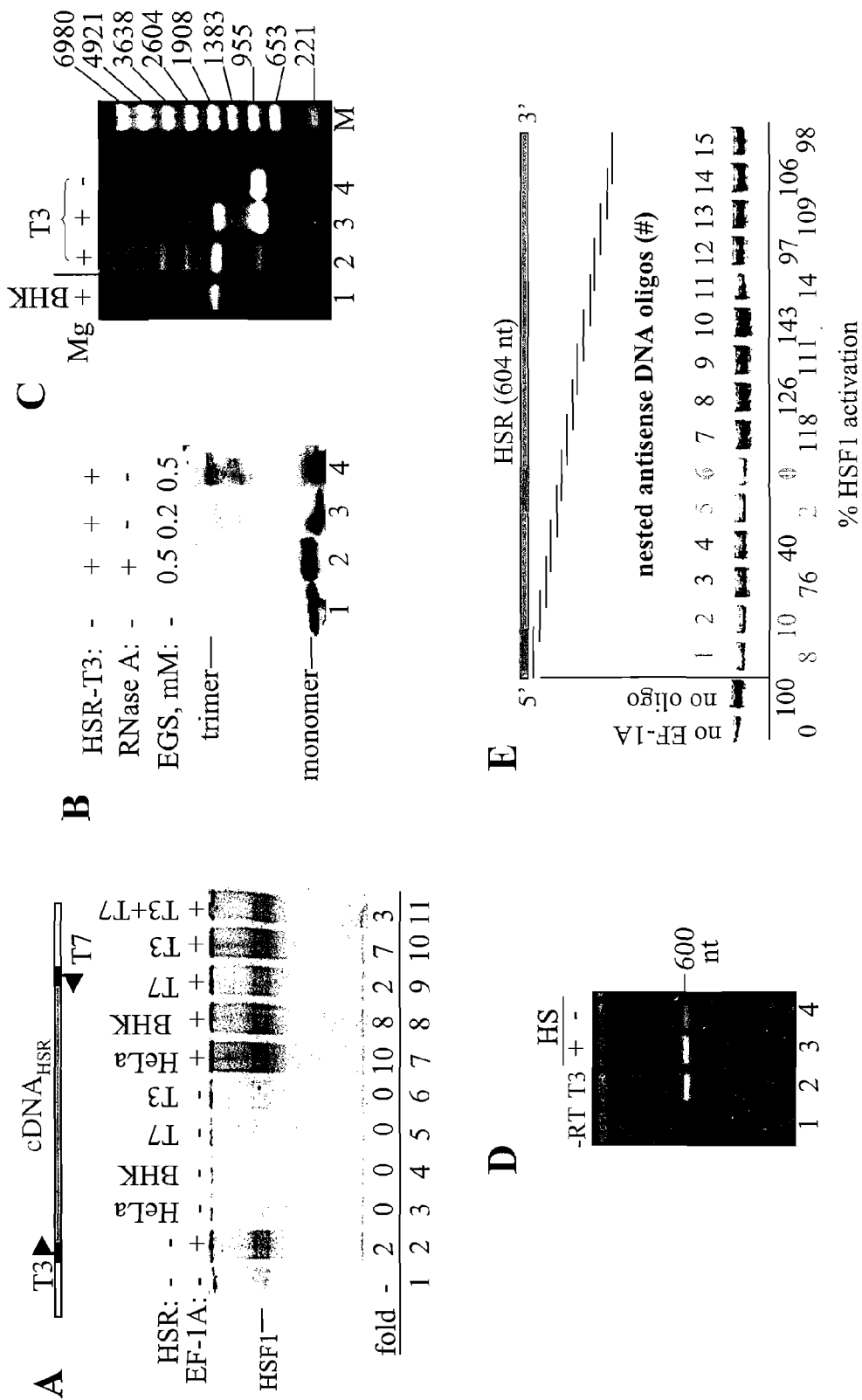

FIG. 5A demonstrates reconstitution of the HSF1 activating complex. Schematics on the top show HSR1 cDNA flanked with T7 and T3 promoters. The lower panel represents electrophoretic gel mobility shift assays (EMSA) of recombinant HSF1 incubated with pure eEF1A and HSR1 isolated either from HeLa or BHK activating fractions (lanes 7, 8) or either sense (T3) or antisense (T7) HSR1 synthesized by in vitro transcription (lanes 9-11). Quantitation of HSF1 activation is presented as the fold increase relative to a background control (lane 1). The analysis shows that both HSR1 from heat-shocked BHK or HeLa cells (lanes 7, 8) and sense in vitro synthesized HSR1-T3 (lane 10) activate HSF1 (lanes 7, 9, and 10: ~5% of the total HSF1 activated under these conditions) when added together with purified eEF1A, while neither component alone is capable of activating HSF1 (lanes 2-6).

FIG. 5B represents Western blotting analysis of HSF1 oligomerization during activation in vitro. Purified recombinant mouse HSF1 was incubated with eEF1A with (lanes 2-4) or without (lane 1) HSR1-T3 in the presence (lane 2) or absence (lanes 1, 3, 4) of RNase A, followed by cross-linking with indicated concentrations of EGS, SDS-PAGE, and immunoblotting using HSF1 8487 polyclonal antibody. The analysis shows that HSR1-T3-mediated HSF1 activation is accompanied by HSF1 trimerization.

FIG. 5C represents electrophoretic mobility analysis of endogenous HSR1 isolated from BHK cells or HSR1 synthesized by in vitro transcription. HSR1 isolated from BHK cells (lane 1) or synthesized by in vitro transcription (T3, lanes 2-4) was incubated in $Mg^{2+}$-free buffer (lanes 4) or in buffer containing 4 mM $Mg^2$ (lanes 1-3) and subjected to electrophoresis in an 1% agarose gel. Sample in lane 2 was heated at 43° C. prior to loading. M-RNA ladder.

FIG. 5D represents agarose gel analysis of RT-PCR products after HSR1 co-immunoprecipitation with an anti-eEF1A antibody (performed as described in the legend to FIG. 3A), followed by isolation of RNA from a precipitate prepared from HS (lane 3) or control (lane 4) cells and RT-PCR using HSR1-specific primers. Lane 1—no reverse transcription step. Lane 2—in vitro transcribed HSR1 (T3) was used in place of HSR1 isolated from the immunoprecipitate. The analysis demonstrates the formation of a molecular complex comprising HSR1 and eEF1A, which is more abundant in cells subjected to stress.

FIG. 5E represents mapping of the functional domains of HSR1 by electrophoretic gel mobility shift assays (EMSA). 15 overlapping 45-mer HSR1 antisense DNA oligos covering the entire length of HSR1 were screened for their ability to inhibit HSF1 activation in the reconstituted system. Recombinant HSF1 (<10 nM) was activated in the presence of pure eEF1A (0.01 mg/ml) and HSR1-T3 (0.4 µM). Where indicated, an antisense oligo was added to 10 µM. Changes in HSF1 activation were quantitated after setting the activity of HSF1 in the absence of oligo at 100% (lane 2) and without eEF1A at 0% (lane 1). Note that some oligos potentiate HSF1 activation (e.g., oligo #10). The analysis demonstrates that at least two domains in HSR1 (defined by oligos 1-2 and 5-6, respectively) are essential for HSF1 activation.

Figure 6:
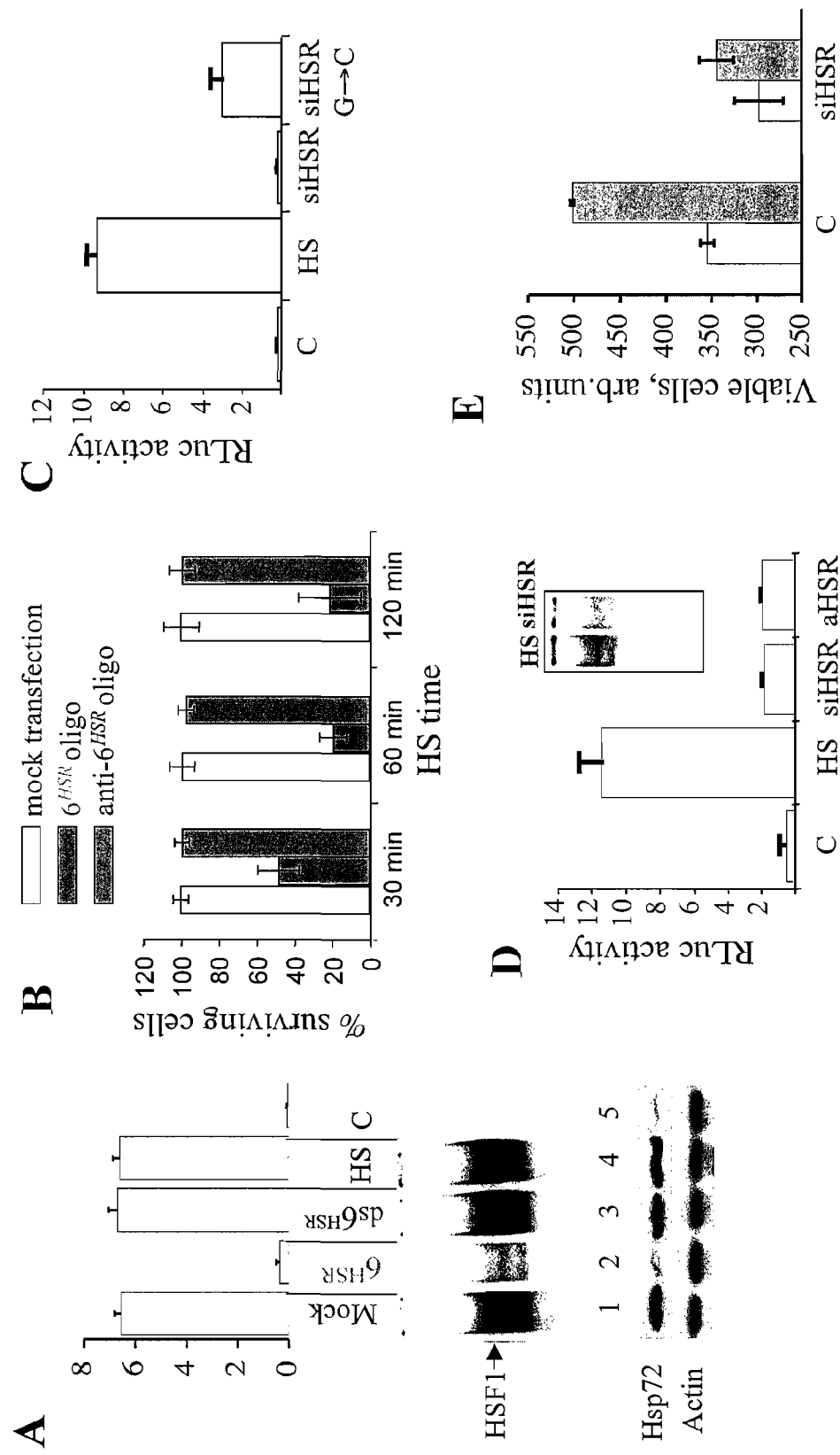

FIGS. 6 A-E demonstrate the effect of HSR1-specific antisense oligonucleotides/siRNA transfected into BHK or HeLa cells on heat shock response in vivo. A. Electrophoretic gel mobility shift assays (EMSA) of HSF1 DNA binding activity observed in the lysate of BHK cells after heat shock at 43° C. for 1 h in the presence of $6^{HSR1}$ HSR1 antisense oligonucleotide or various controls. BHK cells were transfected with 100 nM of either $6^{HSR1}$ antisense oligonucleotide (lane 2), an equal amount of the corresponding double-stranded oligo ($6^{HSR1}$/anti-$6^{HSR1}$, lane 3) or mock transfected (lane 1). Transfected cells were heat-shocked for 1 h at 43° C., a whole cell lysate was immediately prepared from half of the cells and 20 µg of the total protein was analyzed by EMSA for HSF1 activity. The other half of the transfected cells was allowed to recover at 37° C. for 16 h and a whole cell lysate was analyzed by immunoblotting using anti-HSP72 (inducible HSP70) antibody (lower panel). Control (lane 5)—lysate of unstressed cells. HS (lane 4)—lysate of untransfected heat shocked cells. Upper panel shows quantitation of EMSA data from 3 independent experiments. The analysis demonstrates that $6^{HSR1}$, but not $6^{HSR1}$/anti-$6^{HSR1}$, inhibits activation of HSF1 in vivo as well as the production of HSP72 in response to HS. B. Graph of BHK cell viability. Cells were transfected with 100 nM $6^{HSR1}$ or anti-$6^{HSR1}$, or mock transfected. Thermotolerance was induced by incubation for 1 h at 43° C. followed by 15 h recovery at 37° C. Lethal HS (45° C.) was performed for the indicated time periods. Cell viability was determined by MTS assay 16 h after lethal HS. The data for $6^{HSR1}$ and anti-$6^{HSR1}$ oligos were normalized to the efficiency of transfection. The data show that $6^{HSR1}$, but not $6^{HSR1}$/anti-$6^{HSR1}$, compromises cell survival after HS. C. Graph showing inhibition of HS promoter activation by HSR1-directed siRNA. RLuc activity was measured in lysates of BHK cells transiently transfected with a mixture of RLuc reporter plasmid, a β-gal internal control, and a siRNA construct expressing HSR1-directed siRNA (siHSR1) corresponding to the $6^{HSR1}$ antisense oligo or its mutant derivative (siHSR1: C→G). C-control lysate of unstressed cells. The data demonstrate that, while the RLuc activity was induced about 200-fold by HS treatment followed by recovery at 37° C., siHSR1 strongly inhibited the HS induction of RLuc. D. Graph showing inhibition of HS response in stably transfected cells expressing HSR1-directed siRNA (siHSR1). RLuc activity was measured in lysates of HeLa cells stably expressing GFP (HS), siHSR1 or antisense HSR1 (aHSR1) transiently transfected with a RLuc reporter plasmid and a β-gal internal control. C-lysate of unstressed cells. The HSF1 activity in the lysates of GFP (HS) and siHSR1 expressing cells is shown in the inset. The data demonstrate that cells expressing siHSR1 or aHSR1 (but not GFP) were deficient in their ability to induce RLuc activity after 2 h HS at 43° C. followed by overnight recovery at 37° C. E. Graph showing inhibition of thermotolerance by HSR1-directed siRNA (siHSR1). Cells stably expressing GFP or siHSR1 were subjected to lethal 2 h HS at 46° C. after being pre-conditioned by 1 h 43° C. HS where indicated. Cell viability was determined by the MTS-based assay. The data demonstrate that cells stably expressing siHSR1 failed to acquire thermotolerance after HS pre-conditioning. Taking together, the data in A-E show that HSR1 is essential for the HS response in mammalian cells.

FIGS. 7A-B are schematic representations of generation of derivatized HSR1 by "walking" with *E. coli* RNA polymerase without (A) or with (B) "roadblock". "Ni-NTA" stands for Ni-agarose beads.

DETAILED DESCRIPTION OF THE INVENTION

1. Definitions

Within the meaning of the present invention, when used in relation to a cell of a eukaryotic organism, the terms "stress" or "stressful conditions" refer to any condition that results in activation or increase of Heat Shock Factor (HSF)-mediated transcription or in activation or increase of the synthesis of at least one heat shock protein (HSP). Examples of stressful conditions include without limitation elevated temperature, oxidative stress (e.g. $H_2O_2$), alcohols, hyper- and hypoosmotic stress, heavy metals, amino acid analogs, viral infection, inflammation, and serum starvation (see also Morimoto, et al., In The Biology of Heat Shock Proteins and Molecular Chaperones, 1994 (New York: Cold Spring Harbor Press), pp. 417-455).

The terms "heat shock" or "HS" or "heat stress" is used to refer to stressful conditions associated with elevated temperature. Examples of heat shock conditions for different eukaryotic organisms include without limitation 40-43° C. for mammalian cells, 29-36° C. for *Drosophila cells* and *Xenopus* (normal growth 25° C.), 28° C. for salmon and trout, 40-45° C. for *Arabidopsis* and corn plants, and 39-40° C. for yeast.

The term "thermotolerance" is used herein to refer to a cellular adaptation caused by a single, severe but nonlethal heat exposure that allows a cell or organism to survive a subsequent and otherwise lethal heat stress.

The terms "heat shock protein" or "HSP" are used interchangeably to refer to a family of proteins involved in basic cellular processes under both stress and normal conditions such as correct folding of nascent polypeptides, binding to exposed hydrophobic regions of denatured or abnormal proteins to prevent their aggregation and promote degradation, and translocation of proteins into membrane-bound organelles in the cell (see, e.g., Mayer, et al., Adv. Protein Chem. 2001; 59:1-44; Jensen, et al., Curr. Biol. 1999; 9:R779-R782; Pilon, et al., Cell 1999; 97:679-682; Ryan, et al., Adv. Protein Chem. 2001; 59:223-242; Zylicz, et al., IUBMB. Life 2001; 51:283-287). HSPs are classified into several groups based on their molecular weight and include without limitation HSP70, HSP60, HSP40, HSP90, HSP100, and small HSPs such as HSP27.

As used herein, the terms "heat shock factor" or "HSF" refer to a family of transcription factors which are involved in stress-inducible gene expression. Whereas only one HSF is present in yeast, *Drosophila*, and *C. elegans* (Wu, Ann. Rev. Cell Dev. Biol. 1995; 11:441-469), in mammalian cells, three HSFs (HSF1, HSF2, and HSF4) have been characterized (Morimoto, et al., Genes Dev. 1998; 12:3788-3796). HSF1 is constitutively expressed and plays the principal role in the stress-induced expression of HSPs.

In the context of the present invention, the term "augment" means enhancing or extending the duration of a function, or both. In relation to a function of a Heat Shock RNA (HSR1) molecule, the term "augment" refers without limitation to the ability to enhance interaction with HSF or eEF1A or both, or enhance HSF binding to DNA, or enhance the HSF-mediated transcription, to extend the duration of the HSF-mediated transcriptional activation.

Within the meaning of the present invention, the term "inhibit" is used to refer to any level of reduction in a function or amount of a molecule. For example, when used in relation to HSF activation, the term "inhibit" may mean without limitation reduction in the formation or function of HSF/HSR1/eEF1A ternary complex, reduction in HSF nuclear transport, reduction in HSF DNA binding, reduction in interaction with any of the elements of the transcriptional machinery, etc. When used in relation to a function of a Heat Shock RNA (HSR1) molecule, the term "inhibit" may mean without limitation reduction in the conformational change in HSR1 in response to stress, reduction in interaction of HSR1 with HSF and/or eEF1A, reduction in the formation or function of HSF/HSR1/eEF1A ternary complex, reduction in HSR1 nuclear transport, etc.

The phrase "increasing sensitivity of a cancer cell to a treatment" is used herein to refer to any detectable decrease in propagation and/or survival of a cancer cell subjected to a given treatment.

The term "age-related disease" is used in the present invention to encompass all types of diseases associated with normal as well as premature cellular and organism aging, including without limitation atherosclerosis and neurodegenerative diseases such as Alzheimer's disease and Parkinson's disease.

The terms "polynucleotide" or "nucleotide sequence" mean a series of nucleotide bases (also called "nucleotides") in DNA and RNA, and mean any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'-and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "express" and "expression" mean allowing or causing the information in a gene or DNA sequence to become manifest, for example, producing an non-coding (untranslated) RNA or a protein by activating the cellular functions involved in transcription and translation of a corresponding gene or DNA sequence. A DNA sequence is expressed in or by a cell to form an "expression product" such as RNA or a protein. The expression product itself, e.g. the resulting RNA or protein, may also be said to be "expressed" by the cell.

The terms "vector", "cloning vector" and "expression vector" mean the vehicle by which a DNA or RNA sequence can be introduced into a host cell, so as to transform the host and clone the vector or promote expression of the introduced sequence. Vectors include plasmids, cosmids, phages, viruses, etc. Vectors may further comprise selectable markers.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described infra.

As used herein, the term "oligonucleotide" refers to a nucleic acid, generally of at least 8, preferably no more than 100 nucleotides, that is hybridizable to a genomic DNA molecule, a cDNA molecule, or an RNA molecule. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides can be used as PCR primers, either for cloning or for detection of a specific nucleic acid. In a further embodiment, an oligonucleotide of the invention can be used as antisense oligonucleotides to inhibit a function or expression of a nucleic acid molecule (see below). Generally, oligonucleotides are prepared synthetically, preferably on a nucleic acid synthesizer. Accordingly, oligonucleotides can be prepared with non-naturally occurring phosphoester analog bonds, such as thioester bonds, etc.

A sequence "encoding" an expression product, such as an RNA, polypeptide, protein, or enzyme, is a minimum nucleotide sequence that, when expressed, results in the production of that RNA, polypeptide, protein, or enzyme.

As used herein, the term "gene" means a DNA sequence that codes for a particular non-coding (untranslated) RNA or a sequence of amino acids, which comprise all or part of one or more proteins or enzymes, and may include regulatory (non-transcribed) DNA sequences, such as promoter sequences, which determine for example the conditions under which the gene is expressed.

The term "antisense" nucleic acid molecule or oligonucleotide is used in the present disclosure to refer to a single stranded (ss) nucleic acid molecule, which may be DNA, RNA, a DNA-RNA chimera, or a derivative thereof, which, upon hybridizing under physiological conditions with complementary bases in an RNA or DNA molecule of interest, inhibits or activates (in the case of "activating antisense oligonucleotides") the expression of the corresponding gene by modulating, e.g., RNA transcription, RNA processing, RNA transport, mRNA translation, or RNA stability. As presently used, "antisense" broadly includes RNA-RNA interactions, RNA-DNA interactions, and RNase-H mediated arrest. Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607). According to the present invention, the function(s) of HSR1 in a cellular stress response may be identified, modulated and studied using antisense nucleic acids derived on the basis of HSR1 nucleic acid molecules of the invention. Furthermore, as disclosed herein, due to their ability to modulate (inhibit or augment) HSR1 function(s), HSR1-specific antisense oligonucleotides may be useful as therapeutics to treat cancer, inflammation, ischemia, neurodegeneration, age-related diseases, HIV infection, deafness, and related disorders.

Specific examples of synthetic antisense oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 1991; 254:1497). Other synthetic oligonucleotides may contain substituted sugar moieties comprising one of the following at the 2' position: OH, SH, $SCH_3$, F, OCN, O($CH_2$)$_n$$NH_2$ or O($CH_2$)$_n$$CH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine. In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability. LNA allows the use of very short oligonucleotides (less than 10 bp) for efficient hybridization in vivo.

The term "RNA interference" or "RNAi" refers to the ability of double stranded RNA (dsRNA) to suppress the expression of a specific gene of interest in a homology-dependent manner. It is currently believed that RNA interference acts post-transcriptionally by targeting RNA molecules for degradation. RNA interference commonly involves the use of dsRNAs that are greater than 500 bp; however, it can also be mediated through small interfering RNAs (siRNAs) or small hairpin RNAs (shRNAs), which can be 10 or more nucleotides in length and are typically 18 or more nucleotides in length. For reviews, see Bosner and Labouesse, Nature Cell Biol. 2000; 2:E31-E36 and Sharp and Zamore, Science 2000; 287:2431-2433.

As used herein, the term "triplex-forming oligonucleotide" or "triple helix forming oligonucleotide" or "TFO" refers to molecules that bind in the major groove of duplex DNA and by so doing produce triplex structures. TFOs bind to the purine-rich strand of the duplex through Hoogsteen or reverse Hoogsteen hydrogen bonding. They exist in two sequence motifs, either pyrimidine or purine. According to the present invention, TFOs can be employed as an alternative to antisense oligonucleotides and can be both inhibitory and stimulatory. TFOs have also been shown to produce mutagenic events, even in the absence of tethered mutagens. TFOs can increase rates of recombination between homologous sequences in close proximity. TFOs of the present invention may be conjugated to active molecules. (for review see Casey and Glazer, Prog. Nucleic Acid. Res. Mol. Biol. 2001; 67:163-92)

The term "ribozyme" is used herein to refer to a catalytic RNA molecule capable of mediating catalytic reactions on (e.g., cleaving) RNA substrates. Ribozyme specificity is dependent on complementary RNA-RNA interactions (for a review, see Cech and Bass, Annu. Rev. Biochem. 1986; 55:599-629). Two types of ribozymes, hammerhead and hairpin, have been described. Each has a structurally distinct catalytic center. The present invention contemplates the use of ribozymes designed on the basis of the HSR1 or HSR1-encoding nucleic acid molecules of the invention to induce catalytic reaction (e.g., cleavage) of the HSR1, thereby modulating (e.g., inhibiting) a function or expression of HSR1. Ribozyme technology is described further in Intracellular Ribozyme Applications: Principals and Protocols, Rossi and Couture ed., Horizon Scientific Press, 1999.

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3).

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

Nucleic acid molecules that "hybridize" to any of the HSR1-encoding nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular HSR1 or HSR1-encoding nucleic acid.

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., Cell 1987; 50:667). Such nucleic acid molecules or proteins have sequence homology, as reflected by their sequence similarity, whether in terms of substantial percent similarity or the presence of specific residues or motifs at conserved positions.

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990; 87:2264, modified as in Karlin and Altschul, Proc. Natl. Acad. Sci. USA 1993; 90:5873-5877. Such an algorithm is incorporated into the NBLAST and XBLAST programs of Altschul et al., J. Mol. Biol. 1990; 215:403. BLAST nucleotide searches can be performed with the NBLAST program, score=100, word length=12, to obtain nucleotide sequences homologous to sequences of the invention. BLAST protein searches can be performed with the XBLAST program, score=50, word length=3, to obtain amino acid sequences homologous to protein sequences of the invention. To obtain gapped alignments for comparison purposes, Gapped BLAST can be utilized as described in Altschul et al., Nucleic Acids Res. 1997; 25:3389. Alternatively, PSI-Blast can be used to perform an iterated search that detects distant relationship between molecules. See Altschul et al. (1997), supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, CABIOS 1988; 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In addition to the hamster HSR1 cloned from BHK cells (SEQ ID NO: 1) and human HSR1 cloned from HeLa cells (SEQ ID NO: 2) (which is different from SEQ ID NO: 1 in only 4 positions), the present invention further provides polynucleotide molecules comprising nucleotide sequences having certain percentage sequence identities to SEQ ID NO: 1 or SEQ ID NO: 2. Such sequences preferably hybridize under conditions of moderate or high stringency as described above, and may include species orthologs.

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity.

The present invention encompasses all orthologs of HSR1. In addition to human, hamster and mouse orthologs, particularly useful HSR1 orthologs of the present invention are *Drosophila, Xenopus, Arabidopsis*, and yeast orthologs.

The term "modulator" refers to a compound that differentially affects the expression or activity of a gene or gene product (e.g., RNA molecule or protein), for example, in response to a stimulus (e.g., stress) that normally activates or represses the expression or activity of that gene or gene product when compared to the expression or activity of the gene or gene product not contacted with the stimulus. In one embodiment, the gene or gene product the expression or activity of which is being modulated includes a eukaryotic HSR1 or a gene or cDNA molecule that encodes a eukaryotic HSR1. Examples of modulators of the HSR1 or HSR1-encoding nucleic acids of the present invention include without limitation antisense nucleic acids, ribozymes, triple helix forming oligonucleotides (TFOs), and RNAi oligonucleotides.

A "test compound" is a molecule that can be tested for its ability to act as a modulator of a gene or gene product. Test compounds can be selected without limitation from small inorganic and organic molecules (i.e., those molecules of less than about 2 kDa, and more preferably less than about 1 kDa in molecular weight), polypeptides (including native ligands, antibodies, antibody fragments, and other immunospecific molecules), oligonucleotides, polynucleotide molecules, and derivatives thereof. In various embodiments of the present invention, a test compound is tested for its ability to modulate a function of HSR1 or modulate expression of HSR1. A compound that modulates a nucleic acid or protein of interest is designated herein as a "candidate compound" or "lead compound" suitable for further testing and development. Candidate compounds include, but are not necessarily limited to, the functional categories of agonist and antagonist.

An "agonist" is defined herein as a compound that interacts with (e.g., binds to) a nucleic acid molecule or protein, and promotes, enhances, stimulates or potentiates the expression or function of the nucleic acid molecule or protein. The term "partial agonist" is used to refer to an agonist which interacts with a nucleic acid molecule or protein, but promotes only partial function of the nucleic acid molecule or protein. A partial agonist may also inhibit certain functions of the nucleic acid molecule or protein with which it interacts. An "antagonist" interacts with (e.g., binds to) and inhibits or reduces the biological expression or function of the nucleic acid molecule or protein.

The term "detectable change" as used herein in relation to a function or expression level of a gene or gene product (e.g., HSR1) means any statistically significant change and preferably at least a 1.5-fold change as measured by any available technique such as electrophoretic gel mobility shift assays (EMSA), denaturing (8M urea) PAGE analysis, SDS-PAGE, Western blotting, nucleic acid hybridization, quantitative PCR, etc.

As used herein, the term "isolated" means that the material being referred to has been removed from the environment in which it is naturally found, and is characterized to a sufficient degree to establish that it is present in a particular sample. Such characterization can be achieved by any standard technique, such as, e.g., sequencing, hybridization, immunoassay, functional assay, expression, size determination, or the like. Thus, a biological material can be "isolated" if it is free of cellular components, i.e., components of the cells in which the material is found or produced in nature. A nucleic acid molecule excised from the chromosome that it is naturally a part of is considered to be isolated. Such a nucleic acid molecule may or may not remain joined to regulatory, or non-regulatory, or non-coding regions, or to other regions located upstream or downstream of the gene when found in the chromosome. Nucleic acid molecules that have been spliced into vectors such as plasmids, cosmids, artificial chromosomes, phages and the like are considered isolated. In a particular embodiment, a HSR1-encoding nucleic acid spliced into a recombinant vector, and/or transformed into a host cell, is considered to be "isolated".

Isolated nucleic acid molecules and isolated polynucleotide molecules of the present invention do not encompass uncharacterized clones in man-made genomic or cDNA libraries.

A protein that is associated with other proteins and/or nucleic acids with which it is associated in an intact cell, or with cellular membranes if it is a membrane-associated protein, is considered isolated if it has otherwise been removed from the environment in which it is naturally found and is characterized to a sufficient degree to establish that it is present in a particular sample. A protein expressed from a recombinant vector in a host cell, particularly in a cell in which the protein is not naturally expressed, is also regarded as isolated.

An isolated organelle, cell, or tissue is one that has been removed from the anatomical site (cell, tissue or organism) in which it is found in the source organism.

An isolated material may or may not be "purified". The term "purified" as used herein refers to a material (e.g., a nucleic acid molecule or a protein) that has been isolated under conditions that detectably reduce or eliminate the presence of other contaminating materials. Contaminants may or may not include native materials from which the purified material has been obtained. A purified material preferably contains less than about 90%, less than about 75%, less than about 50%, less than about 25%, less than about 10%, less than about 5%, or less than about 2% by weight of other components with which it was originally associated.

Methods for purification are well-known in the art. For example, nucleic acids or polynucleotide molecules can be purified by precipitation, chromatography (e.g., by affinity chromatography, preparative solid phase chromatography, oligonucleotide hybridization, and triple helix chromatography), ultracentrifugation, and other means. Polypeptides can be purified by various methods including, without limitation, preparative disc-gel electrophoresis, isoelectric focusing, HPLC, reverse-phase HPLC, gel filtration, affinity chromatography, ion exchange and partition chromatography, precipitation and salting-out chromatography, extraction, and counter-current distribution. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. The term "substantially pure" indicates the highest degree of purity that can be achieved using conventional purification techniques currently known in the art. In the context of analytical testing of the material, "substantially free" means that contaminants, if present, are below the limits of detection using current techniques, or are detected at levels that are low enough to be acceptable for use in the relevant art, for example, no more than about 2-5% (w/w). Accordingly, with respect to the purified material, the term "substantially pure" or "substantially free" means that the purified material being referred to is present in a composition where it represents 95% (w/w) or more of the weight of that composition. Purity can be evaluated by chromatography, gel electrophoresis, immunoassay, composition analysis, biological assay, or any other appropriate method known in the art.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. For example, in relation to cancer, the term "treat" may mean to relieve or alleviate at least one symptom selected from the group consisting of tumor growth, metastasis, sensitivity of tumor cells to treatments such as chemotherapy, radiation therapy, thermotherapy, etc. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject. Within the meaning of the present invention, disease conditions include without limitation various cancers, inflammation, ischemia/reperfusion injury, neurodegenerative disorders, age-related diseases, deafness, and HIV infection.

As used herein the term "therapeutically effective" applied to dose or amount refers to that quantity of a compound or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a cancer, inflammation, ischemia, neurodegenerative disorders, age-related diseases, HIV infection, deafness, or related disorder. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "genetically modified animal" encompasses all animals into which an exogenous genetic material has been introduced and/or whose endogenous genetic material has been manipulated. Examples of genetically modified animals include without limitation transgenic animals, e.g., "knock-in" animals with the endogenous gene substituted with a heterologous gene or an ortholog from another species or a mutated gene, "knockout" animals with the endogenous gene partially or completely inactivated, or transgenic animals expressing a mutated gene or overexpressing a wild-type or mutated gene (e.g., upon targeted or random integration into the genome) and animals containing cells harboring a non-integrated nucleic acid construct (e.g., viral-based vector, antisense oligonucleotide, shRNA, siRNA, ribozyme, etc.), including animals wherein the expression of an endogenous gene has been modulated (e.g., increased or decreased) due to the presence of such construct.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

2. Novel Ternary Ribonucleoprotein Complex of the Invention

As specified in the Background Section, supra, heat shock transcription factor HSF (HSF1 in mammalian cells) plays a central role in activation of the heat shock (HS) response in eukaryotic cells. HSF1 is present in unstressed cells in an inactive monomeric form and becomes activated by heat and other stress stimuli. HSF1 activation involves trimerization and acquisition of a site-specific DNA-binding activity.

As provided for the first time in the present invention, HSF activation by heat shock is mediated by a ribonucleoprotein complex comprising translation elongation factor eEF1A and a novel RNA termed herein "Heat Shock RNA" or "HSR1". Also provided herein are novel functional sequences of hamster HSR1 cloned from BHK cells (SEQ ID NO: 1) and human HSR1 cloned from HeLa cells (SEQ ID NO: 2), which reveal high degree of homology, with only 4 nucleotides being different. HSR1 is constitutively expressed in human and rodent cells, and its homologs are functionally interchangeable. HSR1 and eEF1A are both required for activation of HSF and constitute a minimal functional HSR1 activating complex. Indeed, as disclosed in the Examples Section, infra, in in vitro reconstituted system, RNA transcribed in vitro from the cloned HSR1 can restore activation of purified HSF1 by the purified eEF1A. Neither eEF1A nor in vitro transcribed HSR1 alone are capable of activating HSF1. However, when both components are added to HSF1 simultaneously, they induce HSF1 binding to DNA. HSF1 activation by eEF1A and HSR1 is accompanied by trimerization of the factor (see Examples, infra).

3. Novel Nucleic Acids of the Invention

The present invention provides an isolated ribonucleotide molecule comprising a eukaryotic Heat Shock RNA (HSR1) sequence or a fragment thereof. The invention also provides an isolated polynucleotide molecule encoding a eukaryotic HSR1 or a fragment thereof. In one embodiment, the invention provides isolated polynucleotide molecules comprising HSR1 sequences from mammalian cells (e.g., human [e.g., HeLa], hamster [e.g., BHK], mouse), *Drosophila* cells (e.g., Kc cells), *Xenopus* cells (e.g., *Xenopus laevis*), *Arabidopsis* cells (e.g., *Arabidopsis thaliana*), and yeast (e.g., *Saccharomyces cerevisiae*) as well as polynucleotide molecules comprising nucleotide sequences encoding such HSR1s. In one embodiment, the present invention provides an isolated ribonucleotide molecule comprising hamster Heat Shock RNA (HSR1) having SEQ ID NO: 1. In another embodiment, the present invention provides an isolated ribonucleotide molecule comprising human Heat Shock RNA (HSR1) having SEQ ID NO: 2. The invention also provides an isolated single-stranded polynucleotide molecule comprising a nucleotide sequence that is the complement of a nucleotide sequence of one strand of any of the aforementioned nucleotide sequences. In a specific embodiment, the present invention provides aHSR1 ribonucleotide molecule comprising a nucleotide sequence (SEQ ID NO: 3) that is the complement of the cloned hamster Heat Shock RNA (HSR1) having SEQ ID NO: 1.

The present invention further provides an isolated polynucleotide molecule comprising a nucleotide sequence that hybridizes under standard hybridization conditions to the ribonucleotide molecule (or a complement thereof) comprising a eukaryotic Heat Shock RNA (HSR1) sequence or a fragment thereof. The invention also provides an isolated polynucleotide molecule comprising a nucleotide sequence that hybridizes under standard hybridization conditions to the polynucleotide molecule (or a complement thereof) encoding a eukaryotic HSR1 or a fragment thereof. As specified in the Definitions Section, supra, examples of standard hybridization conditions include without limitation (i) an aqueous solution of 2×SSC (where 1×SSC is 0.15 M NaCl, 0.15 M Na citrate) at 55° C. or 65° C. or (ii) hybridization to filter-bound DNA in 0.5 M NaHPO$_4$, 7% SDS, 1 mM EDTA at 65° C. followed by washing in 0.2×SSC/0.1% SDS at 42° C., etc. In a preferred embodiment, the homologous polynucleotide molecule hybridizes to the polynucleotide molecule comprising a nucleotide sequence of a eukaryotic HSR1 or a sequence that encodes a eukaryotic HSR1 or a fragment thereof under highly stringent conditions, such as, for example, (i) in an aqueous solution of 0.5×SSC at 65° C.; (ii) hybridization to filter-bound DNA in 0.5 M NaHPO$_4$, 7% SDS, 1 mM EDTA at 65° C. followed by washing in 0.1.×SSC/0.1% SDS at 68° C.; or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)) (see the Definitions Section, above). In a specific embodiment, the homologous polynucleotide molecule hybridizes under highly stringent conditions to the polynucleotide molecule (or a complement thereof) comprising a nucleotide sequence SEQ ID NO: 1 or SEQ ID NO: 2 or a fragment thereof.

The present invention further provides an isolated polynucleotide molecule comprising a nucleotide sequence that is homologous to the nucleotide sequence of the HSR1 or the HSR1-encoding polynucleotide molecule of the present invention. In a specific embodiment, such polynucleotide molecule has at least 50% sequence identity, preferably at least 75% sequence identity, more preferably at least 90% sequence identity, and most preferably at least 95% sequence identity to the nucleotide sequence of the HSR1 or the HSR1-encoding polynucleotide molecule of the present invention (e.g., as determined by a sequence comparison algorithm selected from BLAST, FASTA, DNA Strider, and GCG, and preferably as determined by the BLAST program from the National Center for Biotechnology Information (NCBI-Version 2.2), available on the WorldWideWeb at ncbi.nlm.nih.gov/BLAST/).

Also encompassed by the present invention are orthologs of the specifically disclosed hamster and human HSR1 nucleic acids. Additional HSR1 orthologs can be identified based on the sequences of hamster and human orthologs disclosed herein, using standard sequence comparison algorithms such as BLAST, FASTA, DNA Strider, GCG, etc. Particularly useful HSR1 orthologs of the present invention are human, hamster, mouse, *Xenopus, Drosophila, Arabidopsis*, and yeast orthologs. In addition to sequence homology, the HSR1 orthologs of the present invention possess at least one of the same functional properties of the hamster HSR1 or human HSR1 disclosed in the Examples Section, infra. Such properties include without limitation the ability to interact with eEF1A, the ability to interact with HSF, the ability to form a ternary complex with eEF1A and HSF, the ability to activate HSF DNA binding, the ability to undergo a conformational change in response to stress, etc.

As disclosed above, the present invention provides polynucleotide molecules consisting of nucleotide sequences that are fragments of the nucleotide sequence of any of the aforementioned HSR1-related polynucleotide molecules of the present invention, or the complements of such nucleotide sequences. Such fragments comprise at least about 5%, at least about 10%, at least about 20%, at least about 30%, at least about 40%, at least about 50%, at least about 60%, at least about 70%, at least about 80%, at least about 90%, at least about 95%, or at least about 99% of the contiguous nucleotide sequence of the HSR1-related polynucleotide molecules of the present invention, or the complements of such nucleotide sequences. Such fragments can be used for a variety of purposes including, e.g., to produce a portion of an HSR1 in an appropriate expression system to identify functional or structural domains of HSR1, to use it to inhibit HSR1 function (see the disclosure of antisense technology, infra), to prepare a hybridization probe, etc.

In addition to the nucleotide sequences of any of the aforementioned HSR1-related polynucleotide molecules, polynucleotide molecules of the present invention can further comprise, or alternatively may consist of, nucleotide sequences selected from those sequences that naturally flank an HSR1-encoding nucleotide sequence in the chromosome, including regulatory sequences.

The polynucleotide molecules encompassed by the present invention exclude uncharacterized clones in man-made genomic or cDNA libraries.

4. Oligonucleotides of the Invention

The present invention further provides an oligonucleotide molecule that hybridizes to a polynucleotide molecule of the present invention, or that hybridizes to a polynucleotide molecule having a nucleotide sequence that is the complement of a nucleotide sequence of a polynucleotide molecule of the present invention. Such an oligonucleotide molecule: (i) is about 10 nucleotides to about 200 nucleotides in length, preferably from about 15 to about 100 nucleotides in length, and more preferably about 20 to about 50 nucleotides in length, and (ii) hybridizes to one or more of the polynucleotide molecules of the present invention under highly stringent conditions (e.g., washing in 6×SSC/0.5% sodium pyrophosphate at about 37° C. for about 14-base oligos, at about 48° C. for about 17-base oligos, at about 55° C. for about 20-base oligos, and at about 60° C. for about 23-base oligos). In one embodiment, an oligonucleotide molecule of the present invention is 100% complementary over its entire length to a portion of at least one of the aforementioned polynucleotide molecules of the present invention. In another embodiment, an oligonucleotide molecule of the present invention is greater than 90% complementary over its entire length to a portion of at least one of the aforementioned polynucleotide molecules of the present invention.

Specific non-limiting examples of oligonucleotide molecules according to the present invention include oligonucleotide molecules selected from the group consisting of SEQ ID NOS: 4-14 (see Examples Section, infra).

Oligonucleotide molecules of the present invention are useful for a variety of purposes, including, e.g., as hybridization probes for detection or as PCR primers for amplification or detection of HSR1-related polynucleotide molecules of the invention. Such oligonucleotide molecules can be labeled, e.g., with radioactive labels (e.g., $\gamma^{32}P$), biotin, fluorescent labels, etc. In one embodiment, a labeled oligonucleotide molecule can be used as a probe to detect the presence of a nucleic acid. For example, as disclosed in the Examples Section, infra, the invention provides a ribonucleotide (SEQ ID NO: 4) which hybridizes to region 167-405 of cloned hamster or human HSR1 and which can be used, e.g., as a Northern hybridization probe. In another embodiment, two oligonucleotide molecules (one or both of which may be labeled) can be used as PCR primers, either for cloning a full-length nucleic acid or a fragment of a nucleic acid encoding a gene product of interest, or to detect the presence of nucleic acids encoding a gene product. For example, as disclosed in the Examples Section, infra, the invention provides HSR1-specific PCR primers (SEQ ID NOS: 5-6 and 17-19) that can be used for RT-PCR of hamster and human HSR1. Methods for conducting amplifications, such as the polymerase chain reaction (PCR), are described, among other places, in Saiki et al., Science 1988; 239:487 and U.S. Pat. No. 4,683,202. Other amplification techniques known in the art, e.g., the ligase chain reaction, can alternatively be used (see, e.g., U.S. Pat. Nos. 6,335,184 and 6,027,923; Reyes et al., Clinical Chemistry 2001; 47:131-40; and Wu et al., Genomics 1989; 4:560-569).

The oligonucleotide molecules of the invention are also useful as antisense or short interfering (siRNA) or small hairpin (shRNA) RNA molecules or triple helix forming oligonucleotides (TFOs) capable of modulating function or expression of HSR1 molecules of the invention (see below). Generally, oligonucleotide molecules are prepared synthetically, preferably on a nucleic acid synthesizer, and may be prepared with non-naturally occurring phosphoester analog bonds, such as thioester bonds, where appropriate.

5. Recombinant Expression Systems a. Cloning and Expression Vectors

The present invention further provides compositions and constructs for cloning and expressing any of the polynucleotide molecules of the present invention, including cloning vectors, expression vectors, transformed host cells comprising any of said vectors, and novel strains or cell lines derived therefrom. In one embodiment, the present invention provides a recombinant vector comprising a polynucleotide molecule having a nucleotide sequence encoding a eukaryotic HSR1 molecule. In a specific embodiment, the HSR1 molecule comprises the amino acid sequence of SEQ ID NO: 1 or SEQ ID NO: 2.

Recombinant vectors of the present invention, particularly expression vectors, are preferably constructed so that the coding sequence for the polynucleotide molecule of the present invention is in operative association with one or more regulatory elements necessary for transcription of the coding sequence to produce an HSR1. As used herein, the term "regulatory element" includes but is not limited to nucleotide sequences that encode inducible and non-inducible promoters, enhancers, operators and other elements known in the art that serve to drive and/or regulate expression of polynucleotide coding sequences.

Methods are known in the art for constructing recombinant vectors containing particular coding sequences in operative association with appropriate regulatory elements, and these can be used to practice the present invention. These methods include in vitro recombinant techniques, synthetic techniques, and in vivo genetic recombination. See, e.g., the techniques described in Ausubel et al., 1989, above; Sambrook et al., 1989, above; Saiki et al., 1988, above; Reyes et al., 2001, above; Wu et al., 1989, above; U.S. Pat. Nos. 4,683,202; 6,335,184 and 6,027,923.

A variety of expression vectors are known in the art that can be utilized to express a polynucleotide molecule of the present invention, including recombinant bacteriophage DNA, plasmid DNA, and cosmid DNA expression vectors containing the particular coding sequences. Typical prokaryotic expression vector plasmids that can be engineered to contain a polynucleotide molecule of the present invention include pUC8, pUC9, pBR322 and pBR329 (Biorad Laboratories, Richmond, Calif.), pPL and pKK223 (Pharmacia, Piscataway, N.J.), pQE50 (Qiagen, Chatsworth, Calif.), and pGEM-T EASY (Promega, Madison, Wis.), pcDNA6.2/V5-DEST and pcDNA3.2/V5DEST (Invitrogen, Carlsbad, Calif.) among many others. Typical eukaryotic expression vectors that can be engineered to contain a polynucleotide molecule of the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.; Invitrogen), and baculovirus-based expression systems (Promega), among many others.

The regulatory elements of these and other vectors can vary in their strength and specificities. Depending on the host/vector system utilized, any of a number of suitable transcription elements can be used. For instance, when cloning in mammalian cell systems, promoters isolated from the genome of mammalian cells, e.g., mouse metallothionein promoter, or from viruses that grow in these cells, e.g., vaccinia virus 7.5 K promoter or Maloney murine sarcoma virus long terminal repeat, can be used. Promoters obtained by recombinant DNA or synthetic techniques can also be used to provide for transcription of the inserted sequence. In addition, expression from certain promoters can be elevated in the presence of particular inducers, e.g., zinc and cadmium ions for metallothionein promoters. Non-limiting examples of transcriptional regulatory regions or promoters include for bacteria, the β-gal promoter, the T7 promoter, the TAC promoter, trp and lac promoters, trp-lac fusion promoters, etc.; for yeast, glycolytic enzyme promoters, such as ADH-I and -II promoters, GPK promoter, PGI promoter, TRP promoter, etc.; and for mammalian cells, SV40 early and late promoters, and adenovirus major late promoters, among others.

Expression vectors can also be constructed that will express a fusion/chimeric RNA comprising the HSR1 molecule of the present invention or a fragment thereof. Such fusion/chimeric can be used, e.g., to study the functional and/or structural properties of the HSR1, or to aid in the identification or purification, or to improve the stability, of a recombinantly-expressed HSR1.

Expression vectors of the present invention also include various expression vectors for expression of HSF and eEF1A proteins (as well as any other molecules interacting with HSR1 and/or HSF/HSR1/eEF1A ternary complex). Possible fusion protein expression vectors include but are not limited to vectors incorporating sequences that encode β-galactosidase and trpE fusions, maltose-binding protein (MBP) fusions, glutathione-S-transferase (GST) fusions, polyhistidine fusions (e.g., $His_6$), V5, HA, and myc. Methods known in the art can be used to construct expression vectors encoding these and other fusion proteins. In a specific embodiment, the present invention provides expression vectors for production of fusion HSF or eEF1A proteins, e.g., to assist their purification or detection. In non-limiting embodiments, e.g., an HSF- or eEF1A-MBP fusion protein can be purified using amylose resin; an HSF- or eEF1A-GST fusion protein can be purified using glutathione-agarose beads; and an HSF- or eEF1A-$His_6$ fusion protein can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to an HSF or eEF1A protein of the present invention. In a non-limiting embodiment, a nucleotide sequence coding for the FLAG™ epitope tag (International Biotechnologies Inc.), which is a hydrophilic marker peptide, can be inserted by standard techniques into the expression vector at a point corresponding, e.g., to the amino or carboxyl terminus of the HSF or eEF1A protein. The expressed HSF or eEF1A protein-FLAG™ epitope fusion product can then be detected and affinity-purified using commercially available anti-FLAG™ antibodies. The expression vector can also be engineered to contain polylinker sequences that encode specific protease cleavage sites so that the expressed HSF or eEF1A protein can be released from a carrier region or fusion partner by treatment with a specific protease. For example, the fusion protein vector can include a nucleotide sequence encoding a thrombin or factor Xa cleavage site, among others.

To aid in the selection of host cells transformed or transfected with a recombinant vector of the present invention, the vector can be engineered to further comprise a coding sequence for a reporter gene product or other selectable marker. Such a coding sequence is preferably in operative association with the regulatory elements, as described above. Reporter genes that are useful in practicing the invention are known in the art, and include those encoding chloramphenicol acetyltransferase (CAT), green fluorescent protein (GFP), firefly luciferase, and human growth hormone (hGH), among others. Nucleotide sequences encoding selectable markers are known in the art, and include those that encode gene products conferring resistance to antibiotics or anti-metabolites, or that supply an auxotrophic requirement. Examples of such sequences include those that encode thymidine kinase activity, or resistance to methotrexate, ampicillin, kanamycin, chloramphenicol, zeocin, pyrimethamine, aminoglycosides, hygromycin, blasticidine, or neomycin, among others.

b. Transformation of Host Cells

The present invention further provides a transformed host cell comprising a polynucleotide molecule or recombinant vector of the present invention, and a cell line derived therefrom. Such host cells are useful for cloning and/or expressing polynucleotide molecules of the present invention. Such transformed host cells include but are not limited to microorganisms, such as bacteria transformed with recombinant bacteriophage DNA, plasmid DNA or cosmid DNA vectors, or yeast transformed with a recombinant vector, as well as transfected plant cells or animal cells, such as insect cells (e.g., *Drosophila* Kc cells) or mammalian cells (e.g., mouse, rat, hamster [e.g., BHK-21 cells ATCC Accession No. CRL-1632], mouse, cow, monkey, or human cells [e.g., HeLa cells ATCC Accession No. CCL-2]). In a specific embodiment, the present invention provides HeLa cell lines stably expressing GFP (HS) or HSR1-directed siRNA (SEQ ID NO: 7 and SEQ ID NO: 27 [siHSR1-160] or SEQ ID NO: 20 and SEQ ID NO: 28 [siHSR1-224]) or antisense HSR1 (aHSR1; SEQ ID NO: 3).

The recombinant vector of the invention is preferably transformed or transfected into one or more host cells of a substantially homogeneous culture of cells. The vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants can be conducted by standard procedures, such as by selecting for cells expressing a selectable marker, e.g., antibiotic resistance, associated with the recombinant expression vector.

Once an expression vector is introduced into the host cell, the presence of the polynucleotide molecule of the present invention, either integrated into the host cell genome or maintained episomally, can be confirmed by standard techniques, e.g., by DNA-DNA, DNA-RNA, or RNA-antisense RNA hybridization analysis, restriction enzyme analysis, PCR analysis including reverse transcriptase PCR(RT-PCR), detecting the presence of a "marker" gene function, or by immunological or functional assay to detect the expected protein product.

6. Use of the Nucleic Acid Molecules of the Invention to Modulate HSR1 Function and Expression As disclosed above, the HSR1-related nucleic acid molecules of the invention or the nucleic acid molecules comprising sequences that hybridize to them under standard hybridization conditions (including their homologs/orthologs, complementary sequences and various oligonucleotide probes and primers derived from them) can be used to modulate (e.g., inhibit or augment) a function of HSR1 or HSF/HSR1/eEF1A ternary complex (e.g., by modulating interaction between HSR1 and eEF1A, interaction between HSR1 and HSF, formation of a ternary complex HSF/HSR1/eEF1A, activation of HSF DNA binding, the ability of HSR1 to undergo a conformational change in response to stress, etc.). The HSR1-related nucleic acid molecules of the invention or the nucleic acid molecules comprising sequences that hybridize to them under standard hybridization conditions (including their homologs/orthologs, complementary sequences and various oligonucleotide probes and primers derived from them) can be also used to modulate expression of HSR1 genes (e.g., by inhibiting transcription, processing, transport, or by promoting degradation of corresponding RNAs). In a specific embodiment (see more details below), the present invention provides HSR1-specific antisense oligonucleotides, RNA interference (RNAi) molecules, ribozymes, and triple helix forming oligonucleotides (TFOs) which can be effectively used to mediate any of these functions. In conjunction with these antisense oligonucleotides, RNA interference (RNAi) molecules, ribozymes, and triple helix forming oligonucleotides (TFOs), the present invention provides a method of inhibiting stress tolerance in a cell comprising administering said molecules to the cell.

Also, as specified in greater detail below, the antisense oligonucleotides, RNA interference (RNAi) molecules, ribozymes, and triple helix forming oligonucleotides (TFOs) of the invention can be used as a basis for developing therapeutics to treat cancer, inflammation, ischemia, neurodegenerative disorders, age-related diseases, HIV infection, deafness, and related disorders.

a. Antisense Nucleic Acids

As specified in Section 4, above, to achieve modulation of a function of an HSR1 and/or HSF/HSR1/eEF1A ternary complex or modulation of expression of an HSR1 gene, the nucleic acid molecules of the invention can be used to design antisense oligonucleotides. Antisense oligonucleotides of the invention comprise from about 6 to about 200 nucleotides, but are typically 13 to 50 nucleotides in length. For example, Examples Section, infra, provides four specific 45-mer antisense oligonucleotides corresponding to the cloned hamster HSR1 (SEQ ID NO: 1), i.e., $1^{HSR1}$ (SEQ ID NO: 9; complementary to HSR1 [SEQ ID NO: 1] nt 1-44), $2^{HSR1}$ (SEQ ID NO: 10; complementary to HSR1 [SEQ ID NO: 1] nt 40-84), $5^{HSR1}$ (SEQ ID NO: 11; complementary to HSR1 [SEQ ID NO: 1] nt 157-201), $6^{HSR1}$ (SEQ ID NO: 12; complementary to HSR1 [SEQ ID NO: 1] nt 196-240), which produce significant inhibition of HSF activation in the in vitro reconstituted system. Furthermore, as disclosed in the Examples, when transfected in cultured cells (e.g., BHK and HeLa), phosphothioate derivative of the oligonucleotide 6HSR1 impairs the HS response and suppresses the induction of thermotolerance in vivo by producing a significant decrease in the level of HSF DNA binding activity and blocking the synthesis of HSP72 protein after heat shock. In addition to the antisense oligonucleotides which inhibit HSF activation and impair HS response, the present invention also encompasses antisense oligonucleotides which stimulate HSF activation and HS response. Such "activating" antisense oligonucleotides may function by changing HSR1 conformation into a conformation available for HSF activation.

The antisense oligonucleotides of the invention comprise sequences complementary to at least a portion of the corresponding HSR1 or HSR1-encoding nucleic acid. However, 100% sequence complementarity is not required so long as formation of a stable duplex (for single stranded antisense oligonucleotides) or triplex (for double stranded antisense oligonucleotides) can be achieved. The ability to hybridize will depend on both the degree of complementarity and the length of the antisense oligonucleotides. Generally, the longer the antisense oligonucleotide, the more base mismatches with the corresponding nucleic acid target can be tolerated. One skilled in the art can ascertain a tolerable degree of mismatch by use of standard procedures to determine the melting point of the hybridized complex.

The antisense oligonucleotides can be DNA or RNA or chimeric mixtures, or derivatives or modified versions thereof, and can be single-stranded or double-stranded. The antisense oligonucleotides can be modified at the base moiety, sugar moiety, or phosphate backbone, or a combination thereof. For example, a HSR1-specific antisense oligonucleotide can comprise at least one modified base moiety selected from a group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the HSR1-specific antisense oligonucleotide comprises at least one modified sugar moiety, e.g., a sugar moiety selected from arabinose, 2-fluoroarabinose, xylulose, and hexose.

In yet another embodiment, the HSR1-specific antisense oligonucleotide comprises at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof. In a specific embodiment, the present invention provides phosphorothioate antisense oligonucleotides (e.g., 6HSR1 and anti-$6^{HSR1}$ phosphothioate modified at 3' and 5' ends to increase their stability) and chimeras between methylphosphonate and phosphodiester oligonucleotides. These oligonucleotides appear to provide good in vivo activity due to solubility, nuclease resistance, good cellular uptake, ability to activate RNase H, and high sequence selectivity.

The antisense oligonucleotide can include other appending groups such as peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810) or blood-brain barrier (see, e.g., PCT Publication No. WO 89/10134), hybridization-triggered cleavage agents (see, e.g., Krol et al., BioTechniques 1988; 6:958-976), intercalating agents (see, e.g., Zon, Pharm. Res. 1988; 5:539-549), etc.

In another embodiment, the antisense oligonucleotide can include α-anomeric oligonucleotides. An α-anomeric oligonucleotide forms specific double-stranded hybrids with complementary RNA in which, contrary to the usual β-units, the strands run parallel to each other (Gautier et al., Nucl. Acids Res. 1987; 15:6625-6641).

In yet another embodiment, the antisense oligonucleotide can be a morpholino antisense oligonucleotide (i.e., an oligonucleotide in which the bases are linked to 6-membered morpholine rings, which are connected to other morpholine-linked bases via non-ionic phosphorodiamidate intersubunit linkages). Morpholino oligonucleotides are highly resistant to nucleases and have good targeting predictability, high in-cell efficacy and high sequence specificity (U.S. Pat. No. 5,034,506; Summerton, Biochim. Biophys. Acta 1999; 1489: 141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Antisense oligonucleotides of the invention may be chemically synthesized, for example using appropriately protected ribonucleoside phosphoramidites and a conventional DNA/RNA synthesizer. Antisense nucleic acid oligonucleotides of the invention can also be produced intracellularly by transcription from an exogenous sequence. For example, a vector can be introduced in vivo such that it is taken up by a cell within which the vector or a portion thereof is transcribed to produce an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art, used for replication and expression in mammalian cells. In another embodiment, "naked" antisense nucleic acids can be delivered to adherent cells via "scrape delivery", whereby the antisense oligonucleotide is added to a culture of adherent cells in a culture vessel, the cells are scraped from the walls of the culture vessel, and the scraped cells are transferred to another plate where they are allowed to re-adhere. Scraping the cells from the culture vessel walls serves to pull adhesion plaques from the cell membrane, generating small holes that allow the antisense oligonucleotides to enter the cytosol.

b. RNA Interference (RNAi)

RNA interference (RNAi) is a process of sequence-specific post-transcriptional gene silencing by which double stranded RNA (dsRNA) homologous to a target locus can specifically inactivate gene function in plants, fungi, invertebrates, and vertebrates, including mammals (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245).

For mammalian systems, RNAi commonly involves the use of dsRNAs that are greater than 500 bp; however, it can also be activated by introduction of either siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The siRNAs to be used in the methods of the present invention are preferably short double stranded nucleic acid duplexes comprising annealed complementary single stranded nucleic acid molecules. In preferred embodiments, the siRNAs are short dsRNAs comprising annealed complementary single strand RNAs. However, the invention also encompasses embodiments in which the siRNAs comprise an annealed RNA:DNA duplex, wherein the sense strand of the duplex is a DNA molecule and the antisense strand of the duplex is a RNA molecule.

Preferably, each single stranded nucleic acid molecule of the siRNA duplex is of from about 19 nucleotides to about 27 nucleotides in length. In preferred embodiments, duplexed siRNAs have a 2 or 3 nucleotide 3' overhang on each strand of the duplex. In preferred embodiments, siRNAs have 5'-phosphate and 3'-hydroxyl groups.

The RNAi molecules to be used in the methods of the present invention comprise nucleic acid sequences that are complementary to the nucleic acid sequence of a portion of the target HSR1 or HSR1-encoding nucleic acid. In certain embodiments, the portion of the target nucleic acid to which the RNAi probe is complementary is at least about 15 nucleotides in length. The target locus to which an RNAi probe is complementary may represent a transcribed portion of the HSR1 gene or an untranscribed portion of the HSR1 gene (e.g., intergenic regions, repeat elements, etc.). As disclosed in the Examples Section, infra, the present invention provides HSR1-directed siRNAs, siHSR1-160 (SEQ ID NO: 7 and SEQ ID NO: 27) and siHSR1-224 (SEQ ID NO: 20 and SEQ ID NO: 28; corresponding to hamster HSR1 [SEQ ID NO: 1] nt 196-240), and corresponding mutant siRNAs, mut160 (C11→G; SEQ ID NO: 8 and SEQ ID NO: 29) and mut224 (G4→C; SEQ ID NO: 21 and SEQ ID NO: 30).

The RNAi molecules may include one or more modifications, either to the phosphate-sugar backbone or to the nucleoside. For example, the phosphodiester linkages of natural RNA may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Where the RNAi molecule is produced synthetically, or by in vitro transcription, a modified ribonucleoside may be introduced during synthesis or transcription.

According to the present invention, siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

The shRNAs to be used in the methods of the present invention comprise a single stranded "loop" region connecting complementary inverted repeat sequences that anneal to form a double stranded "stem" region. Structural considerations for shRNA design are discussed, for example, in McManus et al., RNA 2002; 8:842-850. In certain embodiments the shRNA may be a portion of a larger RNA molecule, e.g., as part of a larger RNA that also contains U6 RNA sequences (Paul et al., supra).

In preferred embodiments, the loop of the shRNA is from about 1 to about 9 nucleotides in length. In preferred embodiments the double stranded stem of the shRNA is from about 19 to about 33 base pairs in length. In preferred embodiments, the 3' end of the shRNA stem has a 3' overhang. In particularly preferred embodiments, the 3' overhang of the shRNA stem is from 1 to about 4 nucleotides in length. In preferred embodiments, shRNAs have 5'-phosphate and 3'-hydroxyl groups.

Although the RNAi molecules useful according to the invention preferably contain nucleotide sequences that are fully complementary to a portion of the target nucleic acid, 100% sequence complementarity between the RNAi probe and the target nucleic acid is not required to practice the invention.

Similar to the above-described antisense oligonucleotides, RNAi molecules of the invention can be synthesized by standard methods known in the art, e.g., by use of an automated synthesizer. RNAs produced by such methodologies tend to be highly pure and to anneal efficiently to form siRNA duplexes or shRNA hairpin stem-loop structures. Following chemical synthesis, single stranded RNA molecules are deprotected, annealed to form siRNAs or shRNAs, and purified (e.g., by gel electrophoresis or HPLC). Alternatively, standard procedures may used for in vitro transcription of RNA from DNA templates carrying RNA polymerase promoter sequences (e.g., T7 or SP6 RNA polymerase promoter sequences). Efficient in vitro protocols for preparation of siRNAs using T7 RNA polymerase have been described (Donzé and Picard, Nucleic Acids Res. 2002; 30:e46; and Yu et al., Proc. Natl. Acad. Sci. USA 2002; 99:6047-6052). Similarly, an efficient in vitro protocol for preparation of shRNAs using T7 RNA polymerase has been described (Yu et al., supra). The sense and antisense transcripts may be synthesized in two independent reactions and annealed later, or may be synthesized simultaneously in a single reaction.

RNAi molecules may be formed within a cell by transcription of RNA from an expression construct introduced into the cell. For example, both a protocol and an expression construct for in vivo expression of siRNAs are described in Yu et al., supra. Similarly, protocols and expression constructs for in vivo expression of shRNAs have been described (Brummelkamp et al., supra; Sui et al., supra; Yu et al., supra; McManus et al., supra; Paul et al., supra).

The expression constructs for in vivo production of RNAi molecules comprise RNAi encoding sequences operably linked to elements necessary for the proper transcription of the RNAi encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The RNAi expression constructs can further comprise vector sequences that facilitate the cloning of the expression constructs. Standard vectors that maybe used in practicing the current invention are known in the art (e.g., pSilencer 2.0-U6 vector, Ambion Inc., Austin, Tex.).

c. Ribozyme Modulation

In another embodiment, a function of HSR1 and/or HSF/HSR1/eEF1A ternary complex or expression of HSR1 genes of the present invention can be modulated by ribozymes designed based on the nucleotide sequence thereof.

Ribozymes are enzymatic RNA molecules capable of catalyzing the sequence-specific cleavage of RNA (for a review, see Rossi, Current Biology 1994; 4:469-471). The mechanism of ribozyme action involves sequence-specific hybridization of the ribozyme molecule to complementary target RNA, followed by an endonucleolytic cleavage event. The composition of ribozyme molecules must include: (i) one or more sequences complementary to the target RNA; and (ii) a catalytic sequence responsible for RNA cleavage (see, e.g., U.S. Pat. No. 5,093,246).

According to the present invention, the use of hammerhead ribozymes is preferred. Hammerhead ribozymes cleave RNAs at locations dictated by flanking regions that form complementary base pairs with the target RNA. The sole requirement is that the target RNA has the following sequence of two bases: 5'-UG-3'. The construction of hammerhead ribozymes is known in the art, and described more fully in Myers, Molecular Biology and Biotechnology: A Comprehensive Desk Reference, VCH Publishers, New York, 1995 (see especially FIG. 4, page 833) and in Haseloff and Gerlach, Nature 1988; 334:585-591.

Preferably, the ribozymes of the present invention which act to inhibit HSR1 function are engineered so that the cleavage recognition site is located near the 5' end of HSR1, i.e., to increase efficiency and minimize the intracellular accumulation of non-functional HSR1 molecules.

The present invention encompasses both inhibitory and "activating" ribozyme molecules. Activating ribozyme molecules can be designed, e.g., to eliminate a potentially inhibitory domain(s) of HSR1.

As in the case of antisense oligonucleotides, ribozymes of the invention can be composed of modified oligonucleotides (e.g., for improved stability, targeting, etc.). These can be delivered to cells which express the target HSR1 molecules in vivo. A preferred method of delivery involves using a DNA construct "encoding" the ribozyme under the control of a strong constitutive pol III or pol II promoter, so that transfected cells will produce sufficient quantities of the ribozyme to catalyse HSR1 cleavage. However, because ribozymes, unlike antisense molecules, are catalytic, a lower intracellular concentration may be required to achieve an adequate level of efficacy.

Ribozymes can be prepared by any method known in the art for the synthesis of DNA and RNA molecules, as discussed above. Ribozyme technology is described further in Intracellular Ribozyme Applications: Principals and Protocols, Rossi and Couture eds., Horizon Scientific Press, 1999.

7. Triple Helix Forming Oligonucleotides (TFOs)

Nucleic acid molecules useful to modulate HSR1 and/or HSF/HSR1/eEF1A function or HSR1 gene expression via triple helix formation are preferably composed of deoxynucleotides. The base composition of these oligonucleotides is typically designed to promote triple helix formation via Hoogsteen base pairing rules, which generally require sizeable stretches of either purines or pyrimidines to be present on one strand of a duplex. Nucleotide sequences may be pyrimidine-based, resulting in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., those containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, sequences can be targeted for triple helix formation by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Similarly to HSR1-specific RNAi, antisense oligonucleotides, and ribozymes, triple helix molecules of the invention can be prepared by any method known in the art. These include techniques for chemically synthesizing oligodeoxyribonucleotides and oligoribonucleotides such as, e.g., solid phase phosphoramidite chemical synthesis. Alternatively, RNA molecules can be generated by in vitro or in vivo transcription of DNA sequences "encoding" the particular RNA molecule. Such DNA sequences can be incorporated into a wide variety of vectors that incorporate suitable RNA polymerase promoters such as the T7 or SP6 polymerase promoters.

8. Use of the Antisense Oligonucleotides, RNA Interference (RNAi) Molecules, Ribozymes, and Triple Helix Forming Oligonucleotides (TFOs) of the Invention in Developing Novel Cancer Treatments One of the major problems in cancer treatment today is the resistance of tumor cells to existing therapies. At least part of this resistance is due to increased synthesis of heat shock proteins (HSPs). As specified in the Background Section, supra, HSPs are synthesized in all cells in response to adverse conditions such as heat stress. They protect the cell from injury by preventing denaturation of cellular proteins and ensuring correct folding of newly synthesized polypeptides. In cancer cells, high level of HSPs prevents initiation of apoptosis, or programmed cell death, in response to therapeutic treatment. Indeed, as described in Tang et al. (Cell Stress and Chaperones 2005; 10:46-58), HSF and HSP levels are elevated in more highly malignant prostate carcinoma cells. As the synthesis of HSPs in response to stress is controlled by transcription factor HSF, finding a way to inhibit HSF activation in cancer cells will result in increasing efficiency of existing anti-cancer treatments.

The present invention provides a novel way to inhibit HSF activation in cancer cells by disclosing for the first time that the activation of HSF in response to heat stress requires at least two additional components: translation elongation factor eEF1A and a novel Heat Shock RNA (HSR1). As disclosed herein, these two components act together to activate HSF. The key role played by the newly discovered HSR1 in this process provides a rational for new therapeutic agents that would block excessive production of HSPs in cancer cells thus rendering them more susceptible to conventional treatments such as chemotherapy, radiation therapy, thermal therapy, etc.

Accordingly, in conjunction with the novel HSR1-related nucleic acids and novel HSF/HSR1/eEF1A ternary complex, the present invention provides novel anti-cancer agents based on the HSR1-specific antisense oligonucleotides, RNA interference (RNAi) molecules, ribozymes, and triple helix forming oligonucleotides (TFOs) as well as methods for using such agents to treat cancer. The novel anti-cancer agents of the present invention can be used in conjunction with existing treatments to improve their effect by increasing the sensitivity of the cells to pro-apoptotic stimuli such as thermo-, chemo-, and radiotherapeutic treatments.

Specifically, as disclosed in Examples Section, infra, HSR1 antisense oligonucleotides such as phosphothioate derivative of the oligonucleotide $6^{HSR1}$ (SEQ ID NO: 12; complementary to bases 196-240 of hamster HSR1 [SEQ ID NO: 1]) are capable of inhibiting HSF1 activation in vivo when transfected in BHK and HeLa cells and render them heat sensitive. The data show that this treatment dramatically reduces the level of HSP expression and, therefore, promotes pro-apoptotic processes that are otherwise blocked by increased HSP expression.

As disclosed in Examples, infra, to develop effective anti-cancer agents based on the HSR1-specific antisense oligonucleotides, RNA interference (RNAi) molecules, ribozymes, and triple helix forming oligonucleotides (TFOs) of the invention, candidate molecules can be introduced in a thermotolerant cancer cell line (e.g., breast cancer cell line Bcap37; see Wang, et al., Biochem. Biophys. Res. Commun. 2002; 290:1454-1461) followed by evaluating the HSP expression levels and survival of cells after heat shock treatment in comparison to that of untransfected cells. HSR1-specific antisense oligonucleotides, RNA interference (RNAi) molecules, ribozymes, and triple helix forming oligonucleotides (TFOs) which show the strongest effect on cell survival and HSP expression can be further optimized (e.g., by increasing their resistance to nucleases, increasing the efficiency of their targeting to cancer cells, increasing their sequence specificity [e.g., by introducing phosphothioate or morpholino modifications or using LNA], and reducing the size) making them even more potent in inhibition of cell survival and inhibition of HSP expression. The most potent anti-cancer molecules selected in tissue culture experiments can be further tested for their ability to affect the growth of tumors induced in nude mice (e.g., by injection of thermotolerant cancer cells) and subjected to heat shock treatment or to chemo- or radiation therapy.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for treating cancer in a mammal comprising administering said therapeutics to the mammal. In a specific embodiment, the mammal is human. In another specific embodiment, the method further comprises subjecting the mammal to a treatment selected from the group consisting of radiation therapy, chemotherapy, thermotherapy, and any combination thereof.

Similarly, the present invention provides a method for increasing sensitivity of a cancer cell to an anti-cancer treatment (e.g., radiation treatment, chemical treatment, thermal treatment, or any combination thereof) and thus improving efficiency of such anti-cancer treatment in a mammal comprising administering to the mammal the therapeutics of the invention. The relative timing of antisense/RNAi/ribozyme/TFO administration and anti-cancer treatment would depend on the delivery mechanism for antisense/RNAi/ribozyme/TFO and on the type of the specific anti-cancer treatment used. Generally, cells may become more sensitive to an anti-cancer treatment as soon as one hour after antisense/RNAi/ribozyme/TFO administration.

Cancers treatable using the methods of the present invention include without limitation fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, hepatocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, among others.

As disclosed above, the anti-cancer compositions of the present invention are advantageously used in combination with other treatment modalities, including without limitation radiation, chemotherapy, and thermotherapy.

Chemotherapeutic agents used in the methods of the present invention include without limitation taxol, taxotere and other taxoids (e.g., as disclosed in U.S. Pat. Nos. 4,857,653; 4,814,470; 4,924,011, 5,290,957; 5,292,921; 5,438,072; 5,587,493; European Patent No. EP 253 738; and PCT Publication Nos. WO 91/17976, WO 93/00928, WO 93/00929, and WO 96/01815), cisplatin, carboplatin, (and other platinum intercalating compounds), etoposide and etoposide phosphate, bleomycin, mitomycin C, CCNU, doxorubicin, daunorubicin, idarubicin, ifosfamide, methotrexate, mercaptopurine, thioguanine, hydroxyurea, cytarabine, cyclophosphamide, nitrosoureas, mitomycin, dacarbazine, procarbizine, campathecins, dactinomycin, plicamycin, mitoxantrone, asparaginase, vinblastine, vincristine, vinorelbine, paclitaxel, docetaxel, calicheamicin, and the like.

Typical radiation therapy used in the methods of the invention includes without limitation radiation at 1-2 Gy.

Also encompassed by the present invention is radiation therapy and chemotherapy via local delivery of radioconjugates and chemotherapeutics, respectively. Directing the cytotoxic exposure directly to the tumor itself is a commonly used approach to deliver a cytotoxic drug while minimizing the cytotoxic exposure of normal tissues. However, one of the factors which limit the effectiveness of such an approach is incomplete induction of tumor cell death because of limited dose delivery. Thus, it would be highly desirable to concurrently use the HSR1-specific therapeutics of the invention to enhance the sensitivity of the tumor cells to the particular cytotoxic agent. Tumor-specific delivery is commonly achieved by conjugating a cytotoxic agent (e.g., a toxins (such as ricin) or a radioisotope) to an antibody that preferentially targets the tumor (e.g., anti-CD2 in neuroblastoma or anti-Her2-neu in certain breast carcinomas). The targeting may be also done with natural targeting (i.e., with radioactive iodine in the treatment of thyroid carcinoma), physical targeting (i.e., administration of a radioisotope to a particular body cavity), or other targeting protein (e.g., ferritin in hepatocellular carcinoma).

In addition to combination with conventional cancer therapies such as chemotherapy, radiation therapy, thermotherapy, and surgery (tumor resection), HSR1-targeted therapy of a tumor can be combined with other anti-tumor therapies, including but by no means limited to suicide gene therapy (i.e., introduction of genes that encode enzymes capable of conferring to tumor cells sensitivity to chemotherapeutic agents such as thymidine kinase of herpes simplex virus or varicella zoster virus and bacterial cytosine deaminase), anti-oncogene or tumor suppressor gene therapy (e.g., using anti-oncogene molecules including monoclonal antibodies, single chain antibody vectors, antisense oligonucleotide constructs, ribozymes, immunogenic peptides, etc.), administration of tumor growth inhibitors (e.g., interferon (IFN)-γ, tumor necrosis factor (TNF)-α, TNF-β, and similar cytokines, antagonists of tumor growth factor (TGF)-β and IL-10, etc.), administration of angiogenesis inhibitors (e.g., fragments of angiogenic proteins that are inhibitory [such as the ATF of urokinase], angiogenesis inhibitory factors [such as angiostatin and endostatin], tissue inhibitors of metalloproteinase, soluble receptors of angiogenic factors [such as the urokinase receptor or FGF/VEGF receptor], molecules which block endothelial cell growth factor receptors, and Tie-1 or Tie-2 inhibitors), vasoconstrictive agents (e.g., nitric oxide inhibitors), immune therapies with an immunologically active polypeptide (including immunostimulation, e.g., in which the active polypeptide is a cytokine, lymphokine, or chemokine [e.g., IL-2, GM-CSF, IL-12, IL-4], and vaccination, in which the active polypeptide is a tumor specific or tumor associated antigen), and the like.

9. Use of the Antisense Oligonucleotides, RNA Interference (RNAi) Molecules, Ribozymes, and Triple Helix Forming Oligonucleotides (TFOs) of the Invention in Developing Novel Anti-Inflammatory Agents As specified in the Background Section, supra, HSPs, and HSP70 family in particular, is considered a part of a protective mechanism against inflammation (Jattela et al., EMBO J. 1992; 11:3507-3512; Morris et al., Int. Biochem. Cell Biol.

1995; 27:109-122; Ianaro et al., FEBS Lett. 2001; 499:239-244; Van Molle et al., Immunity 2002; 16:685-695; Ianaro et al., Mol. Pharmacol. 2003; 64:85-93; Ianaro et al., FEBS Lett. 2001; 499:239-244; Ianaro et al., FEBS Lett. 2001; 508:61-66). It follows, that selective HSF-mediated transcriptional activation of HSP genes may lead to remission of the inflammatory reaction.

As disclosed above, the HSR1-specific nucleic acids of the invention such as, e.g., antisense oligonucleotides, RNA interference (RNAi) molecules, ribozymes, and triple helix forming oligonucleotides (TFOs), can be used to activate HSF and in this way provide a basis for developing novel anti-inflammatory therapeutics.

To develop effective anti-inflammatory agents based on the HSR1-specific antisense oligonucleotides, RNA interference (RNAi) molecules, ribozymes, and triple helix forming oligonucleotides (TFOs) of the invention, candidate molecules can be first tested in vitro, e.g., by measuring TNF-α and IL-1β secretion in mononuclear cells of human peripheral blood or RAW 264.7 cells after their stimulation with lipopolysaccharide (LPS).

Therapeutics which produce the strongest anti-inflammatory effect in in vitro assays can be further tested in vivo in various animal models of inflammation. Examples of the useful animal models include without limitation mouse model of LPS-induced TNF-α secretion (Badger et al., J. Pharmac. Env. Therap. 1996; 279:1453-1461), rat paw edema induced by subplantar injection of λ-carrageenin (Ianaro et al., Mol. Pharmacol. 2003; 64:85-93), mouse pain model produced by injection of an irritant, usually acetic acid, into the peritoneal cavity (Collier et al. Pharmac. Chemother. 1968; 32:295-310; Fukawa et al., J. Pharmacol. Meth. 1980; 4:251-259; Schweizer et al., Agents Actions 1988; 23:29-31), etc. In these models, the activity of the novel therapeutics in inhibiting inflammation can be determined using various methods known in the art, including without limitation, use of contrast ultrasound in conjunction with injection of microbubbles, measurement of inflammatory cytokines (such as TNF-α, IL-1, IFN-γ), measurement of activated immune system cells (e.g., measurement of the invasion or accumulation in an organ or tissue of proinflammatory lymphoid cells or the presence locally or peripherally of activated pro-inflammatory lymphoid cells recognizing a pathogen or an antigen specific to the organ or tissue) as well as observation (reduction of erythema/redness, reduction of elevated body/tissue temperature, reduction of swelling/edema, reduction of pain in the affected area, reduction of pruritus or burning sensation, improvement in function of the afflicted organ).

HSR1-specific antisense oligonucleotides, RNA interference (RNAi) molecules, ribozymes, and triple helix forming oligonucleotides (TFOs) which show the strongest effect in vitro and in animal models can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in inhibition of various signs of inflammation and activation of HSP expression.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for inhibiting an inflammatory reaction in a mammal comprising administering said therapeutics to the mammal. In a specific embodiment, the mammal is human.

The novel therapeutics of the invention can be used in the prophylaxis as well as in the therapeutic treatment of several disorders (diseases and other pathological inflammatory conditions) caused by or associated with an abnormal or undesirable (excessive, nonregulated, or deregulated) inflammatory immune response involving the production of inflammatory cytokines or other inflammation mediators, including without limitation TNF-α and IL-1β. They include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar UV sources); inflammatory bowel disease, such as Crohn's disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection.

The novel anti-inflammatory agents of the present invention can be used in conjunction with existing therapeutics such as inhibitors of TNF-α, inhibitors of COX-1/COX-2, inhibitors of IL-1β, etc. In a specific embodiment, the novel therapeutics of the invention are administered in combination with Non-Steroidal Anti-Inflammatory Drugs (NSAIDs). Suitable NSAIDs include, but are not limited to, those which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), and as inhibitors of both cyclooxygenase and lipoxygenase relates to NSAID, such as the commercially available NSAIDs aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAID compounds are disclosed in U.S. Pat. No. 6,297,260 and International Patent Application No. WO 01/87890.

10. Use of the Antisense Oligonucleotides, RNA Interference (RNAi) Molecules, Ribozymes, and Triple Helix Forming Oligonucleotides (TFOs) of the Invention in Developing Novel Therapeutics to Treat Ischemia/Reperfusion Injury and Neurodegenerative Disorders As specified in the Background Section, supra, HSPs, and HSP70 family in particular, is also considered a part of a protective mechanism against cerebral or cardiac ischemia and neurodegenerative diseases (such as Alzheimer's disease, Parkinson's disease, amyotrophic lateral sclerosis [ALS], Huntington's disease, spinobulbar muscular atrophy, dentatorubral pallidoluysian atrophy, Kennedy disease, spinocerebellar ataxias, etc.) (Westerheide and Morimoto, J. Biol. Chem. 2005; 280:33097-100; Klettner, Drug News Perspect. 2004; 17:299-306; Pockley, Circulation 2002; 105:1012-1017; Hargitai et al., Biochem. Biophys. Res. Commun. 2003; 307:689-695; Yenari et al., Ann. Neurol. 1998; 44:584-591; Suzuki et al., J. Mol. Cell. Cardiol. 1998; 6:1129-1136; Warrik et al., Nat. Genet. 1999; 23:425-428; Plumier et al., J. Clin. Invest. 1995; 95:1854-1860; Marber et al., ibid., pp. 1446-1456; Radford et al., Proc. Natl. Acad. Sci. USA 1996; 93:2339-2342). It follows, that elevated activity of HSF and resulting HSF-mediated transcriptional activation of HSP genes may lead to inhibition/prevention of ischemia/reperfusion injury and neurodegenerative disorders. Indeed, as summarized in the reviews by Latchman (Cardiovascular Research 2001; 51:637-646) and Klettner (Drug News Perspect. 2004; 17:299-306), a number of studies have shown that prior induction of the HSPs by mild stress has a protective effect against a more severe stress, and overexpression of an individual HSP in cardiac cells or neurons in culture or in the intact tissue also produces a protective effect.

As disclosed above, the HSR1-specific nucleic acids of the invention such as, e.g., antisense oligonucleotides, RNA interference (RNAi) molecules, ribozymes, and triple helix forming oligonucleotides (TFOs), can be used to activate HSF and in this way provide a basis for developing novel therapeutics to treat ischemia/reperfusion injury and neurodegenerative disorders.

To develop effective therapeutics to treat ischemia/reperfusion injury and neurodegenerative disorders based on the HSR1-specific antisense oligonucleotides, RNA interference (RNAi) molecules, ribozymes, and triple helix forming oligonucleotides (TFOs) of the invention, candidate molecules can be first tested in vitro, e.g., by testing their ability to prevent/decrease neuronal cell death (e.g., upon expression of polyglutamine-expanded proteins such as mutant huntingtin) or cardiomyocyte cell death (e.g., induced by hydrogen peroxide; see Zou et al., Circulation 2003; 108:3024-3030). Therapeutics which produce the best effect in in vitro assays can be further tested in vivo in various animal models of neurodegenerative diseases (see examples in the section below) or animal models of ischemia/reperfusion injury such as mouse model created by transiently ligating the left coronary artery followed by release of suture to allow reperfusion (Harada et al., Circulation 1998; 97:315-317; Zou et al., Circulation 2003; 108:3024-3030). In these models, the activity of the novel therapeutics in inhibiting neurodegenerative disorders or ischemia/reperfusion injury can be determined using various methods known in the art, including without limitation, determination of electrical activity of neural tissue or myocardium, ECG, determination of reduction in neuronal or cardiomyocyte cell death, etc.

HSR1-specific antisense oligonucleotides, RNA interference (RNAi) molecules, ribozymes, and triple helix forming oligonucleotides (TFOs) which show the strongest effect in vitro and in animal models can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in inhibition of various signs of neurodegeneration or ischemia/reperfusion injury and activation of HSP expression.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for inhibiting a neurodegenerative disorder or ischemia/reperfusion injury in a mammal comprising administering said therapeutics to the mammal. In a specific embodiment, the mammal is human.

The novel therapeutics of the invention can be used in the prophylaxis as well as in the therapeutic treatment of cerebral and cardiac ischemia/reperfusion injury as well as various neurodegenerative diseases (e.g., Alzheimer's disease, Parkinson's disease, amyotrophic lateral sclerosis [ALS], Huntington's disease, spinobulbar muscular atrophy, dentatorubral pallidoluysian atrophy, Kennedy disease, spinocerebellar ataxias, etc.).

The novel agents of the present invention can be used in conjunction with existing treatments such as pharmacotherapy (e.g., therapy using cholinesterase inhibitors or NMDA receptor antagonists [in cases of Alzheimer's disease], tissue plasminogen activator (tPA) therapy [in cases of stroke], Vascular Endothelial Growth Factor (VEGF) therapy [in cases of ischemia]) or mechanical intervention (e.g., bypass surgery, coronary angioplasty followed by stent implantation, etc.).

11. Use of the Antisense Oligonucleotides, RNA Interference (RNAi) Molecules, Ribozymes, and Triple Helix Forming Oligonucleotides (TFOs) of the Invention in Developing Novel Anti-Aging Therapeutics As specified in the Background Section, induction of heat shock either by temperature or HSF overexpression can extend life span in model organisms. Because the heat shock response is a general protection mechanism, its therapeutic activation would be therefore useful in treating various age-related diseases (e.g., atherosclerosis and age-related neurodegenerative diseases such as Alzheimer's, Parkinson's, amyotrophic lateral sclerosis [ALS], etc.). Usually, in aged organisms, the general protective systems such as antioxidant protection system and heat shock induction system (both needed to protect damaged proteins) get compromised. One therefore can expect the beneficial role of HSF activation in age-related diseases. For example, amyloid plaque formation in Alzheimer's disease (i.e., extracellular aggregates of Aβ peptides which are deposited as amyloid fibrils or amorphous aggregates due to aberrant processing of the full-length beta-amyloid precursor protein (APP)) can be delayed or reversed by overexpression of HSF or HSPs.

As disclosed above, the HSR1-specific nucleic acids of the invention such as, e.g., antisense oligonucleotides, RNA interference (RNAi) molecules, ribozymes, and triple helix forming oligonucleotides (TFOs), can be used to activate HSF and in this way provide a basis for developing novel therapeutics to treat age-related diseases.

To develop effective anti-aging agents based on the HSR1-specific antisense oligonucleotides, RNA interference (RNAi) molecules, ribozymes, and triple helix forming oligonucleotides (TFOs) of the invention, the ability of candidate molecules to retard or suppress various symptoms of age-related diseases can be first tested in vitro in cultured cells (e.g., fibroblasts, hepatocytes, motor neurons) and/or in model organisms (e.g., C. elegans, Drosophila, mice).

For example, in connection with Alzheimer's disease, neuroblastoma cells can be used (e.g., SK-N-SH cells, ATCC Accession No. HTB-11, Biedler et al., Cancer Res. 1973; 33:2643-52) as they are known to secrete beta-amyloid precursor protein (APP) derivatives into the conditioned medium. The levels of these secreted derivatives of APP can be estimated by probing the conditioned media with specific antibodies to APP using, e.g., the method of Western blotting or ELISA (enzyme linked immunosorbent assay). As animal models of Alzheimer's disease, one can use transgenic mouse animal models expressing APP minigenes that encode FAD-linked APP mutants (e.g., swe or 717, as disclosed, e.g., in U.S. Pat. No. 5,912,410) or the double mutant mouse model described by Borchelt et al. (Neuron 1997; 19:939-945). The latter transgenic mice coexpress an early-onset familial AD (FAD)-linked human presenilin 1 (PS1) variant (A246E) and a chimeric mouse/human APP harboring mutations linked to Swedish FAD kindreds (APPswe). These mice develop numerous amyloid deposits much earlier than age-matched mice expressing APPswe and wild-type human PS1. Expression of APP minigenes that encode FAD-linked APP mutants and, in particular, co-expression of the mutant human PS1 A246E and APPswe elevates levels of Aβ in the brain, and these mice develop numerous diffuse Aβ deposits and plaques in the hippocampus and cortex (Calhoun et al., Proc. Natl. Acad. Sci. USA 1999; 96:14088-14093). Similarly to humans suffering from AD, these and other transgenic animal models are characterized by various cognitive defects such as loss of neurons, learning deficits, problems in object recognition memory, and problems with alternation-spatial reference and working memory (Chen et al., Nature 2000; 408: 975-979).

HSR1-specific antisense oligonucleotides, RNA interference (RNAi) molecules, ribozymes, and triple helix forming oligonucleotides (TFOs) which show the strongest effect in vitro and in animal models can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in activation of HSP expression.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for treating an age-related disease in a mammal comprising administering said therapeutics to the mammal. In a specific embodiment, the mammal is human.

Age-related diseases that can be treated using HSR1-specific antisense oligonucleotides, RNA interference (RNAi) molecules, ribozymes, and triple helix forming oligonucleotides (TFOs) of the present invention include, without limitation, atherosclerosis, neurodegenerative diseases, such as chronic neurodegeneration (e.g., associated with Alzheimer's disease, Parkinson's disease, amyotrophic lateral sclerosis [ALS], etc.), cerebrovascular dementia, acute neurodegeneration (e.g., associated with stroke and trauma), etc.

The novel anti-aging agents of the present invention can be used in conjunction with existing therapeutics such as statins, non-sterodial anti-inflammatory drugs (NSAIDs), etc.

12. Use of the Antisense Oligonucleotides, RNA Interference (RNAi) Molecules, Ribozymes, and Triple Helix Forming Oligonucleotides (TFOs) of the Invention in Developing Novel Anti-Deafness Therapeutics As disclosed in the Background Section, HSF1-mediated induction of HSPs has been also implicated in protection of sensory hair cells against acoustic overexposure, hyperthermia and ototoxic drugs. One therefore can expect the beneficial role of HSF1 activation in treatment of deafness and related disorders.

As disclosed above, the HSR1-specific nucleic acids of the invention such as, e.g., antisense oligonucleotides, RNA interference (RNAi) molecules, ribozymes, and triple helix forming oligonucleotides (TFOs), can be used to activate HSF and in this way provide a basis for developing novel therapeutics to treat deafness and related diseases.

To develop effective anti-deafness agents based on the HSR1-specific antisense oligonucleotides, RNA interference (RNAi) molecules, ribozymes, and triple helix forming oligonucleotides (TFOs) of the invention, the ability of candidate molecules to prevent or ameliorate deafness can be first tested in vitro in cultured cells and/or in model organisms (e.g., by monitoring the loss of the sensory hair cells and the auditory function in mice subjected to acoustic overexposure, hyperthermia or ototoxic drugs).

HSR1-specific antisense oligonucleotides, RNA interference (RNAi) molecules, ribozymes, and triple helix forming oligonucleotides (TFOs) which show the strongest effect in vitro and in animal models can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in activation of HSP expression.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for treating deafness in a mammal comprising administering said therapeutics to the mammal. In a specific embodiment, the mammal is human. The novel anti-deafness agents of the present invention can be used in conjunction with existing therapeutics.

13. Use of the Antisense Oligonucleotides, RNA Interference (RNAi) Molecules, Ribozymes, and Triple Helix Forming Oligonucleotides (TFOs) of the Invention in Developing Novel Anti-HIV Therapeutics As specified in the Background Section, supra, Human Immunodeficiency Virus (HIV) LTR suppression can occur under hyperthermic conditions (Gemer et al., Int. J. Hyperthermia 2000; 16:171-181; Steinhart et al., J. AIDS Hum. Retrovirol. 1996; 11:271-281; Ignatenko and Gerner, Exp.

Cell Res. 2003; 288:1-8; see also Brenner and Wainberg, Expert Opin. Biol. Ther. 2001; 1:67-77). It follows, that HSF-mediated transcriptional activation may lead to inhibition of HIV transcription.

As disclosed above, the HSR1-specific nucleic acids of the invention such as, e.g., antisense oligonucleotides, RNA interference (RNAi) molecules, ribozymes, and triple helix forming oligonucleotides (TFOs), can be used to activate HSF and in this way provide a basis for developing novel therapeutics to treat HIV infection.

To develop effective anti-HIV agents based on the HSR1-specific antisense oligonucleotides, RNA interference (RNAi) molecules, ribozymes, and triple helix forming oligonucleotides (TFOs) of the invention, the ability of candidate molecules to mediate LTR suppression can be first tested in vitro in reconstituted HIV LTR transcription assays or in cultured cells comprising HIV LTR. Therapeutics which produce the strongest inhibition of HIV transcription in in vitro assays can be further tested in vivo in animal models of HIV infection. In these models, the activity of the novel therapeutics in inhibiting HIV infection can be determined using various methods known in the art (e.g., monitoring viral titers or various AIDS-like symptoms).

HSR1-specific antisense oligonucleotides, RNA interference (RNAi) molecules, ribozymes, and triple helix forming oligonucleotides (TFOs) which show the strongest effect in vitro and in animal models can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in inhibition of HIV transcription and activation of HSP expression.

In conjunction with the therapeutics of the invention (e.g., the HSR1-specific antisense oligonucleotides, RNA interference (RNAi) molecules, ribozymes, and triple helix forming oligonucleotides (TFOs)), the present invention also provides a method for inhibiting HIV transcription in a mammal comprising administering said therapeutics to the mammal. In a specific embodiment, the mammal is human.

The novel anti-HIV agents of the present invention can be used in conjunction with existing therapeutics such as azidothimidine (AZT), non-nucleotide analog inhibitors of reverse transcriptase, such as Nevirapine (BI-RG-587), TIBO (R82913), pyrinodes (such as R-697,661 and L-696,227), bis(heteroary) piperazines (BHAPs, such as U-87201E and U-90,152), atevirdine mesylate (ATV) and R-89431; HIV protease inhibitors, including substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-IgG and CD4-PE40; blockers of HIV RNaseH activity, such as the AZT derivative azidothymidine monophosphate; drugs that alter the intracellular milieu to create conditions less favorable for viral replication, such as the free-radical scavengers and glutathione-level restoring drugs (N-acetylcysteine and similar drugs), thalidomine, etc.

14. Screening Methods of the Invention

In one embodiment, the present invention also provides a method for identifying a candidate compound useful for modulating a function of a eukaryotic Heat Shock RNA (HSR1) and/or HSF/HSR1/eEF1A ternary complex, said method comprising: (a) contacting a first cell with a test compound for a time period sufficient to allow the cell to respond to said contact with the test compound; (b) determining in the cell prepared in step (a) the function of the HSR1 and/or HSF/HSR1/eEF1A ternary complex; and (c) comparing the function of the HSR1 and/or HSF/HSR1/eEF1A ternary complex determined in step (b) to the function of the HSR1 and/or HSF/HSR1/eEF1A ternary complex in a second (control) cell that has not been contacted with the test compound; wherein a detectable change in the function of HSR1 and/or HSF/HSR1/eEF1A ternary complex in the first cell in response to contact with the test compound compared to the function of the HSR1 in the second cell that has not been contacted with the test compound, indicates that the test compound modulates the function of the HSR1 and is a candidate compound. In a specific embodiment, both test and control cells are subjected to stress (e.g., heat shock). The test compound can be added after cells had been subjected to stress, or after a preconditioning stress but before the lethal stress, or before cells had been subjected to stress. A function of HSR1 and/or HSF/HSR1/eEF1A ternary complex assayed according to this method can be any function, e.g., stress/temperature-induced conformational change of HSR1, interaction of HSR1 with HSF, interaction of HSR1 with eEF1A, formation of HSF/HSR1/eEF1A ternary complex, activation of HSF-mediated DNA binding, activation of HSP expression, thermotolerance, etc.

In another embodiment, the present invention provides a method for identifying a candidate compound capable of binding to a eukaryotic Heat Shock RNA (HSR1) or HSF/HSR1/eEF1A ternary complex, said method comprising: (a) contacting the HSR1 or HSF1/HSR1/eEF1A ternary complex with a test compound under conditions that permit binding of the test compound to the HSR1 or HSF1/HSR1/eEF1A ternary complex; and (b) detecting binding of the test compound to the HSR1 or HSF1/HSR1/eEF1A ternary complex. The binding of the test compound to the HSR1 or HSF1/HSR1/eEF1A ternary complex can be detected, e.g., by detecting HSF DNA binding in crude extracts (using, e.g., electrophoretic mobility shift assays (EMSA)), HSP expression (using, e.g., immunochemistry), or cell thermotolerance (using, e.g., MTS cell viability assays). In a specific embodiment, the conditions that permit binding of the test compound to the HSR1 are stress conditions (e.g., heat shock conditions).

The above-identified screening methods can be used to identify a candidate compound that can be used to treat a condition that can be treated by modulating a function of a eukaryotic Heat Shock RNA (HSR1) and/or HSF/HSR1/eEF1A ternary complex. Such conditions include cancer, inflammation, ischemia, neurodegeneration, age-related diseases, HIV infection, deafness, and related disorders.

Test compounds can be selected without limitation from small inorganic and organic molecules (i.e., those molecules of less than about 2 kDa, and more preferably less than about 1 kDa in molecular weight), polypeptides (including native ligands, antibodies, antibody fragments, and other immunospecific molecules), oligonucleotides, polynucleotides, or a chimera or derivative thereof.

As disclosed in Examples, infra, cellular factors that are associated with HSR1 and/or HSF/HSR1/eEF1A complex before and after stress (e.g., heat shock) in vivo can be identified by co-immunoprecipitation (e.g., using antibodies against HSR1 (e.g., modified HSR1), eEF1A or HSF) or in vivo crosslinking with formaldehyde combined with affinity chromatography using biotinylated HSR1-antisense oligonucleotides as a tag.

In addition, compounds that specifically bind to a eukaryotic HSR1 and/or HSF/HSR1/eEF1A ternary complex and/or modulate a function of a eukaryotic HSR1 and/or HSF/

HSR1/eEF1A ternary complex in vivo can be identified using yeast "n-hybrid systems", e.g., yeast one-hybrid system to detect DNA-protein interactions, yeast two-hybrid system to detect protein-protein interactions, yeast RNA-based three-hybrid system to detect RNA-protein interactions, and yeast ligand-based three-hybrid system to detect small molecule-protein interactions, including systems to detect trimeric interactions, ligand-receptor interactions, interactions that require particular post-translational modifications as well as "reverse n-hybrid systems" to identify mutations, peptides or small molecules that dissociate macromolecular interactions. (for review see Vidal and Legrain, Nucleic Acids Res. 1999; 27:919-29). The use of various types of RNA-based three-hybrid system (SenGupta et al., Proc. Natl. Acad. Sci. USA 1996; 93:8496-501) is particularly preferred to identify compounds that interact with HSR1 in vivo.

Compounds that specifically bind to a eukaryotic HSR1 and/or HSF/HSR1/eEF1A ternary complex and/or modulate a function of a eukaryotic HSR1 and/or HSF/HSR1/eEF1A ternary complex can be also identified by high-throughput screening (HTS) assays, including cell-based and cell-free assays, directed against individual targets. Several methods of automated assays that have been developed in recent years enable the screening of tens of thousands of compounds in a short period of time (see, e.g., U.S. Pat. Nos. 5,585,277, 5,679,582, and 6,020,141). Such HTS methods are particularly preferred. One possible approach uses recombinant bacteriophage to produce large libraries. Using the "phage method" (Scott and Smith, Science 1990; 249:386-390; Cwirla, et al., Proc. Natl. Acad. Sci. USA 1990; 87:6378-6382; Devlin et al., Science 1990; 49:404-406), very large libraries can be constructed (106-108 chemical entities). A second possible approach uses primarily chemical methods, of which the Geysen method (Geysen et al., Molecular Immunology 1986; 23:709-715; Geysen et al. J. Immunologic Method 1987; 102:259-274; and the method of Fodor et al. (Science 1991; 251:767-773) are examples. Furka et al. (14th International Congress of Biochemistry, 1988, Volume #5, Abstract FR:013; Furka, Int. J. Peptide Protein Res. 1991; 37:487-493), and U.S. Pat. Nos. 4,631,211 and 5,010,175 describe methods to produce a mixture of peptides that can be tested as agonists or antagonists. In another aspect, synthetic libraries (Needels et al., Proc. Natl. Acad. Sci. USA 1993; 90:10700-4; Ohlmeyer et al., Proc. Natl. Acad. Sci. USA 1993; 90:10922-10926; PCT Publication Nos. WO 92/00252 and WO 94/28028) and the like can be used to screen for candidate compounds according to the present invention.

15. Genetically Modified Animals

Genetically modified animals can be prepared for studying the biological function of HSR1 in vivo and for screening and/or testing candidate compounds for their ability to affect the expression and/or function of HSR1 or HSF/HSR1/eEF1A ternary complex as potential therapeutics for treating cancer, inflammation, ischemia, neurodegeneration, age-related diseases, HIV infection, deafness, and related disorders.

To investigate the function of HSR1 in vivo in animals, HSR1-specific polynucleotides of the invention or modulatory HSR1-specific antisense nucleic acids, RNAi (e.g., shRNA or siRNA), ribozymes, or TFOs can be introduced into test animals, such as mice or rats, using, e.g., viral vectors or naked nucleic acids. Alternatively, transgenic animals can be produced. Specifically, "knock-in" animals with the endogenous HSR1 gene substituted with a heterologous gene or an ortholog from another species or a mutated HSR1 gene, or "knockout" animals with HSR1 gene partially or completely inactivated, or transgenic animals expressing or overexpressing a wild-type or mutated HSR1 gene (e.g., upon targeted or random integration into the genome) can be generated.

HSR1-specific nucleic acids can be introduced into animals using viral delivery systems. Exemplary viruses for production of delivery vectors include without limitation adenovirus, herpes virus, retroviruses, vaccinia virus, and adeno-associated virus (AAV). See, e.g., Becker et al., Meth. Cell Biol. 1994; 43:161-89; Douglas and Curiel, Science & Medicine 1997; 4:44-53; Yeh and Perricaudet, FASEB J. 1997; 11:615-623; Kuo et al., Blood 1993; 82:845; Markowitz et al., J. Virol. 1988; 62:1120; Mann et al., Cell 1983; 33:153; U.S. Pat. Nos. 5,399,346; 4,650,764; 4,980,289; 5,124,263; and International Publication No. WO 95/07358.

In an alternative method, an HSR1-specific nucleic acid can be introduced by liposome-mediated transfection, a technique that provides certain practical advantages, including the molecular targeting of liposomes to specific cells. Directing transfection to particular cell types (also possible with viral vectors) is particularly advantageous in a tissue with cellular heterogeneity, such as the brain, pancreas, liver, and kidney. Lipids may be chemically coupled to other molecules for the purpose of targeting. Targeted peptides (e.g., hormones or neurotransmitters), proteins such as antibodies, or non-peptide molecules can be coupled to liposomes chemically.

In another embodiment, target cells can be removed from an animal, and a nucleic acid can be introduced as a naked construct. The transformed cells can be then re-implanted into the body of the animal. Naked nucleic acid constructs can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., J. Biol. Chem. 1992; 267:963-7; Wu et al., J. Biol. Chem. 1988; 263:14621-4.

In yet another embodiment, HSR1-specific nucleic acids can be introduced into animals by injecting naked plasmid DNA containing a HSR1-specific nucleic acid sequence into the tail vein of animals, in particular mammals (Zhang et al., Hum. Gen. Ther. 1999; 10:1735-7). This injection technique can also be used to introduce siRNA targeted to HSR1 into animals, in particular mammals (Lewis et al., Nature Genetics 2002; 32:105-106).

As specified above, transgenic animals can also be generated. Methods of making transgenic animals are well-known in the art (for transgenic mice see Gene Targeting: A Practical Approach, 2nd Ed., Joyner ed., IRL Press at Oxford University Press, New York, 2000; Manipulating the Mouse Embryo: A Laboratory Manual, Nagy et al. eds., Cold Spring Harbor Press, New York, 2003; Teratocarcinomas and Embryonic Stem Cells: A Practical Approach, Robertson ed., IRL Press at Oxford University Press, 1987; Transgenic Animal Technology: A Laboratory Handbook, Pinkert ed., Academic Press, New York, 1994; Hogan, Manipulating the Mouse Embryo, Cold Spring Harbor Laboratory Press, Cold Spring Harbor, N.Y., 1986; Brinster et al., Proc. Nat. Acad. Sci. USA 1985; 82:4438-4442; Capecchi, Science 1989; 244: 1288-1292; Joyner et al., Nature 1989; 338:153-156; U.S. Pat. Nos. 4,736,866; 4,870,009; 4,873,191; for particle bombardment see U.S. Pat. No. 4,945,050; for transgenic rats see, e.g., Hammer et al., Cell 1990; 63:1099-1112; for non-rodent transgenic mammals and other animals see, e.g., Pursel et al., Science 1989; 244:1281-1288 and Simms et al., Bio/Technology 1988; 6:179-183; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, Robertson ed., IRL Press, 1987). Clones of the nonhuman transgenic animals can be produced according to available methods (see e.g., Wilmut et al., Nature 1997; 385:810-813 and International Publications No. WO 97/07668 and WO 97/07669).

16. EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

a. General Methods

(i) Cell Culture and HS Treatment

HeLa cells (ATCC Accession No. CCL-2) and BHK-21 cells (ATCC Accession No. CRL-1632) were grown at 37° C. in an incubator with 5% $CO_2$. HeLa cells were grown in DMEM containing 10% FBS, 2 mM glutamine and antibiotic/antimycotic cocktail (penicillin/streptomycin/fungizone). BHK-21 cells were maintained in DMEM/F-12 (1:1) mixture supplemented with 10% NBCS, 2 mM glutamine and the same antibiotic cocktail. Heat shock of cultured cells was performed in a water bath adjusted to 43° C. or 45° C. as indicated in the descriptions of figures and related examples. Monolayer cells grown in screw-cap flasks were tightly closed, sealed with parafilm and submerged in the water bath for indicated time periods as indicated in the legends. Corresponding control cells were maintained in tightly closed flasks in the incubator at 37° C.

(ii) Preparation of the Whole Cell Lysate

After removal of medium, cells were scraped into 3 ml (per 75 $cm^2$ flask) of ice-cold PBS and collected by a 5 minute centrifugation at 500×g. Cell pellets were resuspended in ice-cold HEDG buffer (20 mM HEPES-NaOH, pH 7.8, 0.5 mM EDTA, 0.5 mM DTT, 10% glycerol, and protease inhibitor cocktail [Complete™ from Roche, Calif.]) containing 0.42M NaCl at a ratio of 100 µl per confluent 75 $cm^2$ flask, vortexed briefly, and subjected to three cycles of freezing in liquid nitrogen/thawing at room temperature. The lysate was clarified by a 15 minute centrifugation at 25,000×g, divided into small aliquots, flash-frozen and stored at −70° C. Total protein concentration was ~3-5 mg/ml.

(iii) Protein Expression and Purification

The pGex-2T plasmid (Genbank Accession Nos. A01578 and M21676) carrying mouse HSF1 cDNA fused to N-terminal GST was obtained from Dr. K. Sarge (Sarge et al., Mol. Cell Biol. 1993; 13:1392-1407). *E. coli* BL-21 cells were transformed with pGex-2THSF1, grown to $OD_{600}$~0.6, and induced with 0.1 mM IPTG for 5 hours at 28° C. Cells were collected, resuspended in lysis buffer (20 mM tris-Cl, pH 7.9, 0.3 M NaCl and the protease inhibitors cocktail) and sonicated. The lysate was cleared at 35,000×g (20 min) and mixed with 1 ml bed volume of glutathione Sepharose (Amersham) per 1 L of initial bacterial culture (30 min at +4° C.). The beads were washed successively with 3×10 bed volumes of lysis buffer, 2×10 bed volumes of lysis buffer+5 mM ATP+25 mM $MgCl_2$, and 3×10 bed volumes of lysis buffer. For thrombin cleavage of the matrix-bound GST-HSF1, a 50% beads suspension in lysis buffer containing 2.5 mM $CaCl_2$ was incubated with 50 units of thrombin per ml of beads for 12 h at 25° C. on a rotator. Thrombin was inhibited by addition of 0.5 mM PMSF, and the resin washed twice with 1 bed volume of lysis buffer. The fractions were combined and used to prepare HSF1-Sepharose or HSF1 activation studies.

eEF1A was purified from rat liver essentially as described by Kristensen, et al., Biochem. Biophys. Res. Commun. 1998; 245:810-814. Briefly, rat liver was homogenized in a Polytron homogenizer in 4 volumes (v/w) of TEDG buffer (50 mM Tris-HCl, pH 7.9 at 4° C., 0.5 mM EDTA, 0.5 mM DTT, 10% glycerol) containing 50 mM NaCl, centrifuged for 30 min at 35,000×g and filtered through 4 layers of gauze. The lysate was then applied to a Q-Sepharose column equilibrated with TEDG buffer whose output was connected to the input of CM Sepharose column equilibrated in the same buffer. After washing off unbound proteins, the Q-Sepharose column was disconnected and the CM Sepharose column was developed with a linear gradient of 0-0.5 M NaCl in TEDG buffer. Fractions containing eEF1A as determined by SDS-PAGE followed by immunoblotting and/or Coomassie staining were pooled, dialyzed against TEDG/50 mM NaCl and applied to a phosphocellulose P11 column equilibrated with TEDG/50 mM NaCl buffer. A linear gradient of 50-250 mM NaCl in TEDG was applied and fractions were analyzed for the presence of eEF1A as before. Fractions containing eEF1A were pooled and concentrated by ultrafiltration through a10 kDa MWCO membrane. At this stage, the purity of the eEF1A preparation was typically 80-90% as determined by SDS-PAGE.

(iv) HSF1 Immobilization on Cross-Linked Sepharose 4B

HSF1 immobilization on cross-linked Sepharose 4B was performed via imine bond formed in a reaction of lysine residue side chains within the protein with aldehyde groups linked to activated Sepharose. Cross-linked Sepharose CL4B (Sigma-Aldrich, St. Louis, Mo.) was activated by periodate oxidation. The resin was collected by centrifugation and incubated for 5 hours with two bed volumes of 20 mg/ml sodium periodate at room temperature in the dark. The resin was then washed with 5 bed volumes of water followed by wash with 3 bed volumes of 100 mM $NaBO_3$, pH 9.0. Then 3 bed volumes of purified HSF1 in 100 mM $NaBO_3$, pH 9.0 were added and the mixture was incubated for 3 hours at room temperature with continuous inversion mixing. Typical protein concentration used was 0.5-1.5 mg/ml. The resin was sedimented by centrifugation and washed twice with 100 mM $NaBO_3$, pH 8.0. The washes were pooled and protein concentration was determined to estimate the binding efficiency which typically was about 80%. Equal volume of freshly prepared 3 mg/ml sodium borohydrate in 100 mM sodium borate, pH 8.0 was added to Sepharose, incubated 5 minutes on a rotator, diluted 5-fold with 100 mM $NaBO_3$, pH 8.0. The suspension was centrifuged and the supernatant discarded. The resin washed repeatedly with 100 mM $NaBO_3$, pH 8.0 by resuspension/ centrifugation until the pH of the supernatant was approximately 8.0 (as checked by pH paper). Removal of non-specifically bound proteins and blocking of excess reactive groups was achieved by three washes with 0.5 M NaCl in 100 mM ethanolamine, pH 8.0.

(v) Electrophoretic Mobility Shift Assays (EMSA) and Chemical Cross-Linking

EMSA was performed as described by Sarge et al.(Mol. Cell Biol. 1993; 13:1392-1407) with minor modifications. Binding reactions contained 10-20 µg protein sample for the whole cell lysate or 10 ng of purified recombinant HSF1, 20 mM HEPES-NaOH, pH 7.9, 100 mM NaCl, 1.5 mM $MgCl_2$, 0.5 mM EDTA, 2 mM DTT, 10% (v/v) glycerol, 1 mg/ml BSA, 2.5 µg poly(dI-dC), and 1.25 ng of $^{32}$P-end labeled HSE oligonucleotide (5'-GCCTCGAATGTTCGCGAAGT TTCG-3' (SEQ ID NO: 14)) in a final volume of 40 µl. Reactions were incubated for about 20 minutes at room temperature, mixed with 4 µl of 0.02% bromophenol blue in 50% glycerol and loaded onto a 4% PAAG and run in 25 mM Tris, 190 mM glycine, 1 mM EDTA (pH 8.3) at 50 mA until the bromophenol blue reached the bottom of the gel. The gel was dried and analyzed in a phosphorimager.

Purified HSF1 (10 nM) was incubated with eEF1A and HSR1 at the indicated concentrations. The crosslinking reagent EGS (Pierce, Rockford, Ill.) was added to 0.2-0.5 mM in the same buffer used for EMSA for 30 min at room temperature. Reactions were quenched with 75 mM glycine and processed for immunoblotting.

(vi) HSF-Sepharose Pull Down Experiments and Preparation of HSR1

Whole cell lysates were prepared as described above and diluted with HEDG buffer to give the final salt concentration of about 0.21 M NaCl. A bed volume of 10 µl of HSF-Sepharose beads per 75 $cm^2$ flask of confluent cells was added and mixed on a rotator at 4° C. for 2-4 hours. Beads were collected by 5 minute centrifugation at 500×g and washed three times with 10 bed volumes of HEDG containing 0.21 M NaCl by resuspension/centrifugation. Elution was performed by incubation of the beads with one bed volume of HEDG containing 0.21 M NaCl at 43° C. for 30 minutes on a rotator. Three successive elutions were performed and the obtained fractions were analyzed by SDS-PAGE.

To prepare HSR1, eEF1A-containing fractions were pooled, supplemented with 12.5 mM EDTA and 0.25% SDS and treated with 6,000 units of proteinase K (Fermentas, Hanover, Md.) for 30 minutes at 50° C. RNA was then extracted twice with phenol-chloroform and precipitated with isopropanol.

(vii) Transfection and Cell Viability Assay

The oligos (IDT) used for transfection, $6^{HSR1}$ (5'-AGT CCT CAC ACC ACT CCA ACG TCT GCT TAT GGC GGC GGA TTC AAC-3') (SEQ ID NO: 12) and anti-$6^{HSR1}$ (5'-GTT GAA TCC GCC GCC ATA AGC AGA CGT TGG AGT GGT GTG AGG ACT-3') (SEQ ID NO: 13), were phosphothioate modified at 3' and 5' ends to increase their stability. In the experiment shown in FIG. 6A, $6^{HSR1}$ oligo or $6^{HSR1}$/anti-$6^{HSR1}$ double-stranded oligo (0.56 µM final concentration) were used to transfect BHK cells using Superfect reagent (Qiagen, Valencia, Calif.) according to the manufacturer's instructions. The day following transfection, cells were heat shocked for 1 hour at 43° C. and a whole cell lysate was prepared to determine HSF1 activity. In some experiments, cells were allowed to recover at 37° C. overnight after heat shock to allow synthesis of HSPs. Next, a whole cell lysate was prepared and analyzed by immunoblotting using HSP72 antibodies (Stressgen, Canada) that specifically recognize only the inducible form of HSP70.

In the experiment shown in FIG. 6B, cells were seeded in 24-well plates at a density of 3-5×10$^4$ cells per well. The following day, cells (about 75% confluent) were transfected using Oligofectamine reagent (Invitrogen, Carlsbad, Calif.) and the final oligo concentration of 100 nM according to the manufacturer's instructions. Transfections were performed in groups of four wells. Cell viability was determined using the MTS reagent-based CellTiter 96® AQueous Non-Radioactive Cell Proliferation Assay (Promega, Madison, Wis.). The efficiency of transfection was estimated by transfecting BHK and HeLa cells with Cy5-labeled $6^{HSR1}$ oligonucleotide (IDT) and counting the percentage of fluorescently labeled cells. Normalization of the survival data for the efficiency of transfection was done according to the following transformation: $S_{norm}=100-(100-S)/E$, where $S_{norm}$ represents the normalized percentage of surviving cells, S represents the original percentage of surviving cells, and E represents efficiency of transfection. E was estimated to be 0.3 for BHK and 0.7 for HeLa cells.

(viii) Reporter Plasmid Constructs

A reporter plasmid carrying the *Renilla* luciferase gene under the control of the human HSP70B promoter was constructed by cloning the 2.3 kb HindIII-XhoI fragment of the p173OR vector (Stressgen, Canada) into the HindIII-XhoI digested pMLuc vector (Novagen, San Diego, Calif.). The resulting pMLucHSP70 plasmid displayed at least 200- and 100-fold induction of RLuc activity in HeLa and BHK cells, respectively, under the HS conditions used (typically, 2 hours at 43° C. followed by 12-16 hours of recovery at 37° C.).

(ix) siRNA Experiments

In siRNA experiments, cells were transfected in 12-well plates with a mixture of 100 ng pMLucHSP70, 250 ng siRNA construct and 50 ng pSV40bGal (Promega, Madison, Wis.) (as an internal control for the transfection efficiency) using Effectene reagent (Qiagen, Valencia, Calif.) according to manufacturer's instructions. Cells were incubated with the transfection complexes for 24 hours, heat shocked for 2 hr at 43° C. and allowed to recover at 37° C. for 12-16 hr.

Measurement of RLuc activity was performed in whole cell lysates using a *Renilla* luciferase activity assay kit (Promega, Madison, Wis.). Briefly, cells were rinsed with ice-cold PBS to remove traces of medium and incubated with 150 µl per well of HEDG buffer containing 0.42 M NaCl and 0.25% Triton X-100. Lysates were then clarified by centrifugation at 25,000×g for 15 minutes and 4 µl aliquots were used for RLuc activity assays.

The retroviral vector pBNsGFP is a modified derivative of pBabeNeo and carries the cDNA for enhanced green fluorescent protein (EGFP) as describes in Morgenstern and Land (Nucleic Acids Res. 1990; 18: 3587-3596). For siRNA experiments, a cassette containing the H1 promoter followed by a short hairpin-encoding fragment (siHSR1-224) GATC-CCCGGAGTGGTGTGAGGACTACTTCAA-GAGAGTAGTCCTCACACCACTCCTTTTT GGAAA (SEQ ID NO: 16) was excised from pSuper vector (OligoEngine, Inc., Seattle, Wash.) and cloned to replace GFP. Similarly, an antisense expression construct was generated by replacing the GFP cDNA with 604 bp HSR1 cDNA in the antisense orientation in respect to the LTR promoter. VSV-G-pseudotyped virus was produced using the Retro-X packaging system (Clontech, Inc.). Infected BHK and HeLa cells were selected for G418 resistance. At least $10^3$ independent colonies were obtained from each infection experiment; these were pooled for further analysis. Transient transfection with RLuc bGal reporter plasmids, heat shock treatment, and reporter gene activity assays were performed as described above for transient transfections.

Example 1

Identification of eEF1A as HSF-Associated Factor that Stimulates its Activation

Figure 1:
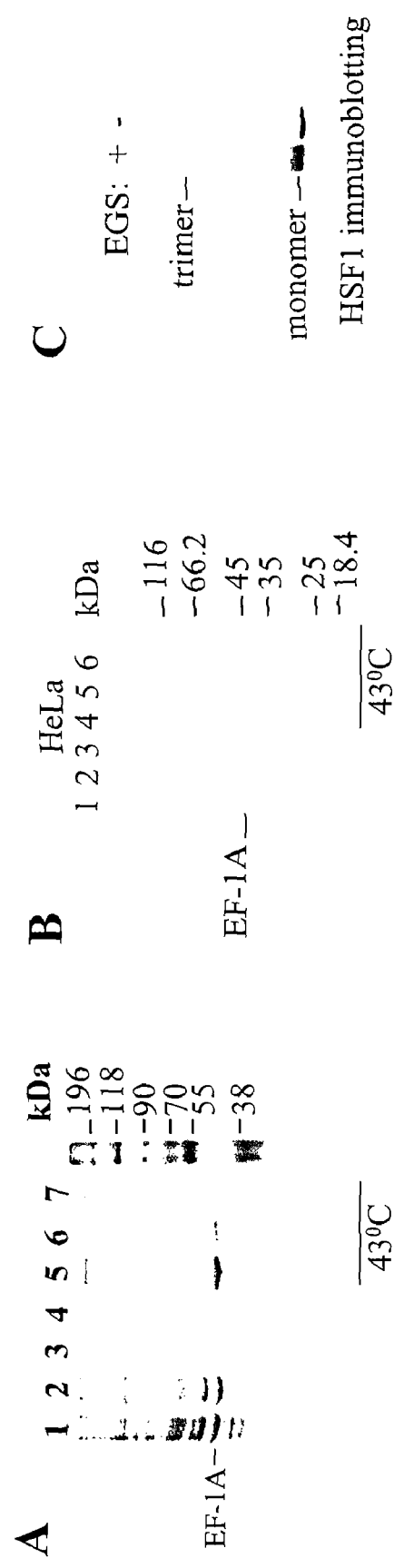
FIGS. 1A-B represent SDS-PAGE analysis of the proteins from the lysate of heat shocked BHK-21 (A) or HeLa (B) cells that interact with bacterially expressed GST-HSF1 immobilized on glutathione Sepharose. A. Lane 1: the whole lysate of heat shocked BHK cells; lane 2: supernatant after the incubation of the lysate of heat shocked BHK cells with HSF1 Sepharose beads; lane 3: proteins bound to HSF1 Sepharose after the incubation with the lysate of heat shocked BHK cells and washing; lane 4: proteins bound to HSF1 Sepharose following three successive rounds of elution at 43° C.; lanes 5-7: proteins released from HSF1 Sepharose in three successive rounds of elution at 43° C. B. Lane 1: supernatant after the incubation of the lysate of heat shocked HeLa cells with HSF1 Sepharose beads; lane 2: proteins bound to HSF1 Sepharose after the incubation with the lysate of heat shocked HeLa cells and washing; lane 3: proteins bound to HSF1 Sepharose following three successive rounds of elution at 43° C.; lanes 4-6: proteins released from HSF1 Sepharose in three successive rounds of elution at 43° C. The analysis reveals a polypeptide of about 45 kDa which was retained on HSF1 Sepharose after incubation with the lysate of heat shocked BHK-21 or HeLa cells but not from the lysate of unstressed cells.
FIG. 1C represents Western blotting analysis of purified recombinant HSF used in pull-down experiments (using anti-HSF1 monoclonal antibody from Stresgene Co.) showing that HSF1 coupled to Sepharose was predominantly in monomeric form (with negligibly low amount of trimers). Where indicated, cross-linking was performed using 0.5 mM EGS.

To identify putative auxiliary factors involved in the activation of HSF1 in the lysate of heat shocked cells, the present inventors looked at proteins from whole cell lysates retained on covalently immobilized HSF1. Mouse HSF1 was expressed in *E. coli* as a fusion protein with GST (glutathione-S-transferase). Induction of GST-HSF1 synthesis was performed at 28° C. and care was taken not to exceed an HSF concentration of 0.5 mg/ml during purification so as to minimize spontaneous trimerization. No trimers were detected in our purified recombinant HSF upon examination by chemical cross-linking (FIG. 1C). Purified HSF1 was covalently attached to Sepharose beads. A polypeptide of approximately 45 kDa was retained on HSF1-Sepharose after incubation with a lysate from heat shocked, but not from untreated, BHK-21 (FIG. 1A) or HeLa cells (FIG. 1B). FIG. 1A shows fractionation of lysates of heat shocked BHK cells and FIG. 1B shows fractionation of lysates of heat shocked HeLa cells on HSF1-Sepharose. In FIG. 1A, lane 1 shows a whole cell lysate of heat shocked BHK cells; lane 2 shows the supernatant after incubation of BHK lysates with HSF1 Sepharose; lanes 3 show HSF1 Sepharose beads incubated with the lysates and washed; lanes 4 show HSF1-Sepharose beads after three successive rounds of elution at 43° C.; lanes 5-7 show proteins released from HSF1-Sepharose after successive rounds of elution at 43° C. In FIG. 1B, lane 1 shows supernatant after the incubation of the lysate of heat shocked HeLa cells with HSF1 Sepharose beads; lane 2 shows proteins bound to HSF1 Sepharose after the incubation with the lysate of heat shocked HeLa cells and washing; lane 3 shows proteins bound to HSF1 Sepharose following three successive rounds of elution at 43° C.; lanes 4-6 show proteins released from HSF1 Sepharose in three successive rounds of elution at 43° C. Immunoblotting (FIG. 1C) shows that HSF1 coupled to Sepharose was predominantly in monomeric form. Where indicated, cross-linking was performed using 0.5 mM EGS.

The bound polypeptide was identified by MALDI-TOF analysis (performed at NYU Mass Spectrometry Facility) as translation elongation factor eEF1A. Similar results were also obtained with GST-HSF1 fusion protein immobilized on glutathione Sepharose beads, demonstrating that chemical modifications associated with protein immobilization did not alter the ability of HSF1 to interact with eEF1A.

The retention of eEF1A on HSF-Sepharose was temperature-sensitive: incubation at 43° C. caused the release of most of the bound eEF1A (FIG. 1A, lanes 5-7 for BHK and FIG. 1B, lanes 4-6 for HeLa cells). No eEF1A binding was observed if BSA-Sepharose was used instead of HSF-Sepharose. The eEF1A polypeptide could be eluted by incubating the resin at 43° C., a typical heat shock temperature for mammalian cells.

Figure 2:
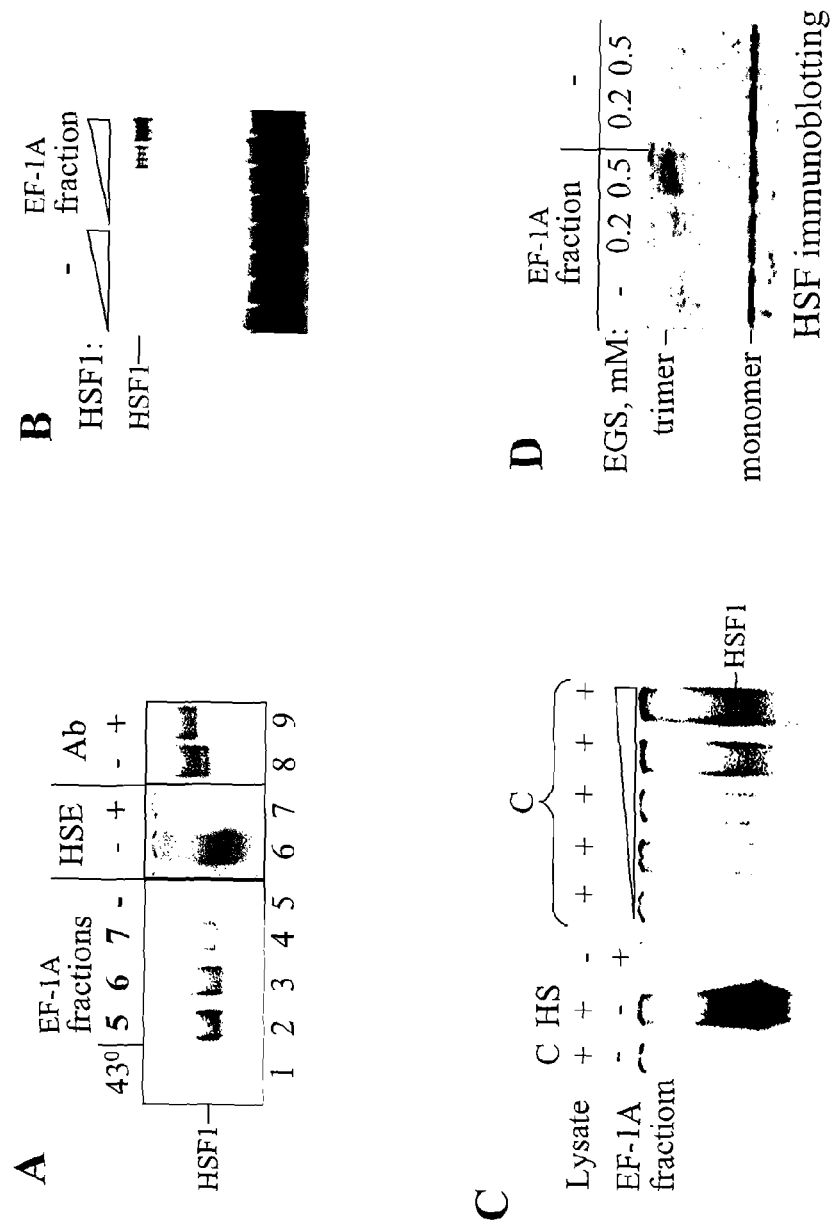
FIGS. 2A-C represent electrophoretic gel mobility shift assays (EMSA) of in vitro induction of HSF1 DNA binding by the HSF1-interacting fraction from the lysate of heat shocked BHK cells. A. EMSA of the whole cell lysate of unstressed BHK cells (20 µg) incubated in the absence (lane 1, 5) or in the presence (lanes 2-4) of fractions 5-7 from FIG. 1A. "43°" in lane 1 indicates that the lysate was heat-shocked for 15 min prior to EMSA. Lanes 6-9 contain fraction 5 from FIG. 1A. "HSE" (lanes 6-7) indicates the inclusion of an excess of unlabeled HSE oligonucleotide. "Ab" (lanes 8-9) indicates the presence of a monoclonal anti-HSF1 antibody that causes a supershift (lane 9). This EMSA demonstrates that the eEF1A-containing fraction from the lysate of heat shocked BHK cells activates endogenous HSF1 in a lysate from unstressed BHK cells. As shown in lanes 6-9, this activity is specific. B. EMSA of the increasing amounts of purified recombinant mouse HSF1 incubated in the absence (−) or presence of the eEF1A-containing fraction from the lysate of heat shocked BHK cells isolated on HSF1-Sepharose (see FIG. 1). C. EMSA showing a dose-dependent activation of HSF1 in a lysate of unstressed BHK cells after 20 µg of a lysate of unstressed (C) or heat shocked (HS) cells were incubated with increasing amounts of the eEF1A-containing fraction (1-10 µl). EMSA in B and C demonstrate that the eEF1A-containing fraction from the lysate of heat shocked BHK cells induces DNA binding activity of HSF1, and this effect is dose-dependent with respect to both the amount of pure HSF1 (B) or cell lysate (C) and the eEF1A-containing fraction.
FIG. 2D represents Western blotting analysis of purified recombinant mouse HSF1 incubated in the absence (−) or presence of the eEF1A-containing fraction, followed by cross-linking with EGS. After separation of proteins by SDS-PAGE and transfer to nitrocellulose membrane, the blot was probed with an anti-HSF1 8487 polyclonal antibody. The immunoblotting demonstrates that the eEF1A-containing fraction induces trimerization of purified recombinant HSF1.

The eEF1A-containing fraction eluted by heat from HSF-Sepharose was tested to determine whether it has any effect on HSF1 function in vitro. Remarkably, the eEF1A fraction was able to activate endogenous HSF1 in the lysate of unstressed cells as assayed by electrophoretic gel mobility shift assays (EMSA) (FIG. 2A). An aliquot of a whole cell lysate of unstressed BHK cells (20 µg) was incubated in the absence (lane 1, 5) or in the presence (lanes 2-4) of fractions 5-7 from FIG. 1A. "43°" in lane 1 indicates that the lysate was heat-shocked for 15 min prior to EMSA. Lanes 6-9 contained fraction 5 from FIG. 1A. "HSE" (lanes 6-7) indicates the inclusion of an excess of unlabeled HSE oligonucleotide. "Ab" (lanes 8-9) indicates the presence of a monoclonal anti-HSF1 antibody that causes a supershift (lane 9). Purified HSF1 (10 nM) was incubated with eEF1A and HSR1 at the indicated concentrations. The crosslinking reagent EGS (Pierce) was added to 0.2-0.5 mM in the same buffer used for EMSA for 30 min at room temperature. Reactions were quenched with 75 mM glycine and processed for immunoblotting.

Additionally, this eEF1A fraction induced DNA-binding activity of recombinant HSF1 (FIG. 2B). The effect was dose-dependent with respect to both the amount of pure HSF1 (or cell lysate, FIG. 2C) and the eEF1A fraction (FIG. 2B). FIG. 2B shows in vitro activation of recombinant HSF1 by the eEF1A fraction. Increasing amounts of purified recombinant mouse HSF1 were incubated in the absence (−) or presence of the eEF1A fraction and analyzed by EMSA. FIG. 2C shows dose-dependent activation of HSF1 in a lysate of unstressed BHK cells. 20 µg of a lysate of unstressed (C) or heat shocked (HS) cells were incubated with increasing amounts of the eEF1A fraction (1-10 µl) and subjected to EMSA.

Contrary to previous reports (Guo et al., J. Biol. Chem. 2001; 276:45791-45799), heating lysates from unstressed cells in the absence of the eEF1A fraction did not yield any detectable HSF1 activity (FIG. 2A, lane 5). Possible reasons for this discrepancy are discussed below. The induced HSF1 DNA binding activity was specific, since it was sensitive to both an anti-HSF antibody and an excess of unlabeled HSE oligonucleotide (FIG. 2A, lane 6, 7 and 8, 9). Activation of purified HSF1 by the eEF1A fraction was accompanied by trimerization of HSF as confirmed by protein-protein chemical crosslinking (FIG. 2D). FIG. 2D shows that the eEF1A fraction induces trimerization of purified recombinant HSF1. Purified recombinant mouse HSF1 was incubated in the absence (−) or presence of the eEF1A containing fraction and the cross-linking reagent EGS. Proteins were then separated by SDS-PAGE, transferred to nitrocellulose membrane, and probed with an anti-HSF1 antibody.

Figure 3:
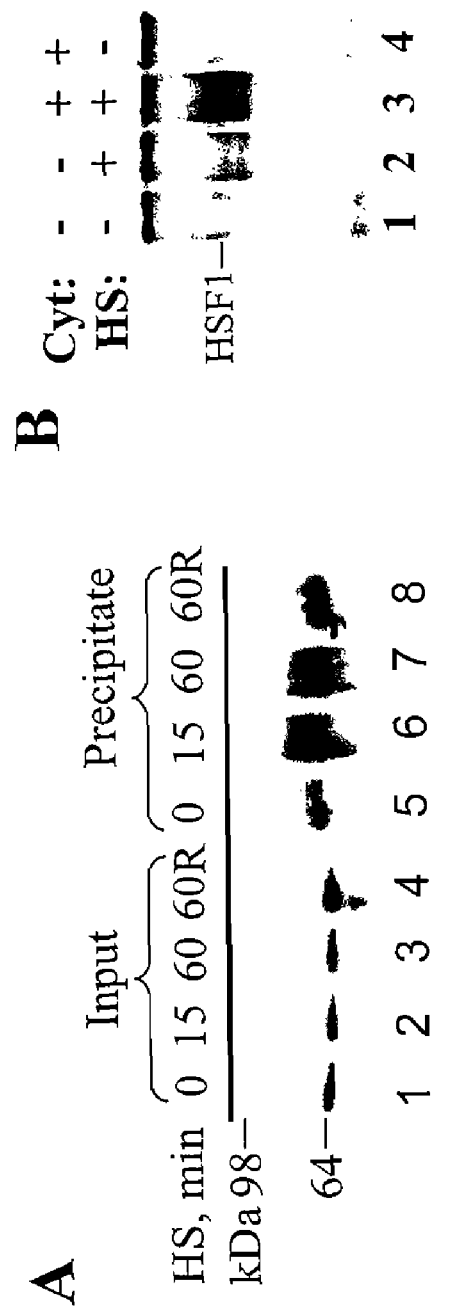
FIG. 3A represents Western blotting analysis of co-immunoprecipitation of eEF1A and HSF1 demonstrating formation of an eEF1A-HSF1 complex in vivo. BHK cells were heat shocked for the indicated periods of time, whole cell lysates were prepared and eEF1A was immunoprecipitated with anti-eEF1A antibody, followed by SDS-PAGE and immunoblotting with anti-HSF1 8487 polyclonal antibody. 0-60 min: duration of the heat shock treatment at 43° C.; 60R: 60 min heat shock followed by recovery for 60 min at 37° C.
FIG. 3B represents electrophoretic gel mobility shift assays (EMSA) showing the effect of cytochalasin on HSF1 activation by HS. HeLa cells were incubated with 10 µM cytochalasin ("Cyt"; lanes 3, 4) and either subjected to 1 h HS at 43° C. (lanes 2, 3) or maintained at 37° C. (lanes 1, 4). Whole cell lysates were then prepared and assayed by EMSA. The EMSA demonstrates that, while cytochalasin does not affect HSF1 binding to DNA in the absence of HS (lane 4), its addition 1 h prior to exposure of cells to HS results in a dramatic increase in HSF activity (lanes 2 and 3).

The interaction between HSF1 and eEF1A in vivo was confirmed in an experiment in which eEF1A and HSF1 were co-immunoprecipitated from a whole cell lysate (FIG. 3A). In these experiments, BHK cells were heat shocked for the times indicated (HS) and the whole cell lysates analyzed by immunoprecipitation with an anti-eEF1A antibody followed by immunoblotting with anti-HSF1. In FIG. 3A, "60R" indicates 60 min recovery after 60 min HS. Anti-HSF1 immunoblotting revealed a small amount of HSF1 coprecipitating with eEF1A from unstressed cells (FIG. 3A, lanes 1-4). This amount increased steadily upon exposure to heat shock (HS) at 43° C., reaching a plateau within 30 minutes of the temperature shift (FIG. 3A, lanes 6-7). Recovery at 37° C. for 1 hour resulted in almost complete restoration of the initial low level of co-precipitated HSF1 (FIG. 3A, lane 8). The apparent inconsistency of these results with the observation that eEF1A is eluted from HSF-Sepharose at 43° C. (FIGS. 1A-B) is explained by the fact that HSF1 was coupled to Sepharose in the inactive monomeric form (FIG. 1C), suggesting that the affinity of eEF1A for the HSF1 trimer may be greater than its affinity for an HSF1 monomer. The release of HSF1 from the inhibitory multichaperone complex during HS (Zou et al., Cell 1998; 94:471-480) could also potentially contribute to the factor's greater availability for binding to eEF1A. In unstressed cells, most HSF1 would be expected to be associated with HSP90, while most eEF1A would be sequestered by the cytoskeleton and translational machinery. Indeed, eEF1A has been implicated in a number of cellular processes besides protein biosynthesis: it binds actin filaments, genomic RNA of certain viruses, and some transcription factors (Negrutskii et al. Prog. Nucleic Acid. Res. Mol. Biol. 1998; 60:47-78; Izawa et al. Biochem. Biophys. Res. Commun. 2000; 278:72-78; Blackwell et al., J. Virol. 1997; 71:6433-6444; Murray et al., J. Cell Biol. 1996; 135:1309-1321). Free eEF1A may accumulate in the cell under HS conditions due to general translational shut down (Panniers, Biochimie 1994; 76:737-747) and as a result of cytoskeletal collapse (Welch et al., J. Cell. Biol. 1985; 101:1198-1211; Welch et al., Ann. N.Y. Acad. Sci. 1985; 455:57-67). These events would ensure the availability of eEF1A molecules that are capable of forming a complex with HSF1, and thus link the major cellular perturbations caused by HS and HSF1 activation.

To examine whether cytoskeleton-associated eEF1A was implicated in HSF activation, we treated cells with cytochalasin before subjecting them to HS. Cytochalasin is an alkaloid that binds to the + end of F-actin and prevents actin polymerization, causing the cytoskeleton to collapse (Cooper, J. Cell Biol. 1987; 105:1473-1478). As shown in FIG. 3B, cytochalasin does not affect HSF1 binding to DNA in the absence of HS (lane 4). However, addition of cytochalasin 1 h prior to exposure of cells to HS results in a dramatic increase in HSF activity (lanes 2 and 3). In these experiments, HeLa cells were incubated with 10 μM cytochalasin (FIG. 3B, lanes 3, 4) and either subjected to 1 hour HS at 43° C. (FIG. 3B, lanes 2, 3) or maintained at 37° C. (FIG. 3B, lanes 1, 4). Whole cell lysates were prepared and assayed by EMSA. These results are consistent with the hypothesis that eEF1A derived from the collapsing cytoskeleton contributes to HSF activation. At the same time, failure of cytochalasin to promote HSF activation in the absence of stress suggests that yet another factor is required for the eEF1A/HSF complex to become responsive to HS.

Example 2

Isolation OF HSR1 RNA and Determination of its Role in HSF1 Activation

Initial attempts to activate HSF1 with pure eEF1A isolated from rat liver or HeLa cells were unsuccessful, suggesting that the eEF1A-fraction eluted from HSF-Sepharose contained one or more additional unidentified component(s) required for HSF1 activation. Since eEF1A forms a complex with aminoacyl-tRNA in vivo, this interaction was evaluated for its role in activating HSF1. As shown in FIG. 4A, HSF1 binding to DNA was strongly inhibited in vitro by pre-incubation of whole cell BHK lysate with ribonuclease A (RNAseA). The effect was specific, since addition of excess tRNA prior to the ribonuclease treatment protected the HSF activity. The lysate (10 μg of total protein) was treated with 500 ng RNase A for 1 hour at 37° C. with or without excess tRNA. The amount of HSF1 in each lane was monitored by immunoblotting as shown in the lower panel of FIG. 4A. Similar results were obtained using micrococcal nuclease in the presence of $Ca^{2+}$.

These results prompted the present inventors to search for a specific RNA in the eEF1A fraction that participates in HSF1 activation. eEF1A containing fraction was treated with proteinase K in the presence of SDS, extracted twice with phenol:chloroform mixture and ethanol precipitated in the presence of glycogen as a carrier. Silver staining of the resulting preparation that was run on a polyacrylamide denaturing gel (8 M urea), revealed a single band of about 2 kb, demonstrating that it was not tRNA (FIG. 4B). The band (termed "Heat Shock RNA" or "HSR1") was sensitive to ribonuclease A, but not to deoxyribonuclease I (FIG. 4B). FIG. 4B shows the silver stained denaturing 4% PAGE of the RNA isolated from pooled eEF1A containing fractions (left panel). Where indicated HSR1 samples were treated for 30 min at 25° C. with DNase I (10 U) or RNase A (100 ng) before loading onto the gel (right panel).

Addition of purified HSR1 (but not total RNA) to the lysate of heat-shocked BHK cells treated sequentially with micrococcal nuclease (MNase) (to remove endogenous HSR1) and EGTA (to inactivate the nuclease) restored the DNA binding activity of HSF1 (FIG. 4C). FIG. 4C shows EMSA of HSF1 from lysates of heat shocked BHK cells (20 μg) that were treated sequentially with MNase, EGTA (to inactivate MNase) (lane 1), HSR1 (lane 2) or total RNA (lane 3).

Northern blot analysis showed that HSR1 is constitutively expressed in BHK and HeLa cells and that its level remains unchanged during HS (FIG. 4D). The Northern blot analysis of HSR1 expression in BHK and HeLa cells was performed as follows. Total RNA (10 μg) from either heat shocked (HS) or unstressed (C) BHK or HeLa cells was subjected to electrophoresis in a denaturing agarose gel, transferred to a membrane, and probed with [$^{32}$P]-labeled RNA probe corresponding to region 167-405 of HSR1 (SEQ ID NO: 4). An 18S RNA probe was used for normalization purposes. The inability of HSR1 to bind to various types of oligo(dT) resin indicates that this RNA is not polyadenylated in vivo, and is likely to be untranslated.

Results similar to those described in Examples 1 and 2 were obtained with Drosophila Kc cells. Briefly, incubation of the lysate of heat shocked (1 h at 33° C. ) Kc cells with either mouse HSF1 or Drosophila HSF resulted in binding of eEF1A to the beads. The protein was eluted by heating at 43° C. for 30 min and the resulting fraction contained RNA similar in size to HSR1 isolated from BHK and HeLa cells. The RNA was capable of re-activating HSF in the in vitro system after ribonuclease treatment, suggesting that the RNA-dependent mechanism of HSF activation is conserved among eukaryotes.

Example 3

Cloning, Expression and Functional Analysis of HSR1 cDNAs of HSR1 were cloned from both HeLa and BHK cells (see Methods), and the coding strand was identified in a functional assay (FIG. 5A). As shown in the upper panel of FIG. 5A, the sense (T3) and antisense (T7) HSR1s were transcribed in vitro by T3 and T7 RNA polymerases, respectively, from PCR fragments carrying T3 or T7 promoters on each side of HSR1. The resulting synthetic RNAs were tested in the minimal HSF1 activating system (FIG. 5A, lower panel). For the reconstitution experiment shown in FIG. 5A, recombinant mouse HSF1 was used along with eEF1A purified from rat liver (as described above). HSR1 isolated from heat-shocked BHK or HeLa cells (lanes 7, 8) and HSR1-T3 (lane 10) activated HSF when added together with purified eEF1A. However, neither component alone was capable of activating HSF1 (lanes 2-6). The slight stimulating effect of isolated eEF1A (lane 2) on HSF1 activation results from the residual amount of co-purified HSR1, and could be eliminated by RNAse A treatment. In FIG. 5A, quantitation of HSF1 activation is presented as the fold increase relative to a background control. Under these conditions, about 5% of the total HSF1 was activated.

Crosslinking with ethylene glycol-bis-succinimidylsuccinate (EGS) confirmed that HSR1-T3-mediated activation was accompanied by HSF1 trimerization in vitro (FIG. 5B). In these experiments, purified recombinant HSF1 was incubated with eEF1A with (FIG. 5B; lanes 2-4) or without (lane 1) HSR1-T3 in the presence (lane 2) or absence (lanes 1, 3, 4) of RNase A, followed by cross-linking with indicated concentrations of EGS, and immunoblotting using an HSF1 antibody.

In contrast, HSR1-T7 not only failed to induce any significant HSF1 binding to DNA (FIG. 5A, lane 9), but also suppressed the activating effect of HSR1-T3 (FIG. 5A, lane 11). These data show that HSR1-T3 represents the sense strand of HSR1 and that this is sufficient to support HSF1 activation.

Notably, the mobility of HSR1-T3 depended on the conditions to which it was exposed prior to electrophoresis analysis. Both $Mg^{2+}$ and elevated temperature caused in vitro synthesized HSR1 to migrate similarly to HSR1 isolated from HS cells (FIG. 5C, compare lanes 1 and 2, 3). This conformational change of HSR1 may be associated with triggering HSF1 activation, as only the slow-migrating form of HSR1 was retained on HSF1 Sepharose (FIG. 4B). To eliminate the possibility of RNA processing as a cause of variability in HSR1 mobility, PCR analysis of genomic DNA using HSR1-specific primers was performed. The product obtained with both BHK and HeLa genomic DNA was about 600 nt long. Sequence comparison of the PCR products from BHK and HeLa cells revealed a high degree of identity, with only a 4 nt difference in the PCR products.

Additional evidence of in vivo complex formation between HSF1, eEF1A and HSR1 was obtained from co-immunoprecipitation experiments (FIG. 5D). Immunoprecipitation was performed using an anti-eEF1A antibody as in the experiment shown in FIG. 3A, with the exception that the cells were heat shocked for 1 h. RNA was extracted from the precipitate, and HSR1 was detected by RT-PCR. Since a greater amount of HSR1 was precipitated from HS cells compared to a control (lanes 3 and 4, FIG. 5D), more HSR1/eEF1A complex is likely to form in cells subjected to stress. On the other hand, the presence of HSR1 in the precipitate from control cells may indicate that eEF1A/HSR1 complex is pre-assembled under normal conditions.

Example 4

Suppression of HSF1 Activity by HSR1 Antisense Oligonuclotides

To delineate functional domains within HSR1 that are essential for its HSF-activating function, a set of 15 overlapping 45-mer antisense oligonucleotides covering the entire length of the cloned hamster HSR1 were synthesized (FIG. 5E). Each oligo was tested in the reconstituted system for its ability to suppress HSF1 activation by HSR1/eEF1A. The results of this experiment identified at least two domains in HSR1 that were essential for HSF1 activation. Four out of 15 oligonucleotides, $1^{HSR1}$ (SEQ ID NO: 9; complementary to hamster HSR1 [SEQ ID NO: 1] nt 1-44), $2^{HSR1}$ (SEQ ID NO: 10; complementary to hamster HSR1 [SEQ ID NO: 1] nt 40-84), $5^{HSR1}$ (SEQ ID NO: 11; complementary to hamster HSR1 [SEQ ID NO: 1] nt 157-201), $6^{HSR1}$ (SEQ ID NO: 12; complementary to hamster HSR1 [SEQ ID NO: 1] nt 196-240), spanning 5'-terminal and nt 157-240 segments of the cloned hamster HSR1 (SEQ ID NO: 1), respectively, inhibited HSF1 activation by more than 90% in the in vitro reconstituted system (FIG. 5E).

A phosphothioate derivative of the oligonucleotide $6^{HSR1}$ (complementary to bases 196-240; SEQ ID NO: 12) with the strongest negative effect on HSF activation in vitro was used to transfect BHK and HeLa cells in order to examine its effect on HSF1 activation in vivo. BHK cells were transfected with $6^{HSR1}$ or a control double stranded oligo ($6^{HSR1}$/anti-$6^{HSR1}$), followed by HS treatment. To assess HSF1 activation, a whole cell lysate was prepared immediately following HS treatment and subjected to electrophoretic mobility shift analysis (EMSA) (FIG. 6A). In parallel, we monitored the effect of $6^{HSR1}$ on HSP72 synthesis in vivo. In this case, BHK cells were allowed to recover at 37° C. for 16 hours after HS. A whole cell lysate was then prepared and analyzed for HSP72 expression by immunoblotting (lower panel). As shown in FIG. 6A, $6^{HSR1}$, but not $6^{HSR1}$/anti-$6^{HSR1}$, inhibited activation of HSF1 in vivo as well as the production of HSP72 in response to HS.

Consistent with these data, the antisense HSR1 oligo also compromised cell survival after HS (FIG. 6B). To avoid potential toxic effects of exogenous DNA during transfection, the oligo concentration was decreased six-fold (to 100 nM) compared to the previous experiment. Thermotolerance was induced by heat shocking cells at 43° C. for 1 h, followed by a 12 h recovery at 37° C. to allow HSP synthesis and a second lethal HS challenge (0.5-2 h at 45° C.). Cell viability was determined by the MTS-based assay and normalized to the efficiency of transfection (see Methods). As shown in FIG. 6B, transfection with 6HSR1 resulted in more than 80% lethality after 60 min of 45° C. HS, while the control anti-$6^{HSR1}$ oligo did not exhibit any significant effect on cell viability. Similar results were obtained with HeLa cells.

Independent evidence for a role for HSR1 in the HS response in vivo was obtained via RNAi experiments. Based on data obtained with antisense oligos, vectors expressing siRNA against different parts of HSR1 (siHSR1) were constructed.

Sequences corresponding to HSR1 are grayed out:

```
siHSR1-160 (ds 64-mer, cloned into BglII/HindIII digested pSuper)
5'-GATCCCCCGGCCTGGGCCGTGTCATATTCAAGAGATATGACACGGCCCAGGCCGTTTTTGGAAA    -3'
3'-    GGGGCCGGACCCGGCACAGTATAAGTTCTCTATACTGTGCCGGGTCCGGCAAAAACCTTTTCGA-5'

Sense sequence:       CGGCCTGGGCCGTGTCATA  (SEQ ID NO: 7)
Antisense sequence:   TATGACACGGCCCAGGCCG  (SEQ ID NO: 22)

Stem-loop sequence:   CGGCCTGGGCCGTGTCATATTCAAGAGATATGACACGGCCCAGGCCG (SEQ ID NO: 27)
```

Sequences corresponding to HSR1 are grayed out:

```
siHSR1-224 (ds 64-mer, cloned into BglII/HindIII digested pSuper; this construct
corresponds to 6^HSR1 antisense oligo.)
5'-GATCCCCGGAGTGGTGTGAGGACTACTTCAAGAGAGTAGTCCTCACACCACTCCTTTTTGGAAA     -3'
3'-    GGGCCCTCACCACACTCCTGATGAAGTTCTCTCATCAGGAGTGTGGTGAGGAAAAACCTTTTCGA-5'

Sense HSR sequence:     GGAGTGGTGTGAGGACTAC (SEQ ID NO: 20)
Antisense HSR sequence: GTAGTCCTCACACCACTCC (SEQ ID NO: 24)

Stem-loop sequence: GGAGTGGTGTGAGGACTACTTCAAGAGAGTAGTCCTCACACCACTCC (SEQ ID NO: 28)

mut160: C11 ⟶ G (ds 64-mer, cloned into BglII/HindIII digested pSuper)
5'-GATCCCCCGGCCTGGGCGGTGTCATATTCAAGAGATATGACACCGCCCAGGCCGTTTTTGGAAA     -3'
3'-    GGGGCCGGACCCGCCACAGTATAAGTTCTCTATACTGTGGCGGGTCCGGCAAAAACCTTTTCGA-5'

Sense HSR sequence:     CGGCCTGGGCGGTGTCATA (SEQ ID NO: 8)
Antisense HSR sequence: TATGACACCGCCCAGGCCG (SEQ ID NO: 23)

Stem-loop sequence: CGGCCTGGGCGGTGTCATATTCAAGAGATATGACACCGCCCAGGCCG (SEQ ID NO: 29)

mut224: G4 ⟶ C (ds 64-mer, cloned into BglII/HindIII digested pSuper)
5'-GATCCCCGGACTGGTGTGAGGACTACTTCAAGAGAGTAGTCCTCACACCAGTCCTTTTTGGAAA     -3'
3'-    GGGCCTGACCACACTCCTGATGAAGTTCTCTCATCAGGAGTGTGGTCAGGAAAAACCTTTTCGA-5'

Sense HSR sequence:     GGACTGGTGTGAGGACTAC (SEQ ID NO: 21)
Antisense HSR sequence: GTAGTCCTCACACCAGTCC (SEQ ID NO: 25)

Stem-loop sequence: GGACTGGTGTGAGGACTACTTCAAGAGAGTAGTCCTCACACCAGTCC (SEQ ID NO: 30)
```

Both siHSR1-160 and siHSR1-224 were assembled by annealing to corresponding single-stranded oligos. The resulting double-stranded oligo with BglII-compatible/HindIII overhangs was ligated into BglII/HindIII digested pSuper vector (OligoEngine, Inc., Seattle, Wash.). Upon transcription these fragments form hairpin structure with 19 nt double-stranded stem and 9 nt bubble (TTCAAGAGA (SEQ ID NO: 26)). This hairpin is cleaved in the bubble in the cells to produce dsRNA with UU overhangs on both ends.

The effect of siRNA was monitored by the HS induced expression of a plasmid-derived *Renilla* luciferase (RLuc) reporter fused to the inducible human hsp70 promoter (see Methods). This construct was co-transfected with siRNA vectors into HeLa cells and the induction of RLuc activity by HS was measured. As shown in FIG. 6C, while the RLuc activity was induced about 200-fold by HS treatment followed by recovery at 37° C., siRNA corresponding to the $6^{HSR1}$ antisense oligo (siHSR1-224; SEQ ID NO: 20 and SEQ ID NO: 28) strongly inhibited the HS induction of RLuc. Importantly, a mutant construct carrying a single G→C substitution in the siRNA sequence (mut224: G4→C; SEQ ID NO: 21 and SEQ ID NO: 30) had a significantly diminished effect on RLuc induction by HS.

Finally, HeLa cell lines stably expressing siHSR1 were generated. These cell lines were transiently transfected with the RLuc reporter plasmid and the HS induction of RLuc activity was monitored. In agreement with previous data, cells expressing siHSR1 or HSR1 antisense (aHSR1, SEQ ID NO: 3) but not GFP were deficient in their ability to induce RLuc activity after 2 h HS at 43° C. followed by overnight recovery at 37° C. (FIG. 6D). Moreover, the induction of HSF1 DNA binding activity by HS was severely impaired in siHSR1, but not in GFP expressing cells (FIG. 6D, inset). Predictably, cells stably expressing siHSR1 failed to acquire thermotolerance after HS pre-conditioning (FIG. 6E). Taking together, these data show that HSR1 is essential for the HS response in mammalian cells.

DISCUSSION

Recent studies have implicated various untranslated RNAs in a surprisingly wide spectrum of regulatory functions (Nudler and Mironov, Trends Biochem. Sci. 2004; 29:11-17 and Szymanski and Barciszewski, Int. Rev. Cytol. 2003; 231: 197-258). The present invention encompasses a novel presumably untranslated RNA that is involved in activation of the HS response. HSR1 likely serves as a cellular thermosensor that assumes an HSF-1 activating conformation in response to elevated temperature. The ability of HSR1 to dramatically change its mobility apparently due to oligomerization (FIG. 5C) is consistent with this notion. As the master activator of HSP genes, HSF1, requires two components in order to acquire its DNA binding activity—eEF1A and thermosensor RNA (HSR1). HSR1 and/or eEF1A may participate in HSF1 interaction with other components of transcription machinery. This model provides a framework for designing new potential therapeutics to control heat shock response in vivo for cancer treatment and other pharmacological applications.

Example 5

Comparative Analysis of the HSR1 from BHK, HeLa, and *Drosophila* Kc Cells

HSR1 from *Drosophila* Kc cells are sequenced and cloned in order to compare the degree of evolutionary conservation of HSR1 between different species (see also data in Example 1 indicating that HSR1-like RNA exists in *Drosophila* Kc cells). Once the full sequence of HSR1 is available, the extensive search of sequence databases is performed to identify the HSR1 coding gene.

cDNAs of each full-length HSR1 are obtained and cloned into pBluescript vector harboring T7 and T3 RNA polymerase promoters that face each other. Transcription with T7 and T3 RNA polymerases produce both sense and antisense copies of HSR1 in large quantities in vitro. Similarly to experiments with cloned hamster and human HSR1 disclosed in Examples 3 and 4, HSF activation in reconstituted system in vitro is assayed using HSR1 from different species. In these assays, purified recombinant human or mouse HSF1 or Drosophila HSF (with and without $His_6$-tag) are used.

To further assess the extent of the functional conservation of key components of the HSF activating complex, pure HSR1 and eEF1A isolated from human, mouse, and Drosophila cells are used to cross-activate HSFs from different species. Specifically, it is determined if Drosophila HSR1 (KcHSR1) is able to activate mouse and human HSF and vice versa.

Additional screening for functionally important domains in HSR1 is performed using deletion and mutational analysis. In parallel, using a series of deletions in the HSR1, the minimal portion of HSR1 that still supports activation of HSF1 in vitro is identified.

To further delineate the most conserved and functionally important domains of HSR1, in addition to direct sequence comparison of KcHSR1, HeLaHSR1 and BHKHSR1, a comparative analysis of their secondary/tertiary structures is performed using RNA nuclease mapping and RNA self-cleavage approach (see Example 7, infra). The cleavage patterns from RNase and "self cleavage" experiments are compared between KcHSR1, HeLaHSR1 and BHKHSR1 and computationally analyzed to find the common structural domains.

Example 6

Evaluation of HSR1 as a Thermosensor

As mentioned above, it is hypothesized that HSR1 serves as a thermosensor that undergoes a conformational change in the cell in response to elevated temperature. Such a change induces HSF trimerization and DNA binding. Since eEF1A is extremely conserved in all eukaryotic species from yeast to human, it appears likely that HSR1 from different species (e.g., Drosophila and human) are set for different temperature thresholds thus determining the heat shock response condition for each organism. RNA thermosensors have been described in bacteria, although their mode of action must be principally different from that of HSR1 (Storz, Genes Dev. 1999; 13:633-636).

To determine whether HSR1s sense heat, the structures of in vitro transcribed KcHSR1, HeLaHSR1 and BHKHSR1 are probed using enzymatic and spontaneous cleavage approaches to test whether RNA undergoes conformational changes upon exposure to a certain elevated temperature. Nuclease mapping strategy utilizes several sequence- and structure-specific nuclease enzymes: mung beans nuclease (cleaves single stranded RNA (ssRNA)), RNase A (pyrimidine-specific nuclease, cleaves ssRNA), RNase T1 (cleaves ssRNA 3' to G), V1 (cleaves double stranded (dsRNA)). Terminally [$^{32}$P] labeled HSR1 is treated by nucleases under single hit conditions before and after incubation for 30 min at 43° C. (for HeLaHSR1) or 32° C. (for KcHSR1) and analyzed by denaturing PAGE. The change in cleavage pattern indicates change in the secondary structure of HSR1 associated with elevated temperature.

Additional structural information is obtained using RNA spontaneous 'self-cleavage' approach (Soukup, et al., RNA. 1999a; 5:1308-1325). This structure-probing process relies on the inherent chemical instability of RNA under physiological conditions that occurs primarily due to the spontaneous cleavage of phosphodiester linkages via intramolecular transesterification reactions. The internucleotide linkages in unstructured regions are more likely to undergo spontaneous cleavage compared to linkages that reside in highly structured regions of RNA (Soukup, et al., RNA. 1999b; 5:1308-1325). Single-hit conditions for BHKHSR1 are 12 h at 37° C.

Example 7

Investigation of Protein-RNA Contacts in HSF1/HSR1/eEF1A Ternary Complex Before and after Heat Shock As the right in vivo conformation of HSR1 may be assumed only in complex with proteins, the results obtained in RNase mapping and self-cleavage experiments in Example 7 are used as a starting point for a detailed investigation of the structure of HSF1/HSR1/eEF1A ternary complex and the temperature-inducible conformational changes in HSR1. To address this question, the regions of HSF1 and eEF1A are mapped relative to HSR1 RNA by chemical derivatization of HSF and eEF1A in the ternary complex using a variety of highly specific and inducible cross-linkable reagents incorporated into defined positions in HSR1. The cross-linking is followed by mapping adducts using chemical and enzymatic degradation of derivatized proteins. The following cross-linkable NTP substrates are used: a) 4-thio-UTP, 6-thio-GTP, and 2-Iodo-UTP as short arm (<1 Å) photoactivable cross-linkers (these reagents are commercially available as monophosphates, e.g., from TriLink Biotechnologies, San Diego, Calif.) and were converted to the triphosphate form as disclosed in Gusarov and Nudler, Cell 2001; 107:437-49); b) aryl azido derivative of the 5-aminoallyl UTP as a medium arm (~7 Å) photoactivable cross-linker, and bis(2-iodoethyl) amino derivative of aminoallyl UTP as a long arm (~12 Å) chemically activable cross-linker (synthesized and used as disclosed in Nudler, et al., Science 1998; 281:424-428).

In each experiment the cross-linkable reagent is incorporated into a single defined position in HSR1 using walking technology developed by the inventors and co-workers, i.e., step-wise transcription in solid phase as disclosed in Nudler, et al., Science 1998c; 281:424-428; Gusarov, et al., Mol. Cell 1999; 3:495-504; Nudler, et al., Science 1994; 265:793-796. This method allows introduction of a radioactive label or cross-linking derivative of nucleotides into any desired position along the RNA sequence. The principle behind the solid-phase walking is that the initial elongation complex immobilized onto a solid support undergoes rounds of washing (to remove the unincorporated NTP substrates) followed by addition of the incomplete set of NTPs (three or less) that allows transcription to proceed to the next DNA position corresponding to the first missing NTP (FIGS. 7A-B). Briefly, full size HSR1 is cloned so that its sequence starts after position +11 of T7A1 promoter. $His_6$-tagged E. coli RNA polymerase is immobilized on $Ni^{++}$ or $Co^{++}$ chelating beads and the transcription is initiated by addition of T7A1 promoter DNA fused to HSR1 sequence. After initiation of transcription with CpApUpC RNA primer, ATP and GTP, the beads containing initial elongation complex are washed with transcription buffer to remove unincorporated NTPs. In the next step(s), the appropriate limited mixture of NTPs is added to move RNA polymerase to the next desired position (FIG. 7A). At a certain step, the cross-linkable NTP analog and/or radiolabeled NTP is added so that a single modification is introduced exactly at the desired position followed by chase reaction to complete the RNA synthesis.

Modified or labeled nucleotides can be introduced at any step during the walking procedure (Nudler et al., Methods Enzymol. 2003; 371:160-9), enabling synthesis of the HSR1 transcript that carries a cross-linkable analog or radioactive label virtually at any desired position. However, the walking procedure is mostly useful for obtaining RNA modifications close to the promoter because of inevitable loss of the material during multiple washing steps. To introduce radioactive label or modified base deep inside the long RNA sequence, a "roadblock" modification of the procedure is used (FIG. 7B). The latter relies on the mutant form of EcoRI restriction endonuclease, EcoRQ111 (provided by Dr. Paul Modrich, Duke University; Wright et al., 1989, J. Biol. Chem., 264: 11816-11821), which binds EcoRI site but does not cut the DNA. RNA polymerase stops upon encountering DNA bound EcoRQ111. After washing out unincorporated NTPs, the "roadblock" is removed by high salt wash, which leaves elongation complex intact (Nudler et al., Cell 1995; 81:351-7; Nudler et al., Methods Enzymol. 2003; 371:160-9). From this point, elongation complex is walked to the desired position as described above. Therefore, introducing EcoRI site near the target position in HSR1 sequence by PCR mutagenesis allows incorporating NTP derivatives (e.g., 4-thiouridine or 6-thioguanosine) at any distal position along the HSR1 sequence.

The HSR1 derivatives synthesized in vitro using "walking" technique are then incubated with HSF and/or eEF1A and the cross-linking is initiated by brief UV irradiation. Following cross-linking, the labeled protein is digested under the single-hit conditions with cyanogen bromide (CNBr) [cleaves after methionine (M)]. The RNA is digested with ribonuclease and the reaction mixture is then resolved on SDS-PAGE. This procedure results in the transfer of radioactive label, which was incorporated adjacent to the cross-linking derivative, to the protein. Therefore, cross-linking sites on proteins are mapped using limited single-hit protein degradation with different reagents. The following chemical and enzymatic degradation agents are used:

| Agent | Cleaves at |
|---|---|
| cyanogene bromide (CNBr) | Methionine |
| 2-nitro-5-thiocyanobenzoic acid (NTCBA) | Cysteine |
| chloro-succinimide | Tryptophan |
| endoproteinase Lys-C | Lysine |
| endoproteinase Glu-C | Glutamic acid |

Using a combination of these cleaving agents, it is possible to map crosslinking sites within 10-20 amino acids (Nudler, et al., Science 1998b; 281:424-428). Human and mouse HSF1 contain 12 Met and 5 and 4 Cys residues, respectively, which makes them well suited for the limited degradation analysis. Drosophila HSF contains 26 Met and only 1 Cys residue but also has 3 Trp residues. Finally, eEF1A sequence includes 12 Met and 6 Cys residues. Thus, the limited CNBr and NTCBA degradation yields characteristic peptide patterns for each protein and allows high-resolution mapping of cross-linking sites within HSF and eEF1A molecules.

In addition to crosslinking, chemical footprinting of both RNA and proteins is used to analyze the HSF/eEF1A/HSR1 ternary complex. The dynamic change of protection areas on RNA and proteins provides independent information on direct contacts between components of the ternary complex before and after heat shock. Various HSR1s (either in vitro synthesized or purified from cell extracts) are 5' [$^{32}$P] labeled with T4 polynucleotide kinase. HSR1 footprinting with and without HSF/eEF1A is performed using FeEDTA-generated hydroxyl radicals that attack the sugar moiety. OH• are particularly useful probes in this case since, in contrast to base-modifying probes such as dimethyl sulfate, or nucleases, they do not discriminate between single- and double-stranded sites on the RNA (Celander, et al., Biochemistry 1990; 29:1355-1361). Fe(II)-EDTA-hydrogen peroxide solutions have been previously used by the inventors and co-workers to probe protein-RNA interactions in transcription complexes (Nudler, et al., Cell 1997; 89:33-41).

Hydroxyl radical footprinting is also used in relation to HSF1, to determine which protein regions of HSF1 are in direct contact with other components of the ternary complex. Specifically, an adaptation of the hydroxyl radical footprinting method of Heyduk and co-workers (Heyduk, et al., Biochemistry 1994; 33:9643-9650; Heyduk, et al., Proc. Natl. Acad. Sci. U.S.A. 1996; 93:10162-10166) is used as follows: 1) HSF1 is $^{33}$P-end labeled using an introduced recognition site for heart-muscle protein kinase (HMPK); 2) in parallel reactions, HO•-mediated cleavage of labeled HSF1 itself and in the complex with eEF1A and/or HSR1 is performed under single-hit conditions; 3) the cleavage products are analyzed by denaturing PAGE and PhosphorImager. Binding of the ligand (HSR1 and eEF1A) decreases polypeptide backbone solvent accessibility at residues it contacts, protecting against HO• cleavage, therefore, resulting in a gap in the ladder of cleavage products. The location of the ligand-binding site is read out directly from location of the gap in the ladder.

The results obtained using the methods described above provide comprehensive information regarding the dynamic structural organization of the HSR1/eEF1A/HSR1 ternary complex under stress and non-stress conditions. This information is useful for understanding the basic principals of HSF1 activation and also for designing the most effective small antisense HSR1 oligonucleotides for in vivo inhibition of HSPs expression (see Example 15, infra).

Example 8

Investigation of the Role of HSR1/eEF1A in Heat-Inducible HSF1 Phosphorylation

As mentioned in the Background Section, the second step in the pathway leading to transcription activation by HSF1 is its hyperphosphorylation (Christians et al., Crit. Care Med. 2002; 30(1 Supp):S43-S50). Since hyperphosphorylation-dependant transcription activity of HSF1 trimers depends on heat shock stimuli but not other stresses, e.g. salicylate treatment (Jurivich, et al., J. Biol. Chem. 1995b; 270:24489-24495), it is hypothesized that HSR1/eEF1A not only induces HSF1 trimerization and DNA-binding but also regulates HSF1 phosphorylation upon heat shock. It was shown in previous studies that phosphorylation of Ser230 residue by calcium/calmodulin dependent protein kinase II (CaMKII) as well as Ser363 by c-Jun N-terminal kinase (JNK) activate transactivation function of HSF1 (Holmberg, et al., EMBO J. 2001; 20:3800-3810). In the present Example, the inventors set out to test whether HSR1/eEF1A promotes HSF1 phosphorylation at Ser230, 263 upon heat shock by performing in vitro HSF activation experiments in the presence of CaMKII (Promega) or JNK (Upstate Biotechnologies, Lake Placid, N.Y.) and radioactive ATP. HSF phosphorylation is performed in the presence or absence of eEF1A and HSR1, at heat shock (43° C.) or normal (37° C.) temperature. The reaction is terminated and resolved on SDS-PAGE. Gels are exposed to X-ray film to determine the extent of HSF1 phosphorylation. HSF1 phosphorylation sites are mapped more precisely using methodology described in Example 8, supra.

Example 9

Investigation of Subcellular Localization of HSR1, eEF1A, and HSF Before and after Heat Shock The subcellular distribution of the HSF1 activating components before and after heat shock is analyzed using conventional biochemical methods such as separation of nuclear extracts from that of cytoplasm and immunofluorescent staining of fixed cells followed by observing with confocal microscopy.

To test whether cytoplasm or nuclear extract of unstressed cells can be activated in vitro by eEF1A and HSR1, cytoplasm and nuclear extracts are prepared as disclosed in Manalo, et al., Biochemistry 2002; 41:2580-2588 and Manalo, et al., J. Biol. Chem. 2001; 276:23554-23561. Aliquots are incubated with eEF1A and in vitro transcribed HSR1 and subjected to EMSA analysis.

The distribution of eEF1A between cytoplasm and nucleus during heat shock is analyzed in BHK and HeLa cells by immunostaining and immunoprecipitation using monoclonal anti-eEF1A antibodies (Upstate Biotechnologies, Inc., Lake Placid, N.Y.). Cells are cultured on coverslips (for immunstaining) or in flasks and subjected to heat shock. Then the cells are either fixed and stained with anti-eEF1A antibodies or cytoplasmic and nuclear extracts are prepared from the cells and eEF1A is immunoprecipitated. Two different methods of protein fixation are used: paraformaldehyde (protein-protein and protein-nucleic acid cross-linking) and methanol (protein precipitation). Optimization of the staining conditions is performed including duration of cell fixation, composition of the solutions used to permeabilize membranes and block the non-specific protein binding. A preliminary data obtained by the inventors indicate that there is heat shock dependent nuclear localization of a sub-population of eEF1A molecules. Curiously, eEF1A was shown at least in one case to display nuclear localization in response to specific stimuli (Gangwani, et al., J Cell Biol 1998a; 143:1471-1484).

To follow HSR1 subcellular localization in response to heat shock, the HSR1 antisense oligonucleotides that did not interfere with HSF activation in reconstituted system are coupled with fluorescent dye and transfected into BHK and HeLa cells. The cells then are either heat shocked or kept at normal growth temperature and observed using fluorescent microscope.

Example 10

Investigation of HSF1/eEF1A/HSR1 Complex Formation with DNA In Vivo by Chromatin Immunoprecipitation (chIP)

It is useful to understand what happens with the HSF1/eEF1A/HSR1 complex after HSF activation and binding to DNA (HSE site) in vivo. To determine whether eEF1A and/or HSR1 stay with HSF1 on the promoter and for how long, chromatin immunoprecipitation (chIP) assay is used. The assay combines reversible in vivo formaldehyde cross-linking with immunoprecipitation and PCR. Protein-protein and protein-DNA cross-linking is induced in vivo on the heat shock inducible human HSP70 promoter of the plasmid that is transiently transfected into HeLa cells. The cross-linked material is immunoprecipitated with antibodies to eEF1A or HSF1. In a control experiment, eEF1A IP and HSF-1 IP from unstressed cells is performed. After reversing cross-linking and digestion of proteins with proteinase K, the cross-linked DNA is isolated and the fragment of interest is amplified by quantitative real-time PCR. Next, the amount of PCR product from eEF1A IP is compared to that of HSF1. The latter is taken as 100% since under heat shock conditions most, if not all, heat shock promoters should be occupied by HSF1 trimers (Shopland, et al., Chromosoma 1996; 105:158-171). Real-time PCR allows comparison of multiple reactions in their respective linear range, even if these reactions follow very different kinetics. This can not be achieved by a common PCR and quantifying their products on agarose gel, as conventionally performed in chIP. The above procedure is used to quantify the amount of HSR1 present in the precipitated cross-linked complexes. In this case, single tube real-time RT-PCR is used. The quantity of each of the components mentioned above is measured in unstressed cells, cells heat shocked (43° C.) for various periods of time and cells that were heat shocked and allowed to recover at 37° C. in order to follow the kinetics of protein-protein and protein-RNA interactions during HSF1 activation.

Example 11

Investigation of the Mechanism of HSF Activation in Lower Eukaryotes (Drosophila and Yeast) and Other Members of HSF Family (HSF2, HSF4)

The power of genetic manipulation with Drosophila and yeast make these species particular attractive in addressing fine molecular and physiological details of the HSF activation process.

In Drosophila melanogaster, components of HSF activation system are identified on polytene chromosomes. Polytene chromosomes have been used extensively for direct visualization of various transcription and chromatin components (Simon, et al., Cell 1985; 40:805-817; Lis, et al., Genes Dev. 2000; 14:792-803; Andrulis, et al., Genes Dev. 2000; 14:2635-2649). Briefly, following heat shock, salivary gland is dissected, mounted on slide, and fixed by formaldehyde. The fixed slides are then stained by incubation with commercial antibodies against HSF and eEF1A followed by several washes and incubation with appropriate secondary fluorescent dye-conjugated (FITC and/or TRITC, Jackson Immunoresearch Laboratories, Inc.) antibody. Antibody is diluted in a solution containing 5% normal donkey serum to minimize non-specific background. Fluorescent microspheres are added to the samples stained by two antibodies to align color merges. DNA is visualized by staining with Hoechst 33258 (Invitrogen, CA). Images are collected using either fluorescent or confocal microscope.

Currently, the general consensus holds that HSF in yeast is constitutively trimeric and bound to HSE of heat shock promoters. Heat shock treatment is believed to induce transactivation function of HSF but little or no additional DNA binding (Jakobsen, et al., Mol. Cell Biol. 1988; 8:5040-5042 Jakobsen, et al., Mol. Cell Biol. 1988; 8:5040-5042; Sorger, et al., Nature 1987; 329:81-84). Yeast HSF also differs from higher eukaryotic HSF1 in lacking the fourth leucine zipper domain on its C-terminus. This domain has been implicated in inducible HSF trimerization and acquisition of DNA binding activity (Bonner, et al., Mol. Biol. Cell 2000a; 11:1739-1751; Bonner, et al., J. Mol. Biol. 2000b; 302:581-592). However, other data suggest that even in yeast exposure to elevated temperature can result in 10 to 20 fold increase in HSF binding to DNA (J. Lis, personal communication).

In the present Example, the methodology developed in mammalian and Drosophila systems is applied to address the mechanism of activation of HSF in yeast. First, the existence of RNA similar to HSR1 in yeast cells is verified. This is done by coupling HSF from *Saccharomyces cerevisiae* cells to activated Sepharose and incubating the resulting beads with the lysate of heat shocked cells followed by RNA extraction and sequencing (see Examples 1-3).

HSF2 is another member of HSF protein family (Mathew, et al., Mol. Cell Biol. 2001; 21:7163-7171). Unlike HSF1, which is activated in response to stress, HSF2 is activated during specific stages of development (Eriksson, et al., Int. J. Dev. Biol. 2000; 44:471-477; Min et al., Biochim. Biophys. Acta. 2000; 1494:256-62; Loones, et al., Cell Mol. Life. Sci. 1997; 53:179-190), in hemin-induced cell differentiation (Sistonen, et al., Mol. Cell Biol. 1992; 12:4104-4111), and in response to inhibition of the ubiquitin-dependent proteosome (Mathew, et al., Mol. Cell Biol. 1998; 18:5091-5098). HSF2 is an unstable protein which exists in the cell in inactive monomeric and dimeric form but converts to trimers upon activation (Wu, Ann. Rev. Cell Dev. Biol. 1995; 11:441-469).

The most recently discovered member of HSF family, HSF4, is expressed in tissue specific manner in two splice isoforms —HSF4a and HSF4b (Nakai, Chaperones. 1999; 4:86-93). The former lacks transactivation domain present in all HSF proteins and acts as a repressor of HSF1 mediated transcription (Zhang, et al., J. Cell Biochem. 2001; 82:692-703).

To determine whether HSF2 and HSF4 are also activated by an RNA-dependent mechanism similar to HSF1, these members of HSF family are expressed in bacteria as either His6-tagged or GST-fusion proteins, purified and covalently immobilized on Sepharose. The resulting HSF2-and HSF4-Sepharose is used to trap HSF2/HSF4-interacting proteins and RNA from the lysate of heat shocked or unstressed cells.

In summary, the experiments described in this section determine the intracellular compartment where the activation of HSF takes place and the role of HSR1/eEF1A in HSF phosphorylation and transcription activation. In addition, they allow to further characterize the mechanism of interaction between HSR1 and HSF/eEF1A and possibly other associated factors in vivo and check the possibility that other HSF family members such as HSF2 and HSF4 require RNA for their activation. Finally, studies in *Drosophila* and yeast show the extent of evolutionary conservation of the proposed mechanism of activation of heat shock response.

Example 12

Isolation of Cellular Factors that are Associated with HSF1-HSR1-eEF1A Complex Before and after Heat Shock As mentioned in the Background Section, HSF1 is a target for many factors that are directly or indirectly involved in regulation of stress response. Proteins that have been shown to physically associate with HSF1 include several members of preinitiation transcription complex such as mediator and activators (Park, et al., Mol. Cell 2001; 8:9-19; Mason, et al, J. Biol. Chem. 1997; 272:33227-33), transcription elongation factor P-TEFb (Lis, et al., Genes Dev. 2000; 14:792-803), and SWI/SNF chromatin remodeling complex (Sullivan, et al., Mol. Cell Biol. 2001; 21:5826-5837). Recruitment and/or activation of these factors by HSE-bound HSF1 is thought to play a critical role in the mechanism of transcription activation of HSP genes. In addition, negative regulator of HSF1 (HSBP1) has been shown to bind HSF1 directly to modulate its activity (Satyal et al., Genes Dev. 1998; 12:1962-74). HSF1 binding proteins have been identified using either coimmunoprecipitation with antibodies against HSF1 or yeast two-hybrid screens with HSF1 domains as a bait.

To identify new HSF1-binding proteins and known proteins whose interaction with HSF1 is affected by the formation of the HSF1/HSR1/eEF1A ternary complex, in vivo crosslinking with formaldehyde (Hall, et al., J. Biol. Chem. 2002; 277:46043-46050) is combined with affinity chromatography using biotinylated HSR1-antisense oligonucleotides as a tag. Crosslinking (0.7% formaldehyde, 20 min, 37° C.) is performed in 10-20 flasks of cultured cells grown under stress (e.g., 1 h at 43° C.) and non-stress conditions. Proteins that are crosslinked to the HSF1/HSR1/eEF1A complex are precipitated on NeutrAvidin™ beads (Pierce; >17 μg/ml of slurry beads) under strict conditions to remove non-specifically bound proteins (e.g., 2M KCl, mild detergents) using 3'-biotinylated and 5'-biotinylated HSR1 antisense oligonucleotides. Several such oligonucleotides (e.g., $1^{HSR1}$, $6^{HSR1}$, $14^{HSR1}$, see FIG. 5E) complementary to different parts of HSR1 are used. A biotinylated oligonucleotide which is not complementary to HSR1 is used as a negative control. After precipitation on beads and thorough washing, the crosslinking is reversed by boiling for 20 min. Precipitated proteins are resolved on SDS PAGE and silver-stained. MALDI-TOF analysis is used to identify the isolated proteins (Bar-Nahum, et al., Cell 2001; 106:443-451). Candidate proteins are cloned and analyzed for their effect on HSF1 activation in vitro and HSP expression in vivo (see Examples, supra).

Example 13

Design of Novel Anti-Cancer Drugs Based on HSR1 Antisense Oligonucleotides

HSPs (in particular HSP70) play a critical role in protecting the cell against apoptosis (see Background Section). As disclosed herein, the present inventors have identified a novel RNA, HSR1, that is involved in the process of HSF1 activation in response to heat shock. As further disclosed herein, the present inventors have demonstrated that HSR1 antisense oligonucleotides are capable of inhibiting HSF1 activation in vivo when transfected in BHK and HeLa cells and render them heat sensitive. This opens up an intriguing possibility of developing a novel anti-cancer agents based on HSR1 antisense oligonucleotides, which can be used in conjunction with existing treatments to improve their effect by increasing the sensitivity of the cells to pro-apoptotic stimuli such as thermo-, chemo-, and radiotherapeutic treatments.

Study of the Effect of HSR1 Antisense Oligonucleotides Transfection on Cell Survival after Heat Shock As disclosed in Example 4, supra, the present inventors have synthesized a series of 45-mer oligonucleotides covering the entire HSR1 sequence and screened them for the ability to suppress HSF1 activation in vitro. Four of these oligonucleotides effectively suppressed HSF1 activation in the reconstituted system (FIG. 5E). Transfection of the most effective antisense oligonucleotide ($6^{HSR1}$; SEQ ID NO: 12) into BHK and HeLa cells had a strong inhibitory effect on HSF1 activation by heat shock in vivo and rendered cells sensitive to heat (FIG. 6A). The data show that this treatment dramatically reduces the level of HSP expression and, therefore, promotes pro-apoptotic processes that are otherwise blocked by increased HSP expression.

To explore the possibility of using HSR1 antisense oligonucleotides to treat cancer, a model thermotolerant breast cancer cell line (Bcap37, maintained by the Cancer Institute of Zhejiang University; Wang, et al., Biochem. Biophys. Res.

Commun. 2002; 290:1454-1461) is transfected with $6^{HSR1}$ oligonucleotide and the survival of cells is evaluated after heat shock treatment (1 h at 43° C.) in comparison to that of untransfected cells. Cell survival plot is generated using flow cytometry analysis as well as Cell Titer Glo luminescent cell viability assay (Promega). The latter provides a method for determining the number of viable cells in culture based on quantitation of ATP.

To confirm that HSR1 antisense oligonucleotide treatment indeed leads to reduction in HSP70 level in Bcap37 cells, lysates of heat shocked transfected cells are analyzed by immunoblotting.

HSR1 antisense oligonucleotides which show the strongest effect on cell survival and HSP expression may be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in inhibition of cell survival and inhibition of HSP expression.

Study of the Effect of HSR1 Antisense Oligonucleotides on Tumor Progression in Nude Mice The HSR1 antisense oligonucleotides selected as the most potent in cell culture assays in the previous section are used to develop a product, which, when delivered directly to the tumor, reduces expression of HSPs in cancer cells thereby making them more susceptible to apoptotic stimuli and cytotoxic agents. Specifically, nude mice (BALB/c nu/nu strain [Taconic]) are inoculated by subcutaneous and bilateral injection with thermotolerant breast cancer Bcap37 cells to induce tumor formation. When the tumors reach 3-4 mm in diameter, the mice are administered phosphothioate-modified anti-HSR1 oligonucleotides by injection into tumors, allowed 16-24 h for the oligonucleotide uptake, and heat shocked for 30 min at 43° C. in an incubator. As previously mentioned, phosphothioate or morpholino modification of the oligonucleotides is required to minimize their susceptibility to exonucleases and ensure adequate stability in the tissue. In addition to heat-shock, a separate group of experimental mice with anti-HSR1 oligonucleotide pretreated Bcap37 tumors are treated with a standard anti-cancer drug (e.g., fluorouridine). In all cases, the treatment is continued for one week and the tumor size is assessed by measuring its dimensions and calculating volume. Three control groups of animals receive heat shock treatment without antisense oligonucleotides, with oligonucleotides of the same length but randomized sequence, and no treatment at all. Similar methodology have been used recently to show that blocking of HSF1 by dominant-negative mutant leads to enhanced efficiency of heat shock treatment of tumor induced in nude mice by injection of Bcap37 cells (Wang, et al., Biochem. Biophys. Res. Commun. 2002; 290:1454-1461).

In parallel, tumor tissues from treated and control animals are excised, homogenized and assayed for the activation of HSF1 by EMSA. The level of HSP72 production is determined as well using standard immunoblotting techniques.

REFERENCES CITED

1. Andrulis, E. D., Guzman, E., Doring, P., Wemer, J., and Lis, J. T. (2000). High-resolution localization of *Drosophila* Spt5 and Spt6 at heat shock genes in vivo: roles in promoter proximal pausing and transcription elongation. Genes Dev. 14, 2635-2649.
2. Bar-Nahum, G. and Nudler, E. (2001). Isolation and characterization of sigma(70)-retaining transcription elongation complexes from *Escherichia coli*. Cell 106, 443-451.
3. Blackwell, J. L. and Brinton, M. A. (1997). Translation elongation factor-1 alpha interacts with the 3' stem-loop region of West Nile virus genomic RNA. J. Virol. 71, 6433-6444.
4. Bold, R. J., Termuhlen, P. M., and McConkey, D. J. (1997). Apoptosis, cancer and cancer therapy. Surgical Oncology-Oxford 6, 133-142.
5. Bonner, J. J., Carlson, T., Fackenthal, D. L., Paddock, D., Storey, K., and Lea, K. (2000a). Complex regulation of the yeast heat shock transcription factor. Mol. Biol. Cell 11, 1739-1751.
6. Bonner, J. J., Chen, D., Storey, K., Tushan, M., and Lea, K. (2000b). Structural analysis of yeast HSF by site-specific crosslinking. J. Mol. Biol. 302, 581-592.
7. Cardoso, F., Di Leo, A., Larsimont, D., Gancberg, D., Rouas, G., Dolci, S., Ferreira, F., Paesmans, M., and Piccart, M. (2001). Evaluation of HER2, p53, bcl-2, topoisomerase II-alpha, heat shock proteins 27 and 70 in primary breast cancer and metastatic ipsilateral axillary lymph nodes. Ann. Oncol. 12, 615-620.
8. Celander, D. W. and Cech, T. R. (1990). Iron(II)-ethylenediaminetetraacetic acid catalyzed cleavage of RNA and DNA oligonucleotides: similar reactivity toward single- and double-stranded forms. Biochemistry 29, 1355-1361.
9. Ciocca, D. R., Fuqua, S. A., Lock-Lim, S., Toft, D. O., Welch, W. J., and McGuire, W. L. (1992). Response of human breast cancer cells to heat shock and chemotherapeutic drugs. Cancer Res. 52, 3648-3654.
10. Clos, J., Rabindran, S., Wisniewski, J., and Wu, C. (1993). Induction temperature of human heat shock factor is reprogrammed in a *Drosophila* cell environment. Nature 364, 252-255.
11. Condeelis, J. (1995). Elongation factor 1 alpha, translation and the cytoskeleton. Trends Biochem. Sci. 20, 169-170.
12. Conroy, S. E., Sasieni, P. D., Fentiman, I., and Latchman, D. S. (1998). Autoantibodies to the 90 kDa heat shock protein and poor survival in breast cancer patients. Eur. J. Cancer 34, 942-943.
13. Cotto, J. J., Fox, S. G., and Morimoto, R. I. (1997a). HSF1 granules: a novel stress-induced nuclear compartment of human cells. Journal of Cell Science 110, 2925-2934.
14. Cotto, J. J., Fox, S. G., and Morimoto, R. I. (1997b). HSF1 granules: a novel stress-induced nuclear compartment of human cells. Journal of Cell Science 110, 2925-2934.
15. Donze, O. and Picard, D. (1999). HSP90 binds and regulates Gcn2, the ligand-inducible kinase of the alpha subunit of eukaryotic translation initiation factor 2 [corrected] [published erratum appears in Mol Cell Biol 2000 Mar.; 20(5):1897]. Mol. Cell Biol. 19, 8422-8432.
16. Elledge, R. M., Clark, G. M., Fuqua, S. A., Yu, Y. Y., and Allred, D. C. (1994). p53 protein accumulation detected by five different antibodies: relationship to prognosis and heat shock protein 70 in breast cancer. Cancer Res. 54, 3752-3757.
17. Eriksson, M., Jokinen, E., Sistonen, L., and Leppa, S. (2000). Heat shock factor 2 is activated during mouse heart development. Int. J. Dev. Biol. 44, 471-477.
18. Farkas, T., Kutskova, Y. A., and Zimarino, V. (1998a). Intramolecular repression of mouse heat shock factor 1. Molecular and Cellular Biology 18, 906-918.
19. Farkas, T., Kutskova, Y. A., and Zimarino, V. (1998b). Intramolecular repression of mouse heat shock factor 1. Molecular and Cellular Biology 18, 906-918.

20. Gangwani, L., Mikrut, M., Galcheva-Gargova, Z., and Davis, R. J. (1998b). Interaction of ZPR1 with translation elongation factor-1alpha in proliferating cells. J Cell Biol 143, 1471-1484.
21. Gangwani, L., Mikrut, M., Galcheva-Gargova, Z., and Davis, R. J. (1998a). Interaction of ZPR1 with translation elongation factor-1 alpha in proliferating cells. J Cell Biol 143, 1471-1484.
22. Gusarov, I. and Nudler, E. (1999). The mechanism of intrinsic transcription termination. Mol. Cell 3, 495-504.
23. Hall, D. B. and Struhl, K. (2002). The VP16 activation domain interacts with multiple transcriptional components as determined by protein-protein cross-linking in vivo. J. Biol. Chem. 277, 46043-46050.
24. Heyduk, E. and Heyduk, T. (1994). Mapping protein domains involved in macromolecular interactions: a novel protein footprinting approach. Biochemistry 33, 9643-9650.
25. Heyduk, T., Heyduk, E., Severinov, K., Tang, H., and Ebright, R. H. (1996). Determinants of RNA polymerase alpha subunit for interaction with beta, beta', and sigma subunits: hydroxyl-radical protein footprinting. Proc. Natl. Acad. Sci. U.S. A 93, 10162-10166.
26. Holmberg, C. I., Hietakangas, V., Mikhailov, A., Rantanen, J. O., Kallio, M., Meinander, A., Hellman, J., Morrice, N., MacKintosh, C., Morimoto, R. I., Eriksson, J. E., and Sistonen, L. (2001). Phosphorylation of serine 230 promotes inducible transcriptional activity of heat shock factor 1. EMBO J. 20, 3800-3810.
27. Hotokezaka, Y., Tobben, U., Hotokezaka, H., Van Leyen, K., Beatrix, B., Smith, D. H., Nakamura, T., and Wiedmann, M. (2002). Interaction of the eukaryotic elongation factor 1A with newly synthesized polypeptides. J. Biol. Chem. 277, 18545-18551.
28. Hsu, A-L, Murphy, C. T., Kenyon, C. (2003). Regulation of Aging and Age-Related Disease by DAF-16 and Heat-Shock Factor. Science. 300, 1142-1145)
29. Hubel, A., Lee, J. H., Wu, C., and Schoffl, F. (1995). Arabidopsis heat shock factor is constitutively active in Drosophila and human cells. Mol. Gen. Genet. 248, 136-141.
30. Jaattela, M. (1999). Escaping cell death: Survival proteins in cancer. Experimental Cell Research 248, 30-43.
31. Jaattela, M. and Wissing, D. (1993). Heat-shock proteins protect cells from monocyte cytotoxicity: possible mechanism of self-protection. J. Exp. Med. 177, 231-236.
32. Jaattela, M., Wissing, D., Bauer, P. A., and Li, G. C. (1992). Major heat shock protein hsp70 protects tumor cells from tumor necrosis factor cytotoxicity. EMBO J. 11, 3507-3512.
33. Jakobsen, B. K. and Pelham, H. R. (1988). Constitutive binding of yeast heat shock factor to DNA in vivo. Mol. Cell Biol. 8, 5040-5042.
34. Jensen, R. E. and Johnson, A. E. (1999). Protein translocation: is HSP70 pulling my chain? Curr. Biol. 9, R779-R782.
35. Jolly, C., Morimoto, R. I., Robert-Nicoud, M., and Vourc'h, C. (1997). HSF1 transcription factor concentrates in nuclear foci during heat shock: relationship with transcription sites. Journal of Cell Science 110, 2935-2941.
36. Jurivich, D. A., Pachetti, C., Qiu, L., and Welk, J. F. (1995a). Salicylate triggers heat shock factor differently than heat. J. Biol. Chem. 270, 24489-24495.
37. Jurivich, D. A., Pachetti, C., Qiu, L., and Welk, J. F. (1995b). Salicylate triggers heat shock factor differently than heat. J. Biol. Chem. 270, 24489-24495.
38. Karlseder, J., Wissing, D., Holzer, G., Orel, L., Sliutz, G., Auer, H., Jaattela, M., and Simon, M. M. (1996). HSP70 overexpression mediates the escape of a doxorubicin-induced G2 cell cycle arrest. Biochem. Biophys. Res. Commun. 220, 153-159.
39. Kiang, J. G., Gist, I. D., and Tsokos, G. C. (2000). Regulation of heat shock protein 72 kDa and 90 kDa in human breast cancer MDA-MB-231 cells. Mol. Cell Biochem. 204, 169-178.
40. Kim, S. J., Tsukiyama, T., Lewis, M. S., and Wu, C. (1994). Interaction of the DNA-binding domain of *Drosophila* heat shock factor with its cognate DNA site: a thermodynamic analysis using analytical ultracentrifugation. Protein Sci. 3, 1040-1051.
41. Kristensen, P., Lund, A., Clark, B. F., Cavallius, J., and Merrick, W. C. (1998). Purification and characterisation of a tissue specific elongation factor 1 alpha (EF-1 alpha 2) from rabbit muscle. Biochem Biophys Res Commun 245, 810-814.
42. Latchman, D. S. (2001). Heat shock Proteins and Cardiac Protection. Cardiovascular Research 51, 637-646).
43. Lis, J. T., Mason, P., Peng, J., Price, D. H., and Werner, J. (2000). P-TEFb kinase recruitment and function at heat shock loci. Genes Dev. 14, 792-803.
44. Liu, P. C. and Thiele, D. J. (1999). Modulation of human heat shock factor trimerization by the linker domain. J. Biol. Chem. 274, 17219-17225.
45. Loones, M. T., Rallu, M., Mezger, V., and Morange, M. (1997). HSP gene expression and HSF2 in mouse development. Cell Mol. Life. Sci. 53, 179-190.
46. Louvion, J. F., Abbas-Terki, T., and Picard, D. (1998). HSP90 is required for pheromone signaling in yeast. Mol. Biol. Cell 9, 3071-3083.
47. Luft, J. C. and Dix, D. J. (1999). HSP70 expression and function during embryogenesis. Cell Stress. Chaperones. 4, 162-170.
48. Malkin, D. (2001). The role of p53 in human cancer. J. Neurooncol. 51, 231-243.
49. Manalo, D. J., Lin, Z., and Liu, A. Y. (2002). Redox-dependent regulation of the conformation and function of human heat shock factor 1. Biochemistry 41, 2580-2588.
50. Manalo, D. J. and Liu, A. Y. (2001). Resolution, detection, and characterization of redox conformers of human HSF1. J. Biol. Chem. 276, 23554-23561.
51. Mason, P. B., Jr. and Lis, J. T. (1997). Cooperative and competitive protein interactions at the hsp70 promoter. J. Biol. Chem. 272, 33227-33233.
52. Mathew, A., Mathur, S. K., Jolly, C., Fox, S. G., Kim, S., and Morimoto, R. I. (2001). Stress-specific activation and repression of heat shock factors 1 and 2. Mol. Cell. Biol. 21, 7163-7171.
53. Mathew, A., Mathur, S. K., and Morimoto, R. I. (1998). Heat shock response and protein degradation: regulation of HSF2 by the ubiquitin-proteasome pathway. Mol. Cell Biol. 18, 5091-5098.
54. Mayer, M. P., Brehmer, D., Gassler, C. S., and Bukau, B. (2001). HSP70 chaperone machines. Adv. Protein Chem. 59, 1-44.
55. Mercier, P. A., Foksa, J., Ovsenek, N., and Westwood, J. T. (1997). *Xenopus* heat shock factor 1 is a nuclear protein before heat stress. J. Biol. Chem. 272, 14147-14151.
56. Min, J. N., Han, M. Y., Lee, S. S., Kim, K. J., and Park, Y. M. (2000). Regulation of rat heat shock factor 2 expression during the early organogenic phase of embryogenesis. Biochim. Biophys. Acta 1494, 256-262.
57. Morimoto, R. I. (1998). Regulation of the heat shock transcriptional response: cross talk between a family of heat shock factors, molecular chaperones, and negative regulators. Genes Dev. 12, 3788-3796.
58. Morimoto, R. I., Jurivich, D. A., Kroeger, P. E., Mathur, S. K., Murphy, S. P., Nakai, A., Sarge, K. D., Abravaya, K., and Sistonen, L. (1994). Regulation of Heat Shock Gene Transcription by a Family of Heat Shock Factors. In The Biology of Heat Shock Proteins and Molecular Chaperones, R. I. Morimoto, A. Tissieres, and C. Georgopoulos, eds. (New York: Cold Spring Harbor Press), pp. 417-455.
59. Munshi, R., Kandl, K. A., Carr-Schmid, A., Whitacre, J. L., Adams, A. E., and Kinzy, T. G. (2001). Overexpression of translation elongation factor 1A affects the organization and function of the actin cytoskeleton in yeast. Genetics 157, 1425-1436.
60. Murray, J. W., Edmonds, B. T., Liu, G., and Condeelis, J. (1996). Bundling of actin filaments by elongation factor 1 alpha inhibits polymerization at filament ends. J. Cell Biol. 135, 1309-1321.
61. Nakai, A. (1999). New aspects in the vertebrate heat shock factor system: Hsf3 and Hsf4. Cell Stress. Chaperones. 4, 86-93.
62. Nudler, E., Goldfarb, A., and Kashlev, M. (1994). Discontinuous mechanism of transcription elongation. Science 265, 793-796.
63. Nudler, E., Gusarov, I., Avetissova, E., Kozlov, M., and Goldfarb, A. (1998a). Spatial organization of transcription elongation complex in *Escherichia coli*. Science 281, 424-428.
64. Nudler, E., Gusarov, I., Avetissova, E., Kozlov, M., and Goldfarb, A. (1998b). Spatial organization of transcription elongation complex in *Escherichia coli*. Science 281, 424-428.
65. Nudler, E., Gusarov, I., Avetissova, E., Kozlov, M., and Goldfarb, A. (1998c). Spatial organization of transcription elongation complex in *Escherichia coli*. Science 281, 424-428.
66. Nudler, E., Mustaev, A., Lukhtanov, E., and Goldfarb, A. (1997). The RNA-DNA hybrid maintains the register of transcription by preventing backtracking of RNA polymerase. Cell 89, 33-41.
67. Nylandsted, J., Brand, K., and Jaattela, M. (2000). Heat shock protein 70 is required for the survival of cancer cells. Ann. N.Y. Acad. Sci. 926, 122-125.
68. Ohtsuka, K. and Hata, M. (2000). Molecular chaperone function of mammalian HSP70 and HSP40—a review. Int. J. Hyperthermia 16, 231-245.
69. Orosz, A., Wisniewski, J., and Wu, C. (1996). Regulation of *Drosophila* heat shock factor trimerization: global sequence requirements and independence of nuclear localization. Mol. Cell Biol. 16, 7018-7030.
70. Park, J. M., Werner, J., Kim, J. M., Lis, J. T., and Kim, Y. J. (2001). Mediator, not holoenzyme, is directly recruited to the heat shock promoter by HSF upon heat shock. Mol. Cell 8, 9-19.
71. Pearl, L. H. and Prodromou, C. (2000). Structure and in vivo function of HSP90. Curr. Opin. Struct. Biol. 10, 46-51.
72. Pearl, L. H. and Prodromou, C. (2001). Structure, function, and mechanism of the HSP90 molecular chaperone. Adv. Protein Chem. 59, 157-186.
73. Pilon, M. and Schekman, R. (1999). Protein translocation: how HSP70 pulls it off. Cell 97, 679-682.
74. Pratt, W. B. (1997). The role of the hsp90-based chaperone system in signal transduction by nuclear receptors and receptors signaling via MAP kinase. Annu. Rev. Pharmacol. Toxicol. 37, 297-326.
75. Ryan, M. T. and Pfanner, N. (2001). HSP70 proteins in protein translocation. Adv. Protein Chem. 59, 223-242.
76. Sarge, K. D., Murphy, S. P., and Morimoto, R. I. (1993a). Activation of heat shock gene transcription by heat shock factor 1 involves oligomerization, acquisition of DNA-binding activity, and nuclear localization and can occur in the absence of stress [published errata appear in Mol Cell Biol 1993 May; 13(5):3122-3 and 1993 Jun.; 13(6):3838-9]. Mol. Cell Biol. 13, 1392-1407.
77. Sarge, K. D., Murphy, S. P., and Morimoto, R. I. (1993b). Activation of heat shock gene transcription by heat shock factor 1 involves oligomerization, acquisition of DNA-binding activity, and nuclear localization and can occur in the absence of stress [published errata appear in Mol Cell Biol 1993 May; 13(5):3122-3 and 1993 June; 13(6):3838-9]. Mol. Cell Biol. 13, 1392-1407.
78. Shopland, L. S., Hirayoshi, K., Fernandes, M., and Lis, J. T. (1995). HSF access to heat shock elements in vivo depends critically on promoter architecture defined by GAGA factor, TFIID, and RNA polymerase II binding sites. Genes Dev. 9, 2756-2769.
79. Shopland, L. S, and Lis, J. T. (1996). HSF recruitment and loss at most *Drosophila* heat shock loci is coordinated and depends on proximal promoter sequences. Chromosoma 105, 158-171.
80. Shyy, T. T., Asch, B. B., and Asch, H. L. (1989). Concurrent collapse of keratin filaments, aggregation of organelles, and inhibition of protein synthesis during the heat shock response in mammary epithelial cells. J. Cell Biol. 108, 997-1008.
81. Simon, J. A., Sutton, C. A., Lobell, R. B., Glaser, R. L., and Lis, J. T. (1985). Determinants of heat shock-induced chromosome puffing. Cell 40, 805-817.
82. Simon, M. M., Reikerstorfer, A., Schwarz, A., Krone, C., Luger, T. A., Jaattela, M., and Schwarz, T. (1995). Heat shock protein 70 overexpression affects the response to ultraviolet light in murine fibroblasts. Evidence for increased cell viability and suppression of cytokine release. J. Clin. Invest 95, 926-933.
83. Sistonen, L., Sarge, K. D., Phillips, B., Abravaya, K., and Morimoto, R. I. (1992). Activation of heat shock factor 2 during hemin-induced differentiation of human erythroleukemia cells. Mol. Cell Biol. 12, 4104-4111.
84. Sorger, P. K., Lewis, M. J., and Pelham, H. R. (1987). Heat shock factor is regulated differently in yeast and HeLa cells. Nature 329, 81-84.
85. Soukup, G. A. and Breaker, R. R. (1999b). Relationship between internucleotide linkage geometry and the stability of RNA. RNA. 5, 1308-1325.
86. Soukup, G. A. and Breaker, R. R. (1999a). Relationship between internucleotide linkage geometry and the stability of RNA. RNA. 5, 1308-1325.
87. Storz, G. (1999). An RNA thermometer. Genes Dev. 13, 633-636.
88. Sugahara, K, Inouye, S, Izu, H, Katoh, Y, Katsuki, K, Takemoto, T, Shimogori, H, Yamashita, H, Nakai, A. (2003). Heat shock transcription factor HSF1 is required for survival of sensory hair cells against acoustic overexposure. Hear Res. 182, 88-96.
89. Sullivan, E. K., Weirich, C. S., Guyon, J. R., Sif, S., and Kingston, R. E. (2001). Transcriptional activation domains of human heat shock factor 1 recruit human SWI/SNF. Mol. Cell Biol. 21, 5826-5837.
90. Tang, D., Khaleque, M. A., Jones, E. L., Theriault, J. R., Li, C., Wong, W. H., Stevenson, M. A., Calderwood S. K. (2005). Expression of heat shock proteins and heat shock protein messenger ribonucleic acid in human prostate carcinoma in vitro and in tumors in vivo. Cell Stress Chaperones. 10, 46-58.
91. Van Montfort, R., Slingsby, C., and Vierling, E. (2001). Structure and function of the small heat shock protein/alpha-crystallin family of molecular chaperones. Adv. Protein Chem. 59, 105-156.
92. Walter, M. F., Petersen, N. S., and Biessmann, H. (1990). Heat shock causes the collapse of the intermediate filament cytoskeleton in Drosophila embryos. Dev. Genet. 11, 270-279.
93. Walker, G. A., Lithgow, G. (2003). Aging Cell. 2, 131
94. Wang, J. H., Yao, M. Z., Gu, J. F., Sun, L. Y., Shen, Y. F., and Liu, X. Y. (2002). Blocking HSF1 by dominant-negative mutant to sensitize tumor cells to hyperthermia. Biochem. Biophys. Res. Commun. 290, 1454-1461.
95. Welsh, M. J. and Gaestel, M. (1998). Small heat-shock protein family: function in health and disease. Ann. N.Y. Acad. Sci. 851, 28-35.
96. Westwood, J. T., Clos, J., and Wu, C. (1991). Stress-induced oligomerization and chromosomal relocalization of heat-shock factor. Nature 353, 822-827.
97. Westwood, J. T. and Wu, C. (1993). Activation of Drosophila heat shock factor: conformational change associated with a monomer-to-trimer transition. Mol. Cell Biol. 13, 3481-3486.
98. Wu, C. (1995). Heat shock transcription factors: structure and regulation. Ann. Rev. Cell Dev. Biol. 11, 441-469.
99. Wu, C., Clos, J., Giorgi, G., Haroun, R. I., Kim, S. J., Rabindran, S. K., Westwood, J. T., Wisniewski, J., and Yim, G. (1994). Structure and Regulation of Heat Shock Transcription Factor. In The Biology of Heat Shock Proteins and Molecular Chaperones, R. I. Morimoto, A. Tissieres, and C. Georgopoulos, eds. (New York: Cold Spring Harbor Press), pp. 395-416.
100. Young, J. C., Moarefi, I., and Hartl, F. U. (2001). HSP90: a specialized but essential protein-folding tool. J. Cell Biol. 154, 267-273.
101. Zeenko, V. V., Ryabova, L. A., Spirin, A. S., Rothnie, H. M., Hess, D., Browning, K. S., and Hohn, T. (2002). Eukaryotic elongation factor 1A interacts with the upstream pseudoknot domain in the 3' untranslated region of tobacco mosaic virus RNA. J. Virol. 76, 5678-5691.
102. Zhang, Y., Frejtag, W., Dai, R., and Mivechi, N. F. (2001). Heat shock factor-4 (HSF-4a) is a repressor of HSF-1 mediated transcription. J. Cell Biochem. 82, 692-703.
103. Zhu, D., Dix, D. J., and Eddy, E. M. (1997). HSP70-2 is required for CDC2 kinase activity in meiosis I of mouse spermatocytes [published erratum appears in Development 1997 Sept.; 134(17):3218]. Development 124, 3007-3014.
104. Zuo, J., Rungger, D., and Voellmy, R. (1995). Multiple layers of regulation of human heat shock transcription factor 1. Mol. Cell. Biol. 15, 4319-4330.
105. Zylicz, M. and Wawrzynow, A. (2001). Insights into the function of HSP70 chaperones. IUBMB. Life 51, 283-287.
106. Zhong, M., Orosz, A. & Wu, C. Direct sensing of heat and oxidation by Drosophila heat shock transcription factor. Mol. Cell 2, 101-108 (1998).
107. Verkman, A. S. Green fluorescent protein as a probe to study intracellular solute diffusion. Methods Enzymol. 302, 250-264 (1999).
108. Dayel, M. J., Hom, E. F. & Verkman, A. S. Diffusion of green fluorescent protein in the aqueous-phase lumen of endoplasmic reticulum. Biophys. J. 76, 2843-2851 (1999).
109. Jolly, C., Usson, Y. & Morimoto, R. I. Rapid and reversible relocalization of heat shock factor 1 within seconds to nuclear stress granules. Proc. Natl. Acad. Sci. U.S.A 96, 6769-6774 (1999).
110. Nguyen, V. T., Kiss, T., Michels, A. A. & Bensaude, O. 7SK small nuclear RNA binds to and inhibits the activity of CDK9/cyclin T complexes. Nature 414, 322-325 (2001).
111. Yang, Z., Zhu, Q., Luo, K. & Zhou, Q. The 7SK small nuclear RNA inhibits the CDK9/cyclin Ti kinase to control transcription. Nature 414, 317-322 (2001).
112. Chao, S. H. & Price, D. H. Flavopiridol inactivates P-TEFb and blocks most RNA polymerase II transcription in vivo. J. Biol. Chem. 276, 31793-31799 (2001).
113. Ni, Z., Schwartz, B. E., Werner, J., Suarez, J. R. & Lis, J. T. Coordination of transcription, RNA processing, and surveillance by P-TEFb kinase on heat shock genes. Mol. Cell 13, 55-65 (2004).
114. Yik, J. H. et al. Inhibition of P-TEFb (CDK9/Cyclin T) kinase and RNA polymerase II transcription by the coordinated actions of HEXIM1 and 7SK snRNA. Mol. Cell 12, 971-982 (2003).
115. Lanz, R. B. et al. A steroid receptor coactivator, SRA, functions as an RNA and is present in an SRC-1 complex. Cell 97, 17-27 (1999).

Numerous references, including patents, patent applications and various publications, are cited and discussed in the description of this invention. The citation and/or discussion of such references is provided merely to clarify the description of the present invention and is not an admission that any such reference is "prior art" to the invention described here. All references cited and/or discussed in this specification (including references, e.g., to biological sequences or structures in the GenBank, PDB or other public databases) are incorporated herein by reference in their entirety and to the same extent as if each reference was individually incorporated by reference.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed as new and desired to be protected by Letters Patent of the United States is:

1. An isolated polynucleotide molecule comprising SEQ ID NO: 2.

2. An isolated RNA molecule encoded by a polynucleotide molecule comprising SEQ ID NO: 2.

3. An isolated polynucleotide molecule consisting of SEQ ID NO: 2.

4. An isolated polynucleotide molecule consisting of SEQ ID NO: 4.

5. A recombinant vector comprising the polynucleotide molecule of claim 1.

6. An isolated host cell which has been genetically modified to express or overexpress the RNA molecule of claim 2.

7. An isolated host cell comprising the recombinant vector of claim 5.

* * * * *